United States Patent
LaVoie et al.

(10) Patent No.: US 9,458,150 B2
(45) Date of Patent: Oct. 4, 2016

(54) ANTIMICROBIAL AGENTS

(71) Applicants: Rutgers, The State University of New Jersey, New Brunswick, NJ (US); Taxis Pharmaceuticals, Inc., North Brunswick, NJ (US)

(72) Inventors: Edmond J. LaVoie, New Brunswick, NJ (US); Ajit Parhi, New Brunswick, NJ (US); Daniel S. Pilch, New Brunswick, NJ (US); Yongzheng Zhang, North Brunswick, NJ (US); Malvika Kaul, New Brunswick, NJ (US)

(73) Assignees: Rutgers, The State University of New Jersey, New Brunswick, NJ (US); Taxis Pharmaceuticals, Inc., North Brunswick, NJ (US)

( * ) Notice: Subject to any disclaimer, the term of this patent is extended or adjusted under 35 U.S.C. 154(b) by 0 days.

(21) Appl. No.: 14/536,224

(22) Filed: Nov. 7, 2014

(65) Prior Publication Data
US 2015/0133465 A1   May 14, 2015

Related U.S. Application Data

(60) Provisional application No. 61/902,095, filed on Nov. 8, 2013.

(51) Int. Cl.
| | |
|---|---|
| C07D 417/12 | (2006.01) |
| C07D 277/64 | (2006.01) |
| C07D 513/04 | (2006.01) |
| C07C 235/88 | (2006.01) |
| C07D 413/12 | (2006.01) |
| C07D 413/14 | (2006.01) |
| C07D 417/14 | (2006.01) |

(52) U.S. Cl.
CPC .......... *C07D 417/12* (2013.01); *C07C 235/88* (2013.01); *C07D 277/64* (2013.01); *C07D 413/12* (2013.01); *C07D 413/14* (2013.01); *C07D 417/14* (2013.01); *C07D 513/04* (2013.01)

(58) Field of Classification Search
CPC .................................................. C07D 417/12
See application file for complete search history.

(56) References Cited

U.S. PATENT DOCUMENTS

| | | | |
|---|---|---|---|
| 4,309,539 A | 1/1982 | Boller et al. | |
| 4,782,058 A | 11/1988 | Griffith | |
| 4,826,990 A | 5/1989 | Musser et al. | |
| 5,077,142 A | 12/1991 | Sakon et al. | |
| 5,177,067 A | 1/1993 | Guerry et al. | |
| 5,177,075 A | 1/1993 | Suto et al. | |
| 8,088,791 B2 | 1/2012 | Brown et al. | |
| 8,415,383 B2 | 4/2013 | Haydon et al. | |
| 8,492,414 B2 | 7/2013 | Haydon et al. | |
| 8,865,736 B2 | 10/2014 | Brown et al. | |
| 8,933,096 B2 | 1/2015 | LaVoie et al. | |
| 2002/0035090 A1 | 3/2002 | Zeldis et al. | |
| 2002/0040147 A1 | 4/2002 | Hammond et al. | |
| 2002/0055516 A1 | 5/2002 | Miyazaki et al. | |
| 2002/0077333 A1 | 6/2002 | Dey et al. | |
| 2003/0181519 A1 | 9/2003 | Mewshaw et al. | |
| 2005/0043300 A1 | 2/2005 | Middleton et al. | |
| 2006/0183943 A1 | 8/2006 | Hu | |
| 2008/0027028 A1 | 1/2008 | Chichak | |
| 2008/0300239 A1 | 12/2008 | Adams et al. | |
| 2009/0076074 A1 | 3/2009 | Jung et al. | |
| 2009/0312319 A1 | 12/2009 | Ren et al. | |
| 2010/0120810 A1 | 5/2010 | Leblond et al. | |
| 2012/0022061 A1 | 1/2012 | LaVoie | |
| 2013/0109713 A1 | 5/2013 | LaVoie et al. | |
| 2013/0116278 A1 | 5/2013 | LaVoie | |
| 2014/0135332 A1 | 5/2014 | Haydon et al. | |
| 2014/0350024 A1 | 11/2014 | LaVoie et al. | |
| 2015/0011559 A1 | 1/2015 | LaVoie et al. | |
| 2015/0031694 A1 | 1/2015 | LaVoie et al. | |

FOREIGN PATENT DOCUMENTS

| | | |
|---|---|---|
| DE | 4327748 A1 | 2/1995 |
| EP | 0719764 A1 | 7/1996 |
| EP | 1078920 A1 | 2/2001 |
| EP | 1724262 A1 | 11/2006 |

(Continued)

OTHER PUBLICATIONS

Chemical Abstracts Database STN, RN 1375188-04-7 for N-(methylsulfonyl)-3-[(2-methyl-4-thiazolyl)methoxy]-Benzamide, Entered STN: Jun. 5, 2012.*

Online: "http://web.archive.org/web/20070630171813/http://www.enamine.net/index.php?option=com_content&task=view&id=22&menuid=51&PHPSESSID=64a4f248f69d671a413f487bb62c4d90" dated Jun. 30, 2007, accessed Apr. 1, 2015.*

Kaul, Malvika; Mark, Lilly; Zhang, Yongzheng; Parhi, Ajit K.; LaVoie, Edmond J.; Pilch, Daniel S "Pharmacokinetics and in vivo antistaphylococcal efficacy of TXY541, a 1-methylpiperidine-4-carboxamide prodrug of PC190723." Biochemical Pharmacology (Amsterdam, Netherlands), 2013, 86(12), 1699-1707. Available online Oct. 20, 2013.*

(Continued)

*Primary Examiner* — David K O Dell
(74) *Attorney, Agent, or Firm* — Viksnins Harris & Padys PLLP

(57) ABSTRACT

The invention provides compounds of formula (I):

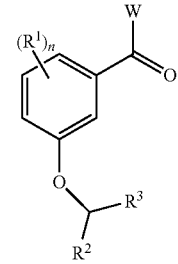

wherein $R^1$-$R^3$, n, and W have any of the values defined in the specification, and salts thereof. The compounds have good solubility and are useful for treating bacterial infections.

11 Claims, No Drawings

(56) References Cited

FOREIGN PATENT DOCUMENTS

| | | |
|---|---|---|
| WO | WO 92/19242 A1 | 11/1992 |
| WO | WO 03/018017 A1 | 3/2003 |
| WO | WO 03/078397 A1 | 9/2003 |
| WO | WO 03/099274 A1 | 12/2003 |
| WO | WO 2004/000814 A1 | 12/2003 |
| WO | WO 2004/005472 A2 | 1/2004 |
| WO | WO 2004/018414 A2 | 3/2004 |
| WO | WO 2004/041210 A2 | 5/2004 |
| WO | WO 2004/073709 A1 | 9/2004 |
| WO | WO 2004/087145 A2 | 10/2004 |
| WO | WO 2005/075428 A1 | 8/2005 |
| WO | WO 2005/097100 A2 | 10/2005 |
| WO | WO 2006/067048 A1 | 6/2006 |
| WO | WO 2006/105289 A1 | 10/2006 |
| WO | WO 2007/107758 A1 | 9/2007 |
| WO | WO 2007/148093 A1 | 12/2007 |
| WO | WO 2008/016596 A2 | 2/2008 |
| WO | WO 2009/037485 A1 | 3/2009 |
| WO | WO 2009/040507 A1 | 4/2009 |
| WO | WO 2009/074810 A1 | 6/2009 |
| WO | WO 2009/074812 A1 | 6/2009 |
| WO | WO 2010/127307 A1 | 11/2010 |
| WO | WO 2011/112435 A1 | 9/2011 |
| WO | WO 2011/156626 A1 | 12/2011 |
| WO | WO 2012/142671 A1 | 10/2012 |

OTHER PUBLICATIONS

Kaul, Malvika; Zhang, Yongzheng; Parhi, Ajit K.; LaVoie, Edmond J.; Tuske, Steve; Arnold, Eddy; Kerrigan, John E.; Pilch, Daniel S. Enterococcal and streptococcal resistance to PC190723 and related compounds: Molecular insights from a FtsZ mutational analysis. 2013 Biochimie, 95(10), 1880-1887, Available online Jun. 25, 2013.*

Eisen "Mechanism of Action of the Cell-Division Inhibitor PC190723: Modulation of FtsZ Assembly Cooperativity" J. Am. Chem. Soc. 2012, 134, 12342-12345.*

Pozharskii et. al. Heterocycles in Life and Society Wiley, 1997, pp. 1-6.*

Pitt "Heteroaromatic Rings of the Future" J. Med. Chem. 2009, 52, 2952-2963.*

Akiba et al., "Preparation of 13-Substituted 8H-Dibenzo[a,g]quinolizin-8-onces by Intramolecular Wittig-Horner Reaction of Dialkyl 2-(o-Acyl-benzoyl)-1,2-dihydro-1-isoquinolylphosphonates", Bull. Chem. Soc. Japan, 57 (8), 2188-2192 (1984).

Augstein et al., "Synthesis of 11-Hydroxy-2,3,9,10-tetramethoxy-5,6,13,13a-tetrahydro-8H-dibenzo[a, g]quinolizine. A Contribution to the Structure of Stepharotine", Stepharotine, vol. 34, No. 5, 1349-1352 (1969).

Bayer et al., "Pyridyl-substituierte Tetralonderivate: Eine neue Klasse nichsteroidaler Aromatase-Inhibitoren", Arch. Pharm. 324, 815-820 (1991). [English Abstract].

Bedi et al., "Synthesis and biological activity of novel antibacterial quinazolines", Bioorganic & Medicinal Chemistry Letters 14, 5211-5213 (2004).

Beilstein, Database Beilstein Institute for Organic Chemistry, XP002591901, Database Accession No. 3834367 (BRN) abstract (1918).

Beilstein, Database Beilstein Institute for Organic Chemistry, XP002591900, Database Accession No. 3837583(BNR) abstract (1930).

Beuria, T.K. et al., "Sanguinarine Blocks Cytokinesis in Bacteria by Inhibiting FtsZ Assembly and Bundling", Biochemistry, 44, 16584-16593 (2005).

Bild et al., "Discovery of Inhibitors of MCF-7 Tumor Cell Adhesion to Endothelial Cells and Investigation on their Mode of Action", Arch. Pharm. Pharm. Med. Chem., 337, 687-694 (2004).

Chen et al., "Synthesis and Antibacterial Evaluation of Certain Quinolone Derivatives", J. Med. Chem., 44, 2374-2377 (2001).

Cole et al., "Potential Tumor-Selective Nitroimidazolylmethyluracil Prodrug Derivatives: Inhibitors of the Angiogenic Enzyme Thymidine Phosphorylase", J. Med. Chem., 46, 207-209 (2003).

Database Registry [Online], Chemical Abstracts Service, XP002570845, Database accession No. 1043562-34-0/RN, abstract (2008).

Denes et al., "The chemistry of sanguinarine", XP002570844, Chemical Abstracts Service, Database accession No. 1960:91836, abstract, Magyar Kemiai Folyoirat, 64, 125-130 (1958).

Dyke et al., "The Chemistry of Cryptopine—I The Epicryptopines", Tetrahedr0n, vol. 24, No. 3, 1455-1465 (1968).

Dyke et al., "The Chemistry of Cryptopine—II Pseudocryptopine Chloride", Tetrahedron, vol. 25, 5375-5381 (1969).

Dykhuizen, "Santa Rosalia revisited: Why are there so many species of bacteria?", Antonie van Leeuwenhock, 73, 25-33 (1998).

Foroumadi et al., "Synthesis and in vitro antibacterial evaluation of N-[5-(5-nitro-2-thienyl)-1,3,4-thiadiazole-2-yl] piperazinyl quinolones", European Journal of Medicinal Chemistry, 38, 851-854 (2003).

Gopinath et al., "Dehydrogenation cyclization of 2-aryl-1-tetralone oxime acetates", XP002570843, Chemical Abstracts Service, Database accession No. 1960:23123, abstract, Current Science, 28, 241-242 (1959).

Huecas et al., "Protein Structure and Folding: The Interactions of Cell Division Protein FtsZ with Guanine Nucleotides", J. Biol. Chem.,282, 37515-37528 (2007).

Huttunen et al., "Prodrugs—An Efficient Way to Breach Delivery and Targeting Barriers", Current Topics in Medicinal Chemistry 11, 2265-2287 (2011).

Ishii et al., "Studies on the Chemical Constituents of Rutaceous Plants. LV.1 The Development of a Versatile Mehtod for the Synthesis of Antitumor-Active Benzo[c]phenanthridine Alkaloids. (5).1 A New Method for Quaternization of the Benzo[c]phenanthridine Nucleus", Chem. Pharm. Bull., 32(8), 2984-2994 (1984).

Ito et al., "A medium-term rat liver bioassay for rapid in vivo detection of carcinogenic potential of chemicals", Cancer Sci, vol. 94 (1), 3-8 (2003).

Jackson et al., "Non-Steroidal Aromatase Inhibitors Based on a Biphenyl Scaffold: Synthesis, in vitro SAR, and Molecular Moedelling", Chem Med Chem 3, 603-618 (2008).

Jaiswal et al., "Totarol inhibits bacterial cytokinesis by perturbing the assembly dynamics of FtsZ", Biochemistry, vol. 46(14), 4211-4220 (2007).

Kaul et al., "A Bactericidal Guanidinomethyl Biaryl That Alters the Dynamics of Bacterial FtsZ Polymerization", Journal of Medicinal Chemistry, 55, 10160-10176 (2012).

Leroux et al., "N-(4-Biphenylmethyl)imidazoles as Potential Therapeutics for the Treatment of Prostate Cancer: Metabolic Robustness Due to Fluorine Substitution?", Helvetica Chimica Acta, vol. 86, 2671-2686 (2003).

Musser et al., "N-[(Arylmethoxy)phenyl] Carboxylic Acids, Hydroxamic Acids, Tetrazoles, and Sulfonyl Carboxamides. Potent Orally Active Leukotriene D4 Antagonists of Novel Structure", J. Med. Chem. 33, 24-245 (1990).

Nicolson et al., "Potentiation of methicillin activity against methicillin-resisstant Staphylococcus aureus by diterpenes", FEMS Microbiology Letters 179, 233-239 (1999).

Okudaira et al., "A Study of the Intestinal Absorption of an Ester-Type Prodrug, ME3229, in Rats: Active Efflux Transport as a Cause of Poor Bioavailability of the Active Drug", Journal of Pharmacology and Experimental Therapeutics, vol. 294 (2), 580-587 (2000).

Patent Cooperation Treaty, International Searching Authority, Search Report and Written Opinion for PCT/US2013/069316, 12 pages, Apr. 24, 2014.

Roesch et al., "Synthesis of isoquinolines and pyridines by the palladium-catalyzed iminoannulation of internal alkynes", J. Org. Chem. 66, 8042-8051 (2001).

(56) References Cited

OTHER PUBLICATIONS

Sanders et al., "Selective Cytotoxicity of Topoisomerase-Directed Protoberberines against Glioblastoma Cells", *Biochemical Pharmacology*, vol. 56, 1157-1166 (1998).

Schonenberger, "Synthesis and Pharmacological Test of N-(3'-Methoxy-benzamidomethyl)-D-norephedrine and Analogous Compounds", *Arch. Pharm* 309, 289-301 (1976). [English Abstract].

Sethi, "Enzyme Inhibition VIII: Mode of Inhibition of Reverse Transcriptase Activity by Analogues, Isomers, and Related Alkaloids of Coralyne", *Journal of Pharmaceutical Sciences*, vol. 74 (1), 889-891 (1985).

Singh et al., "Structure—Activity Relationship Studies Leading to the Identification of (2E)-3- [I-[(2,4-Dichlorophenyl)methyl]-5-fluoro-3-methyl-1H-indol-7-yl]-N-[(4,5-dichloro-2-thienyl)sulfonyl]-2-propenamide (DG-041), a Potent and Selective Prostanoid EP3 Receptor Antagonist, as a Novel Antiplatelet gent that Does not Prolong Bleeding", *J. Med. Chem.* 53, 18-36 (2010).

Wachall et al., "Imidazole Substituted Biphenyls: A New Class of Highly Potent and In Vivo Active Inhibitors of P450 17 as Potential Therapeutics for Treatment of Prostate Cancer", *Bioorganic & Medicinal Chemistry* 7, 1913-1924 (1999).

Wigbers et al., "Synthesis, Structures, and Aggregation Properties of N-Acylamidines", *Eur. J. Org. Chem.*, 861-877 (2011).

Wu et al., "Regulatory perspectives of Type II prodrug development and time-dependent toxicity management: Nonclinical Pharm/Tox analysis and the role of comparative toxicology", *Toxicology* 236, 1-6 (2007).

Yaeko et al., "Studies on the constituents of Bocconia Cordata. IV. Transformation of sanguinarine into bocconine", XP002570841, Chemical Abstracts Service, Database accession No. 1992:129332, abstract, *Journal of Heterocyclic Chemistry*, 28(8), 1841-1843 (1991).

Yamaguchi et al., "Utilization of Protopine and Related Alkaloids. XIV. Oxidation of the Photo-adduct of 1-Oxoanhydromethylberberine with Nitrosobenzene, and Synthesis of Ring C-Substituted Benzo[c]phenanthridines", *Chem. Pharm. Bull.*, 31(5), 1601-1611 (1983).

Chemical Abstracts, STN Registry Database Record for RN 338394-05-1, Entered May 25, 2001.

Czaplewski, et al., "Antibacterial alkoxybenzamide inhibitors of the essential bacterial cell division protein FtsZ", Bioorganic & Medicinal Chemistry Letters 19, 524-527 (2009).

Dorwald, "Side Reactions in Organic Synthesis: A Guide to Successful Synthesis Design", Wiley-VCH Verlag GmbH & Co. KGaA, Wienheim, 32 pages (2005).

Kaul, et al., "An FtsZ-Targeting Prodrug with Oral Antistaphylococcal Efficacy In Vivo", Antimicrobial Agents and Chemotherapy, vol. 57 (12), 5860-5869 (2013).

* cited by examiner

ANTIMICROBIAL AGENTS

PRIORITY OF INVENTION

This application claims priority from U.S. Provisional Application No. 61/902,095, filed 8 Nov. 2013. This application is incorporated by reference herein in its entirety.

BACKGROUND OF THE INVENTION

The emergence of Multidrug Resistant (MDR) bacterial pathogens (e.g. methicillin-resistant *Staphylococcus aureus* (MRSA), *Acinetobacter baumannii-calcoaceticus* complex (ABC), etc.) has increased concerns as to the adequacy of current antimicrobials and pathogen treatment methods. The lethality of such pathogens, particularly MRSA, has often led to treatment methods that are experimental or would otherwise normally be avoided in standard clinical practice. For example, the antibiotic colistin was traditionally considered too nephrotoxic and neurotoxic for clinical use, but is nevertheless used to treat many MDR bacterial infections due to a paucity of available active drugs. The growing threat from MDR pathogens highlights a critical need for additional antimicrobials. In this connection, there is a pressing need for new antibiotics that exhibit novel mechanisms of action or that are able to circumvent known resistance pathways.

Elements of the bacterial cell division machinery present appealing targets for antimicrobial compounds because (i) they are essential for bacterial viability, (ii) they are widely conserved among bacterial pathogens, and (iii) they often have markedly different structures than their eukaryotic homologs. One such protein that has been identified as a potential target is the FtsZ protein. During the division process, FtsZ, along with approximately 15 other proteins, assemble at mid-cell into a large cell division complex (termed the divisome), ultimately facilitating cell cytokinesis. More importantly, FtsZ is widely conserved among many bacterial strains.

International Patent Application Publication Number WO 2007/107758 discusses certain compounds of the following formula:

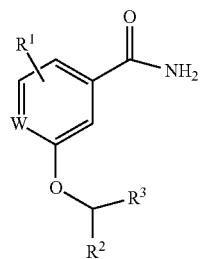

wherein W, $R^1$, $R^2$, and $R^3$ have the values defined in the application; the compounds are reported to have antibiotic activity. Unfortunately, certain of the compounds discussed in this publication have solubility properties that may severely limit their use as pharmaceutical agents. Accordingly, there remains a need for antibacterial compounds that have physical properties (e.g. solubility) that make them useful as pharmaceutical agents.

SUMMARY OF THE INVENTION

Applicant has identified a series of antibiotic compounds that are highly soluable and that can be formulated for administration as antibiotic agents. Accordingly, in one embodiment the invention provides a compound of the invention which is a compound of formula (I):

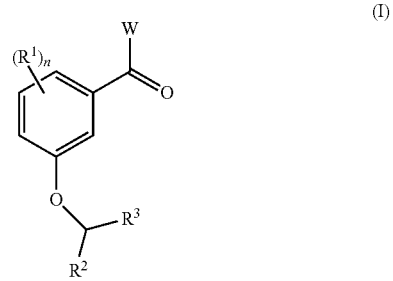

wherein:
each $R^1$ is independently selected from hydrogen, halo, cyano, nitro, $(C_1-C_6)$alkyl, $(C_1-C_6)$alkoxy, $(C_1-C_6)$alkanoyl, $(C_1-C_6)$alkoxycarbonyl, $(C_1-C_6)$alkanoyloxy, aryl, heteroaryl, heterocycle, and $NR^eR^f$, wherein each $(C_1-C_6)$alkyl, $(C_1-C_6)$alkoxy, $(C_1-C_6)$alkanoyl, $(C_1-C_6)$alkoxycarbonyl, $(C_1-C_6)$alkanoyloxy, aryl, heteroaryl, and heterocycle is optionally substituted with one or more groups independently selected from halo, cyano, nitro, $NR^eR^f$, $-CR^g(=N)N(R^g)_2$, $-NR^gC(=N)-N(R^g)_2$, $-NR^g-C(=NR^g)R^g$, $(C_1-C_3)$alkyl, $(C_1-C_3)$alkoxy, $(C_1-C_3)$alkanoyl, $(C_1-C_3)$alkoxycarbonyl, $(C_1-C_3)$alkanoyloxy, aryl, heteroaryl, and heterocycle;

$R^2$ is H or $(C_1-C_6)$alkyl that is optionally substituted with one or more groups independently selected from $-OR^k$, halo, $NR^eR^f$, $NR^eR^f$, $-CR^g(=N)N(R^g)_2$, $-NR^gC(=N)-N(R^g)_2$, and $-NR^g-C(=NR^g)R^g$;

$R^3$ is aryl or heteroaryl, which aryl or heteroaryl is optionally substituted with one or more groups independently selected from $R^h$, halo, hydroxy, $-NR^eR^f$, $-CR^g(=N)N(R^g)_2$, $-NR^gC(=N)-N(R^g)_2$, $-NR^g-C(=NR^g)R^g$, $(C_1-C_6)$alkyl, and $(C_3-C_8)$cycloalkyl, wherein any $(C_1-C_6)$alkyl and $(C_3-C_8)$cycloalkyl is optionally substituted with one or more groups independently selected from halo, hydroxy, $-NR^eR^f$, $-CR^g(=N)N(R^g)_2$, $-NR^gC(=N)-N(R^g)_2$, $-NR^g-C(=NR^g)R^g$, and $(C_1-C_6)$alkyl that is optionally substituted with one or more groups independently selected from halo;

W is $-NHCOR^a$, $-N(COR^a)(COR^b)$, $-N=C(R^c)NR^aR^b$, $-NR^aCH_2OR^a$, $-NHC(=O)OR^a$, $-NHC(=O)NR^aR^b$, or $-N(R^a)SO_mR^d$;

each $R^a$ is independently selected from H, aryl, heteroaryl, heterocycle, $(C_3-C_8)$cycloalkyl, $(C_3-C_8)$cycloalkyl$(C_1-C_6)$alkyl and $(C_1-C_6)$alkyl that is optionally substituted with one or more groups independently selected from hydroxy, halo, cyano, $(C_1-C_6)$alkoxycarbonyl, aryl, heteroaryl, $-NR^eR^f$, $-CR^g(=N)N(R^g)_2$, $-NR^gC(=N)-N(R^g)_2$, $-NR^g-C(=NR^g)R^g$ and heterocycle; wherein any aryl, heteroaryl, heterocycle, and $(C_3-C_8)$cycloalkyl$(C_1-C_6)$alkyl of $R^a$ is optionally substituted with one or more groups independently selected from hydroxy, halo, cyano, trifluoromethoxy, $(C_1-C_6)$alkyl, $(C_1-C_6)$alkoxy, halo$(C_1-C_6)$alkyl, $-NR^eR^f$, $-CR^g(=N)N(R^g)_2$, $-NR^gC(=N)-N(R^g)_2$, $-NR^g-C(=NR^g)R^g$, and $(C_1-C_6)$alkoxycarbonyl;

each $R^b$ is independently selected from H and $(C_1-C_6)$alkyl that is optionally substituted with one or more groups independently selected from hydroxy, halo, cyano, $(C_1-C_6)$alkoxycarbonyl, aryl, heteroaryl, $-NR^eR^f$, $-CR^g(=N)N(R^g)_2$, $-NR^gC(=N)-N(R^g)_2$, $-NR^g-C(=NR^g)R^g$, and heterocycle;

each $R^c$ is independently selected from H and $(C_1-C_6)$ alkyl that is optionally substituted with one or more groups independently selected from halo;

each $R^d$ is independently selected from OH, $-NH_2$, $-NR^eR^f$, aryl, heteroaryl, heterocycle, and $(C_1-C_6)$alkyl that is optionally substituted with one or more groups independently selected from hydroxy, halo, cyano, $(C_1-C_6)$ alkoxycarbonyl, aryl, heteroaryl, $-NR^eR^f$, $-CH(=N)NH_2$, $-NHC(=N)-NH_2$, $-NH-C(=NH)R$, and heterocycle;

each $R^e$ is independently selected from H, aryl, heteroaryl, heterocycle, and $(C_1-C_6)$alkyl that is optionally substituted with one or more groups independently selected from hydroxy, halo, cyano, $(C_1-C_6)$alkoxycarbonyl, aryl, heteroaryl, and heterocycle; and each $R^f$ is independently selected from H and $(C_1-C_6)$alkyl that is optionally substituted with one or more groups independently selected from hydroxyl, halo, cyano, $(C_1-C_6)$alkoxycarbonyl, aryl, heteroaryl, and heterocycle; or $R^e$ and $R^f$ together with the nitrogen to which they are attached form a aziridino, azetidino, morpholino, piperazino, pyrrolidino or piperidino;

each $R^g$ is independently selected from H and $(C_1-C_6)$ alkyl that is optionally substituted with one or more groups independently selected from halo;

each $R^h$ is independently selected from aryl and heteroaryl, wherein any aryl and heteroaryl of $R^h$ is optionally substituted with one or more groups independently selected from $R^m$, halo, hydroxy, $-NR^eR^f$, $-CR^g(=N)N(R^g)_2$, $-NR^gC(=N)-N(R^g)_2$, $-NR^g-C(=NR^g)R^g$ and $(C_1-C_6)$ alkyl that is optionally substituted with one or more groups independently selected from hydroxy, halo, $-NR^eR^f$, $-CR^g(=N)N(R^g)_2$, $-NR^gC(=N)-N(R^g)_2$, and $-NR^g-C(=NR^g)R^g$;

each $R^k$ is independently selected from H or $(C_1-C_6)$alkyl that is optionally substituted with one or more groups independently selected from hydroxy, halo, oxo, carboxy, $(C_1-C_6)$alkoxy, $(C_1-C_6)$alkoxycarbonyl, and $(C_1-C_6)$alkanoyloxy;

each $R^m$ is independently selected from $(C_1-C_6)$alkoxy that is optionally substituted with one or more groups independently selected from hydroxy, halo, oxo, carboxy, $(C_1-C_6)$alkoxy, $(C_1-C_6)$alkoxycarbonyl, and $(C_1-C_6)$alkanoyloxy;

m is 0, 1, or 2; and n is 1, 2, 3, or 4;

or a salt thereof.

The invention also provides a method for treating a bacterial infection in a mammal comprising administering to the mammal an effective amount of a compound of formula I or a pharmaceutically acceptable salt thereof.

The invention also provides a composition comprising a compound of formula I, or a pharmaceutically acceptable salt thereof, and a pharmaceutically acceptable vehicle.

The invention also provides a compound of formula I or a pharmaceutically acceptable salt thereof for the prophylactic or therapeutic treatment of a bacterial infection.

The invention also provides a compound of formula I or a pharmaceutically acceptable salt thereof for use in medical treatment.

The invention also provides the use of a compound of formula I or a pharmaceutically acceptable salt thereof for the preparation of a medicament for treating a bacterial infection in a mammal.

The invention also provides processes and intermediates disclosed herein that are useful for preparing compounds of formula I or salts thereof.

DETAILED DESCRIPTION

The following definitions are used, unless otherwise described: halo is fluoro, chloro, bromo, or iodo. Alkyl and alkoxy, etc. denote both straight and branched groups but reference to an individual radical such as propyl embraces only the straight chain radical (a branched chain isomer such as isopropyl being specifically referred to).

As used herein, the term "$(C_a-C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

The term "aryl" as used herein refers to a single aromatic ring or a multiple condensed ring system. For example, an aryl group can have 6 to 20 carbon atoms, 6 to 14 carbon atoms, or 6 to 12 carbon atoms. Aryl includes a phenyl radical. Aryl also includes multiple condensed ring systems (e.g. ring systems comprising 2, 3 or 4 rings) having about 9 to 20 carbon atoms in which at least one ring is aromatic. Such multiple condensed ring systems may be optionally substituted with one or more (e.g. 1, 2 or 3) oxo groups on any carbocycle portion of the multiple condensed ring system. It is to be understood that the point of attachment of a multiple condensed ring system, as defined above, can be at any position of the ring system including an aryl or a carbocycle portion of the ring. Typical aryl groups include, but are not limited to, phenyl, indenyl, naphthyl, 1, 2, 3, 4-tetrahydronaphthyl, anthracenyl, and the like.

The term "heteroaryl" as used herein refers to a single aromatic ring or a multiple condensed ring system. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2, 3 or 4 rings) wherein a heteroaryl group, as defined above, can be condensed with one or more heteroaryls (e.g. naphthyridinyl), heterocycles, (e.g. 1, 2, 3, 4-tetrahydronaphthyridinyl), carbocycles (e.g. 5,6,7,8-tetrahydroquinolyl) or aryls (e.g. indazolyl) to form a multiple condensed ring system. Such multiple condensed ring systems may be optionally substituted with one or more (e.g. 1, 2, 3 or 4) oxo groups on the carbocycle or heterocycle portions of the condensed ring. It is to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g. a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl, benzofuranyl, benzimidazolyl and thianaphthenyl.

The term "heterocyclyl" or "heterocycle" as used herein refers to a single saturated or partially unsaturated ring or a multiple condensed ring system. The term includes single saturated or partially unsaturated rings (e.g. 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g. 1, 2 or 3) oxo groups and the sulfur and nitrogen atoms may also be present in their oxidized forms. Such rings include but are not limited to azetidinyl, tetrahydrofuranyl or piperidinyl. The term "heterocycle" also includes multiple condensed ring systems (e.g. ring systems comprising 2, 3 or 4 rings) wherein a single heterocycle ring (as defined above) can be condensed with one or more heterocycles (e.g. decahydronapthyridinyl), carbocycles (e.g. decahydroquinolyl) or aryls. The rings of a multiple condensed ring system can be connected to each other via fused, spiro and bridged bonds when allowed by valency requirements. It is to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g. a nitrogen). Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl.

The term "halo($C_1$-$C_6$)alkyl" includes an alkyl group as defined herein that is substituted with one or more (e.g. 1, 2, 3, or 4) halo groups.

The term "($C_3$-$C_8$)cycloalkyl" includes saturated and partially unsaturated carbocyclic ring systems, which may include mono, fused and spiro ring systems.

Specific values listed below for radicals, substituents, and ranges, are for illustration only; they do not exclude other defined values or other values within defined ranges for the radicals and substituents.

Specifically, ($C_1$-$C_6$)alkyl can be methyl, ethyl, propyl, isopropyl, butyl, iso-butyl, sec-butyl, pentyl, 3-pentyl, or hexyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_3$-$C_8$)cycloalkyl can be cyclopropyl, cyclobutyl, cyclopentyl, or cyclohexyl; ($C_1$-$C_6$)alkanoyl can be acetyl, propanoyl or butanoyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; halo($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; ($C_2$-$C_6$)alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

In one embodiment of the each $R^1$ is halo.

In one embodiment of the invention $R^2$ is H.

In one embodiment of the invention $R^2$ is ($C_1$-$C_6$)alkyl that is optionally substituted with one or more groups independently selected from hydroxy, $NR^eR^f$, —CH(=N)$NH_2$, —NHC(=N)—$NH_2$, and —NH—C(=NH)R.

In one embodiment of the invention $R^2$ is ($C_1$-$C_6$)alkyl that is optionally substituted with one or more groups independently selected from hydroxy, halo, —$NR^eR^f$, —$CR^g$(=N)N($R^g$)$_2$, —$NR^gC$(=N)—N($R^g$)$_2$, and —$NR^g$—C(=$NR^g$)$R^g$.

In one embodiment of the invention $R^3$ is aryl, which is optionally substituted with one or more groups independently selected from halo, hydroxy, $NR^eR^f$, —$CR^g$(=N)N($R^g$)$_2$, —$NR^gC$(=N)—N($R^g$)$_2$, —$NR^g$—C(=$NR^g$)$R^g$, and ($C_1$-$C_6$)alkyl that is optionally substituted with one or more groups independently selected from hydroxy, $NR^eR^f$, —$CR^g$(=N)N($R^g$)$_2$, —$NR^gC$(=N)—N($R^g$)$_2$, and —$NR^g$—C(=$NR^g$)$R^g$.

In one embodiment of the invention $R^3$ is heteroaryl, which is optionally substituted with one or more groups independently selected from halo, hydroxy, $NR^eR^f$, —$CR^g$(=N)N($R^g$)$_2$, —$NR^gC$(=N)—N($R^g$)$_2$, —$NR^g$—C(=$NR^g$)$R^g$, and ($C_1$-$C_6$)alkyl that is optionally substituted with one or more groups independently selected from hydroxy, $NR^eR^f$, —$CR^g$(=N)N($R^g$)$_2$, —$NR^gC$(=N)—N($R^g$)$_2$, and —$NR^g$—C(=$NR^g$)$R^g$.

In one embodiment of the invention $R^3$ is:

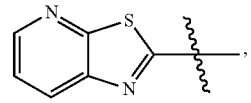

which is optionally substituted with one or more groups independently selected from halo, hydroxy, $NR^eR^f$, —$CR^g$(=N)N($R^g$)$_2$, —$NR^gC$(=N)—N($R^g$)$_2$, —$NR^g$—C(=$NR^g$)$R^g$, and ($C_1$-$C_6$)alkyl that is optionally substituted with one or more groups independently selected from hydroxy, $NR^eR^f$, —$CR^g$(=N)N($R^g$)$_2$, —$NR^gC$(=N)—N($R^g$)$_2$, and —$NR^g$—C(=$NR^g$)$R^g$.

In one embodiment of the invention $R^3$ is:

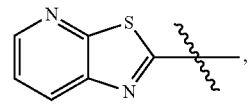 [SMILES: *c1nc2cccnc2s1]

which is optionally substituted with one or more groups independently selected from halo.

In one embodiment of the invention $R^3$ is:

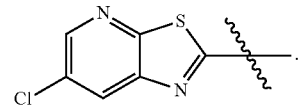 [SMILES: *c1nc2cc(Cl)cnc2s1]

In one embodiment of the invention $R^3$ is:

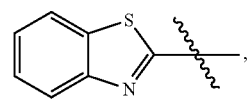

which is optionally substituted with one or more groups independently selected from halo, hydroxy, $NR^eR^f$, —$CR^g$(=N)N($R^g$)$_2$, —$NR^gC$(=N)—N($R^g$)$_2$, —$NR^g$—C(=$NR^g$)$R^g$, and ($C_1$-$C_6$)alkyl that is optionally substituted with one or more groups independently selected from hydroxy, $NR^eR^f$, —$CR^g$(=N)N($R^g$)$_2$, —$NR^gC$(=N)—N($R^g$)$_2$, and —$NR^g$—C(=$NR^g$)$R^g$.

In one embodiment of the invention $R^3$ is:

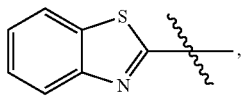 [SMILES: *c1nc2ccccc2s1]

which is optionally substituted with one or more groups independently selected from halo.

In one embodiment of the invention $R^3$ is:

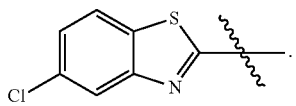 [SMILES: *c1nc2cc(Cl)ccc2s1]

In one embodiment of the invention W is —NHC(=O)H, —NHC(=O)CH$_3$, —NHC(=O)CH$_2$CH$_3$, —NHC(=O)CH$_2$CH$_2$CH$_3$, —N(H)SO$_2$CH$_3$, —N=NCH—N(CH$_3$)$_2$, —NHCH$_2$OH, —N=NC(CH$_3$)—N(CH$_3$)$_2$,

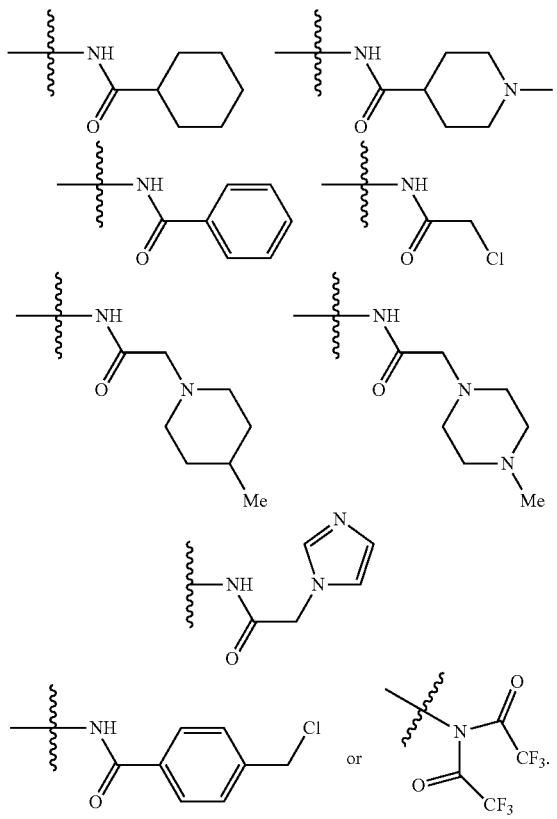

or

In one embodiment the invention provides a compound of formula (Ia):

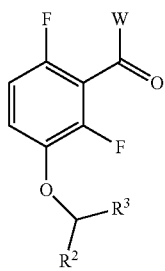

(Ia)

or a salt thereof.

In one embodiment:

each $R^1$ is independently selected from hydrogen, halo, cyano, nitro, ($C_1$-$C_6$)alkyl, ($C_1$-$C_6$)alkoxy, ($C_1$-$C_6$)alkanoyl, ($C_1$-$C_6$)alkoxycarbonyl, ($C_1$-$C_6$)alkanoyloxy, aryl, heteroaryl, heterocycle, and NR$^e$R$^f$, wherein each ($C_1$-$C_6$)alkyl, ($C_1$-$C_6$)alkoxy, ($C_1$-$C_6$)alkanoyl, ($C_1$-$C_6$)alkoxycarbonyl, ($C_1$-$C_6$)alkanoyloxy, aryl, heteroaryl, and heterocycle is optionally substituted with one or more groups independently selected from halo, cyano, nitro, —NR$^e$R$^f$, —CR$^g$(=N)N(R$^g$)$_2$, —NR$^g$C(=N)—N(R$^g$)$_2$, —NR$^g$—C(=NR$^g$)R$^g$, ($C_1$-$C_3$)alkyl, ($C_1$-$C_3$)alkoxy, ($C_1$-$C_3$)alkanoyl, ($C_1$-$C_3$)alkoxycarbonyl, ($C_1$-$C_3$)alkanoyloxy, aryl, heteroaryl, and heterocycle;

$R^2$ is H or ($C_1$-$C_6$)alkyl that is optionally substituted with one or more groups independently selected from hydroxy, —NR$^e$R$^f$, —CR$^g$(=N)N(R$^g$)$_2$, —NR$^g$C(=N)—N(R$^g$)$_2$, and —NR$^g$—C(=NR$^g$)R$^g$;

$R^3$ is aryl or heteroaryl, which aryl or heteroaryl is optionally substituted with one or more groups independently selected from R$^h$, halo, hydroxy, —NR$^e$R$^f$, —CR$^g$(=N)N(R$^g$)$_2$, —NR$^g$C(=N)—N(R$^g$)$_2$, —NR$^g$—C(=NR$^g$)R$^g$ and ($C_1$-$C_6$)alkyl that is optionally substituted with one or more groups independently selected from hydroxy, —NR$^e$R$^f$, —CR$^g$(=N)N(R$^g$)$_2$, —NR$^g$C(=N)—N(R$^g$)$_2$, and —NR$^g$—C(=NR$^g$)R$^g$;

W is —NHCOR$^a$, —N(COR$^a$)(COR$^b$), —N=C(R$^c$)NR$^a$R$^b$, —NR$^a$CH$_2$OR$^a$, or —N(R$^a$)SO$_m$R$^d$;

each $R^a$ is independently selected from H, aryl, heteroaryl, heterocycle, ($C_3$-$C_8$)cycloalkyl, ($C_3$-$C_8$)cycloalkyl($C_1$-$C_6$)alkyl and ($C_1$-$C_6$)alkyl that is optionally substituted with one or more groups independently selected from hydroxyl, halo, cyano, ($C_1$-$C_6$)alkoxycarbonyl, aryl, heteroaryl, —NR$^e$R$^f$, —CR$^g$(=N)N(R$^g$)$_2$, —NR$^g$C(=N)—N(R$^g$)$_2$, —NR$^g$—C(=NR$^g$)R$^g$ and heterocycle; wherein any aryl, heteroaryl, heterocycle, and ($C_3$-$C_8$)cycloalkyl($C_1$-$C_6$)alkyl of R$^a$ is optionally substituted with one or more groups independently selected from hydroxy, halo, cyano, trifluoromethoxy, ($C_1$-$C_6$)alkyl, halo($C_1$-$C_6$)alkyl, —NR$^e$R$^f$, —CR$^g$(=N)N(R$^g$)$_2$, —NR$^g$C(=N)—N(R$^g$)$_2$, —NR$^g$—C(=NR$^g$)R$^g$, and ($C_1$-$C_6$)alkoxycarbonyl;

each $R^b$ is independently selected from H and ($C_1$-$C_6$)alkyl that is optionally substituted with one or more groups independently selected from hydroxyl, halo, cyano, ($C_1$-$C_6$)alkoxycarbonyl, aryl, heteroaryl, —NR$^e$R$^f$, —CR$^g$(=N)N(R$^g$)$_2$, —NR$^g$C(=N)—N(R$^g$)$_2$, —NR$^g$—C(=NR$^g$)R$^g$, and heterocycle;

each $R^c$ is independently selected from H and ($C_1$-$C_6$)alkyl;

each $R^d$ is independently selected from OH, —NH$_2$, —NR$^e$R$^f$, aryl, heteroaryl, heterocycle, and ($C_1$-$C_6$)alkyl that is optionally substituted with one or more groups independently selected from hydroxy, halo, cyano, ($C_1$-$C_6$)alkoxycarbonyl, aryl, heteroaryl, —NR$^e$R$^f$, —CH(=N)NH$_2$, —NHC(=N)—NH$_2$, —NH—C(=NH)R, and heterocycle;

each $R^e$ is independently selected from H, aryl, heteroaryl, heterocycle, and ($C_1$-$C_6$)alkyl that is optionally substituted with one or more groups independently selected from hydroxyl, halo, cyano, ($C_1$-$C_6$)alkoxycarbonyl, aryl, heteroaryl, and heterocycle; and each $R^f$ is independently selected from H and ($C_1$-$C_6$)alkyl that is optionally substituted with one or more groups independently selected from hydroxyl, halo, cyano, ($C_1$-$C_6$)alkoxycarbonyl, aryl, heteroaryl, and heterocycle; or R$^e$ and R$^f$ together with the nitrogen to which they are attached form a aziridino, azetidino, morpholino, piperazino, pyrrolidino or piperidino;

each $R^g$ is independently selected from H and $(C_1-C_6)$alkyl;

each $R^h$ is independently selected from aryl and heteroaryl, wherein any aryl and heteroaryl of $R^h$ is optionally substituted with one or more groups independently selected from halo, hydroxy, —$NR^eR^f$, —$CR^g(=N)N(R^g)_2$, —$NR^gC(=N)$—$N(R^g)_2$, —$NR^g$—$C(=NR^g)R^g$ and $(C_1-C_6)$alkyl that is optionally substituted with one or more groups independently selected from hydroxy, —$NR^eR^f$, —$CR^g(=N)N(R^g)_2$, —$NR^gC(=N)$—$N(R^g)_2$, and —$NR^g$—$C(=NR^g)R^g$;

m is 0, 1, or 2; and n is 1, 2, 3, or 4.

In one embodiment W is —$NHCOR^a$, —$N(COR^a)(COR^b)$, —$NR^aCH_2OR^a$, —$NHC(=O)OR^a$, —$NHC(=O)NR^aR^b$, or —$N(R^a)SO_mR^d$;

In one embodiment the invention provides a compound selected from:

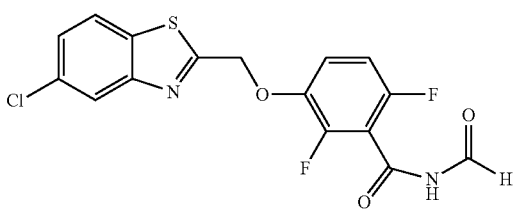

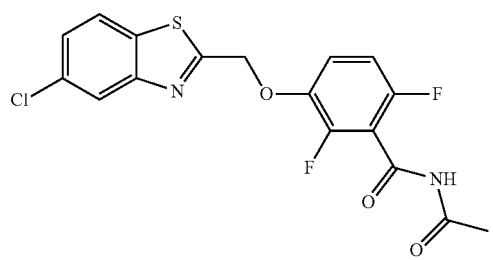

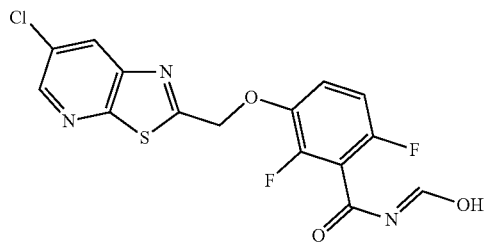

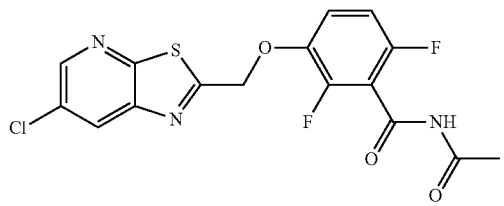

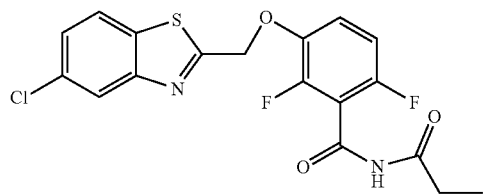

-continued

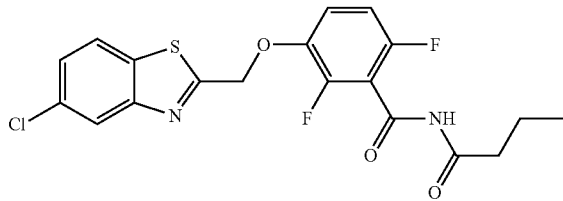

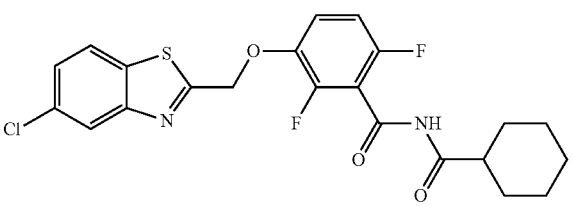

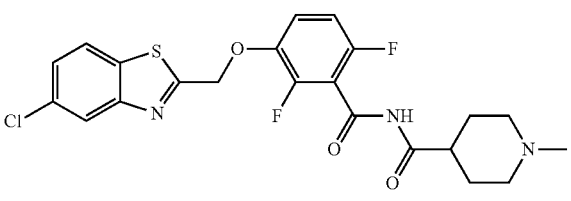

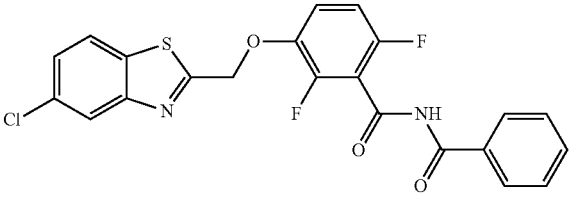

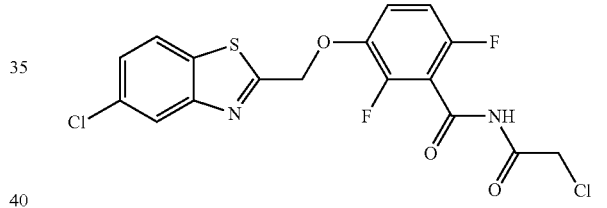

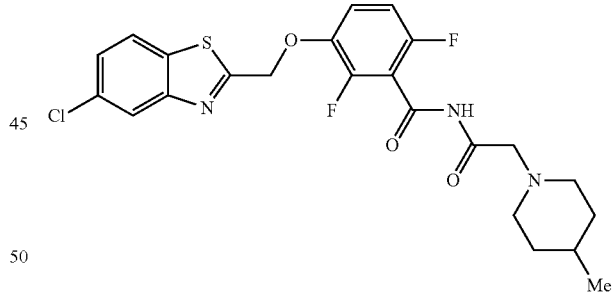

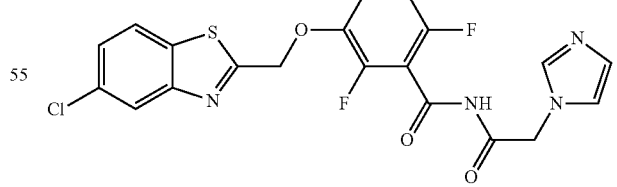

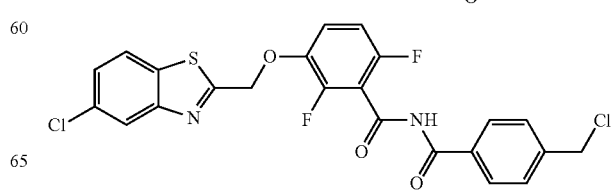

11
-continued
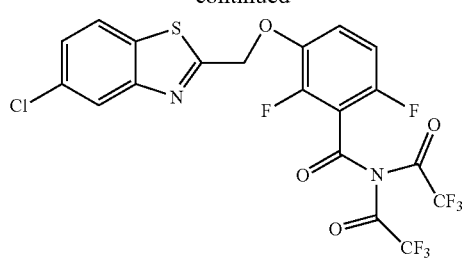
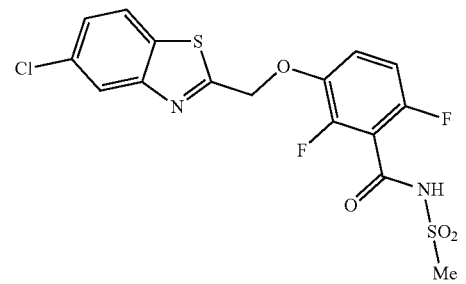
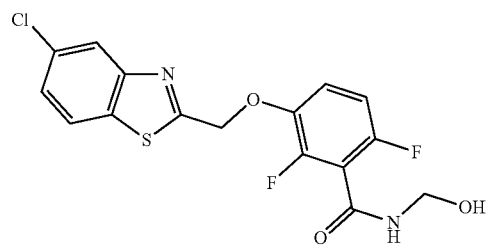
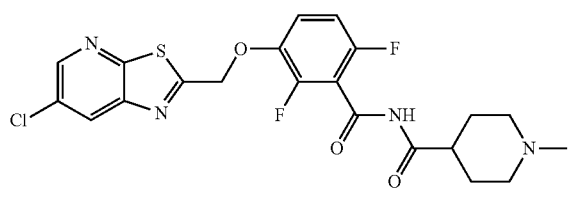
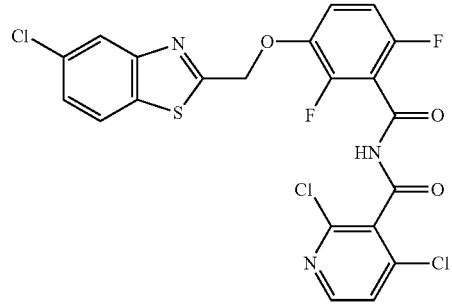
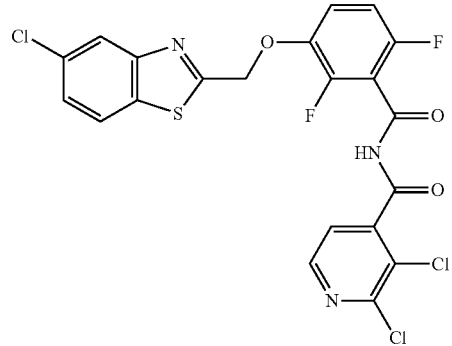
12
-continued
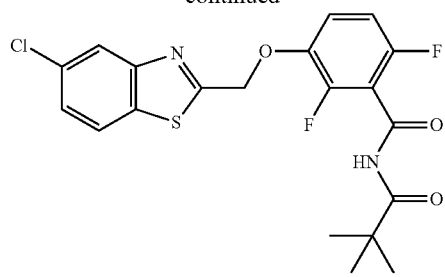
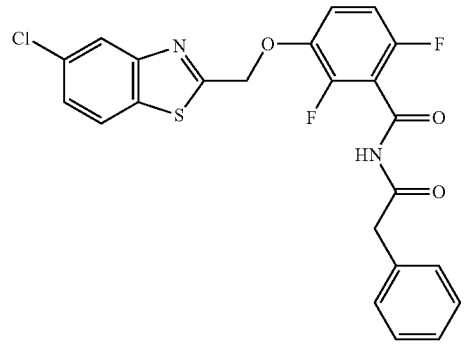
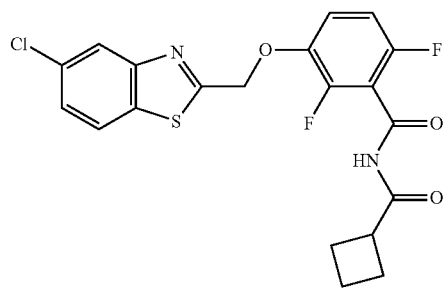
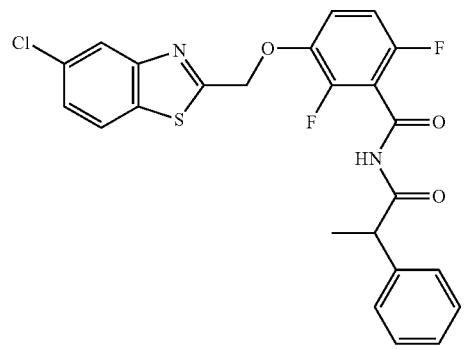
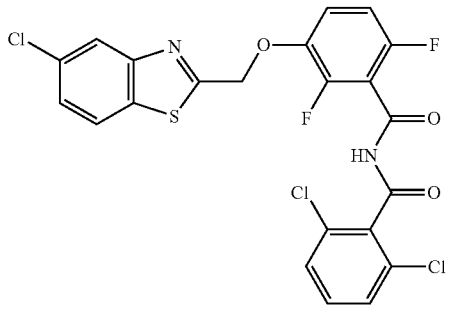

-continued
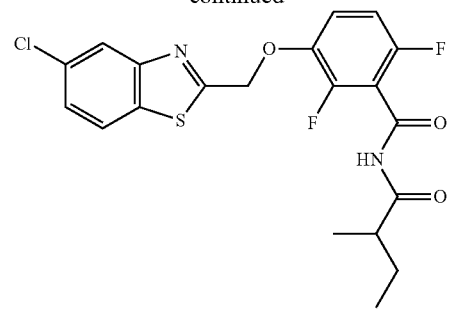
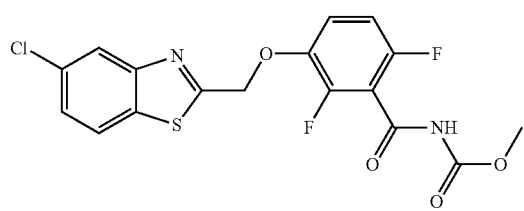
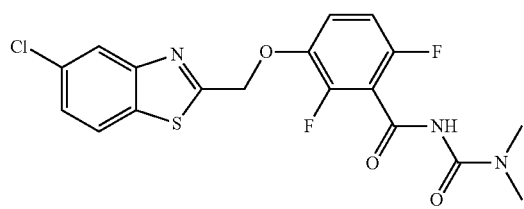
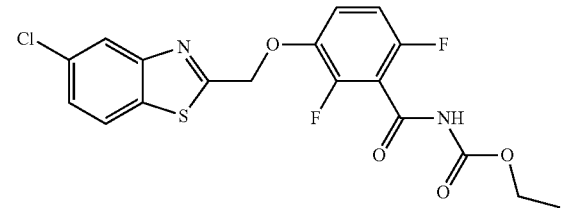
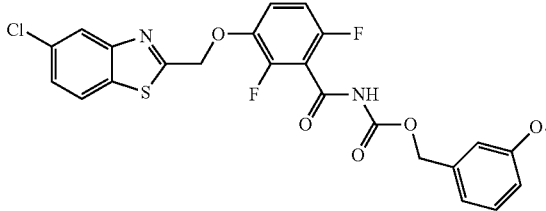
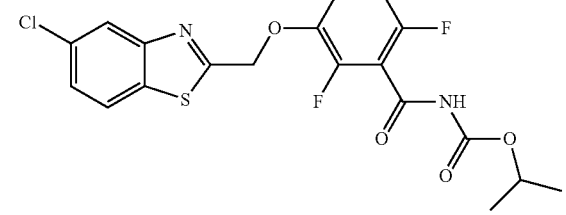
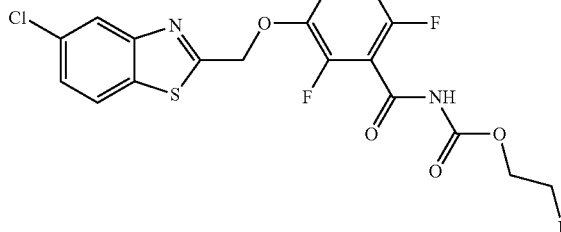
-continued
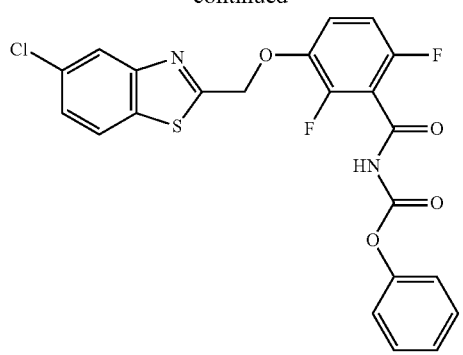
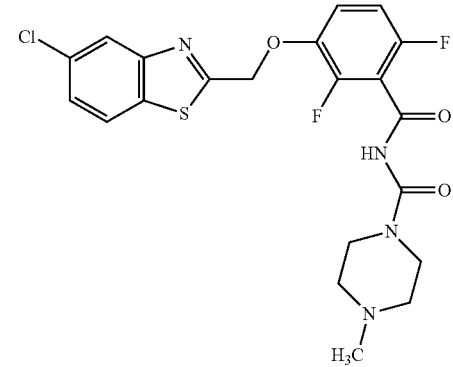
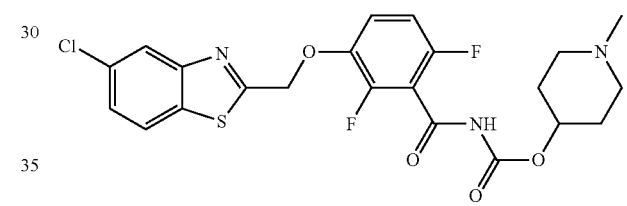
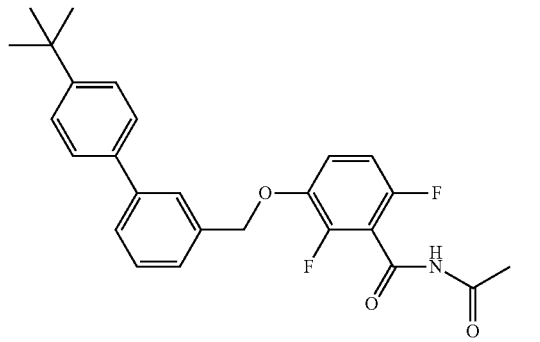
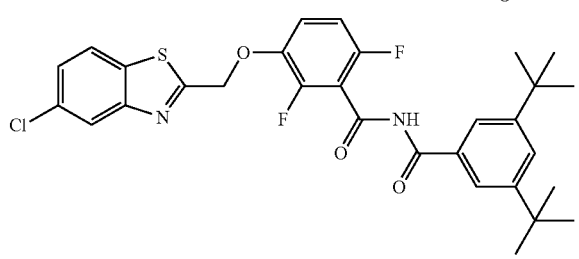

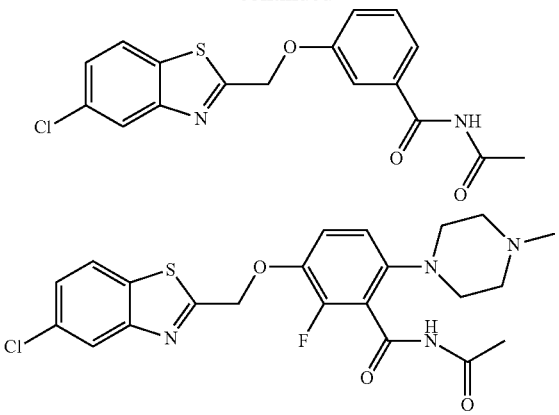
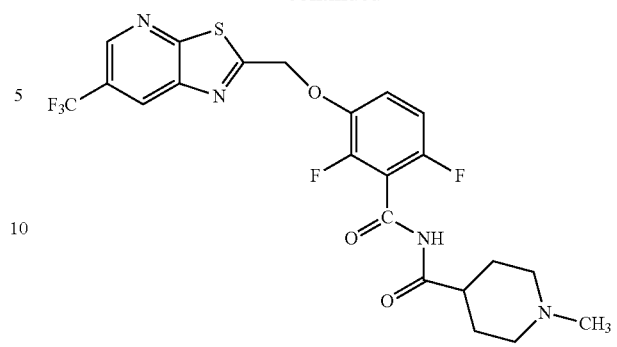
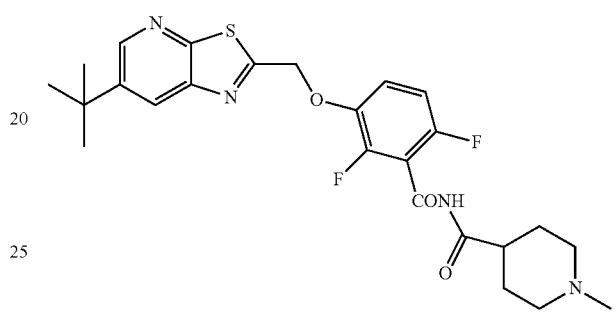
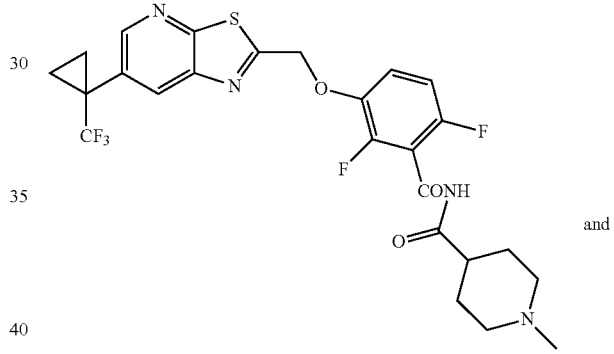
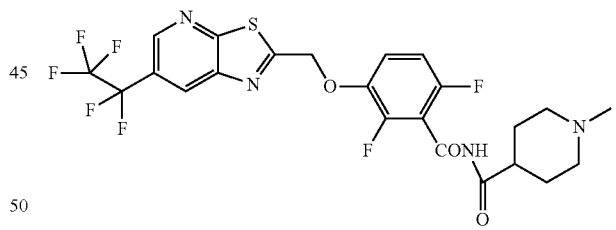
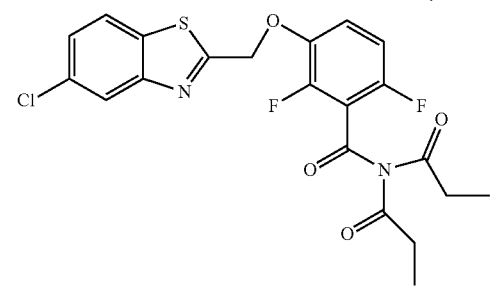
and salts thereof.
In one embodiment the invention provides a compound selected from:
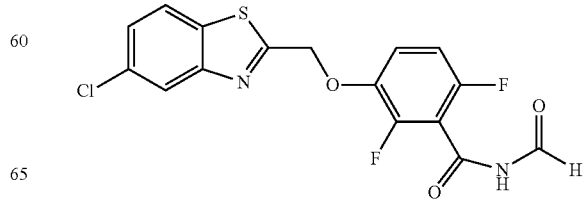

-continued
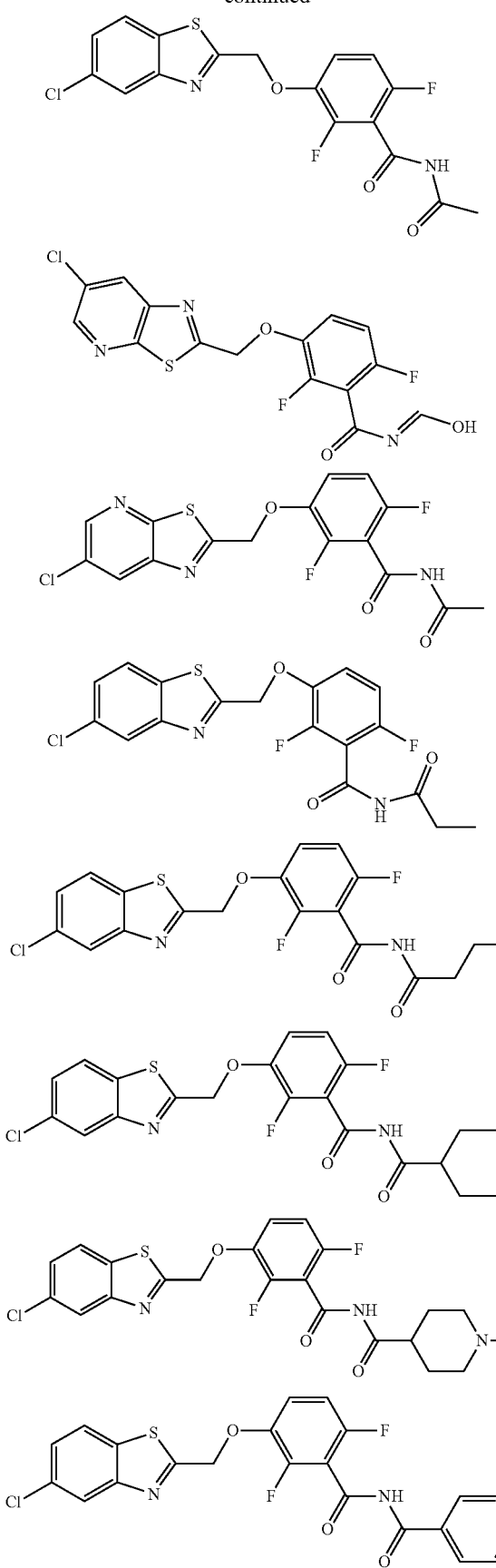
-continued
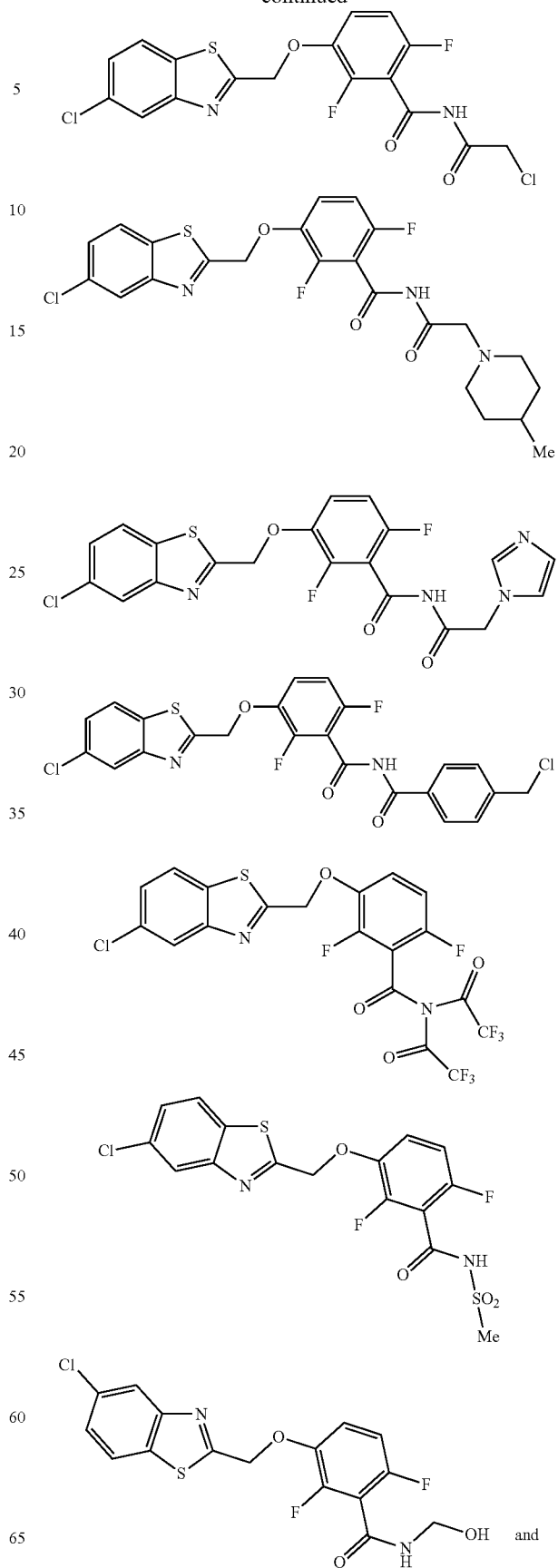

-continued

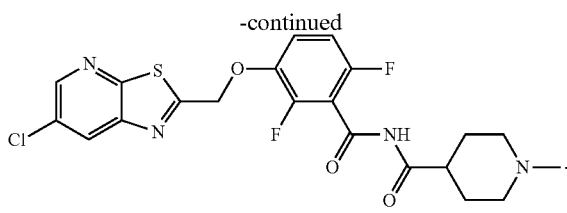

In one embodiment of the invention R³ is aryl, which is optionally substituted with one or more groups independently selected from R^h, halo, hydroxy, —NR^eR^f, —CR^g(=N)N(R^g)₂, —NR^gC(=N)—N(R^g)₂, —NR^g—C(=NR^g)R^g, (C₁-C₆)alkyl and (C₃-C₈)cycloalkyl, wherein any (C₁-C₆)alkyl and (C₃-C₈)cycloalkyl is optionally substituted with one or more groups independently selected from halo, hydroxy, —NR^eR^f, —CR^g(=N)N(R^g)₂, —NR^gC(=N)—N(R^g)₂, —NR^g—C(=NR^g)R^g, and (C₁-C₆)alkyl that is optionally substituted with one or more groups independently selected from halo.

In one embodiment of the invention R³ is heteroaryl, which is optionally substituted with one or more groups independently selected from R^h, halo, hydroxy, —NR^eR^f, —CR^g(=N)N(R^g)₂, —NR^gC(=N)—N(R^g)₂, —NR^g—C(=NR^g)R^g, (C₁-C₆)alkyl, and (C₃-C₈)cycloalkyl, wherein any (C₁-C₆)alkyl and (C₃-C₈)cycloalkyl is optionally substituted with one or more groups independently selected from halo, hydroxy, —NR^eR^f, —CR^g(=N)N(R^g)₂, —NR^gC(=N)—N(R^g)₂, —NR^g—C(=NR^g)R^g, and (C₁-C₆)alkyl that is optionally substituted with one or more groups independently selected from halo.

In one embodiment of the invention R³ is:

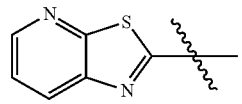 [SMILES: *c1nc2cccnc2s1]

which is optionally substituted with one or more groups independently selected from R^h, halo, hydroxy, —NR^eR^f, —CR^g(=N)N(R^g)₂, —NR^gC(=N)—N(R^g)₂, —NR^g—C(=NR^g)R^g, (C₁-C₆)alkyl, and (C₃-C₈)cycloalkyl, wherein any (C₁-C₆)alkyl and (C₃-C₈)cycloalkyl is optionally substituted with one or more groups independently selected from halo, hydroxy, —NR^eR^f, —CR^g(=N)N(R^g)₂, —NR^gC(=N)—N(R^g)₂, —NR^g—C(=NR^g)R^g, and (C₁-C₆)alkyl that is optionally substituted with one or more groups independently selected from halo.

In one embodiment of the invention R³ is:

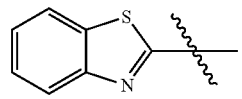 [SMILES: *c1nc2ccccc2s1]

which is optionally substituted with one or more groups independently selected from R^h, halo, hydroxy, —NR^eR^f, —CR^g(=N)N(R^g)₂, —NR^gC(=N)—N(R^g)₂, —NR^g—C(=NR^g)R^g, (C₁-C₆)alkyl, and (C₃-C₈)cycloalkyl, wherein any (C₁-C₆)alkyl and (C₃-C₈)cycloalkyl is optionally substituted with one or more groups independently selected from halo, hydroxy, —NR^eR^f, —CR^g(=N)N(R^g)₂, —NR^gC(=N)—N(R^g)₂, —NR^g—C(=NR^g)R^g, and (C₁-C₆)alkyl that is optionally substituted with one or more groups independently selected from halo.

In one embodiment of the invention R³ is:

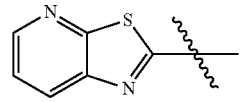 [SMILES: *c1nc2cccnc2s1]

which is optionally substituted with one or more groups independently selected from (C₁-C₆)alkyl, and (C₃-C₈)cycloalkyl, wherein any (C₁-C₆)alkyl and (C₃-C₈)cycloalkyl is optionally substituted with one or more groups independently selected from halo, hydroxy, and (C₁-C₆)alkyl that is optionally substituted with one or more groups independently selected from halo.

In one embodiment of the invention R³ is:

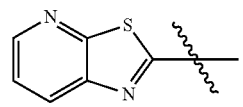

which is substituted with one or more groups independently selected from (C₁-C₆)alkyl, and (C₃-C₈)cycloalkyl, wherein any (C₁-C₆)alkyl and (C₃-C₈)cycloalkyl is optionally substituted with one or more groups independently selected from halo and (C₁-C₆)alkyl that is optionally substituted with one or more groups independently selected from halo.

In one embodiment of the invention R³ is:

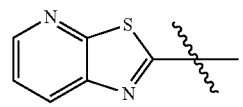 [SMILES: *c1nc2cccnc2s1]

which is substituted with one or more groups independently selected from trifluoromethyl, pentafluoroethyl, or 1-(trifluoromethyl)cyclopropyl.

In one embodiment of the invention R³ is:

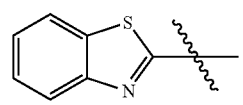 [SMILES: *c1nc2ccccc2s1]

which is optionally substituted with one or more groups independently selected from (C₁-C₆)alkyl, and (C₃-C₈)cycloalkyl, wherein any (C₁-C₆)alkyl and (C₃-C₈)cycloalkyl is optionally substituted with one or more groups independently selected from halo, hydroxy, and (C₁-C₆)alkyl that is optionally substituted with one or more groups independently selected from halo.

In one embodiment of the invention R³ is:

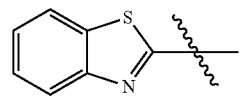 [SMILES: *c1nc2ccccc2s1]

which is substituted with one or more groups independently selected from (C₁-C₆)alkyl, and (C₃-C₈)cycloalkyl, wherein any $(C_1$-$C_6)$alkyl and $(C_3$-$C_8)$cycloalkyl is optionally substituted with one or more groups independently selected from halo and $(C_1$-$C_6)$alkyl that is optionally substituted with one or more groups independently selected from halo.

In one embodiment of the invention $R^3$ is:

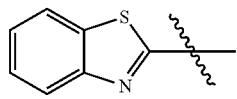 [SMILES: *c1nc2ccccc2s1]

which is substituted with one or more groups independently selected from trifluoromethyl, pentafluoroethyl, or 1-(trifluoromethyl)cyclopropyl.

In one embodiment of the invention $R^3$ is:

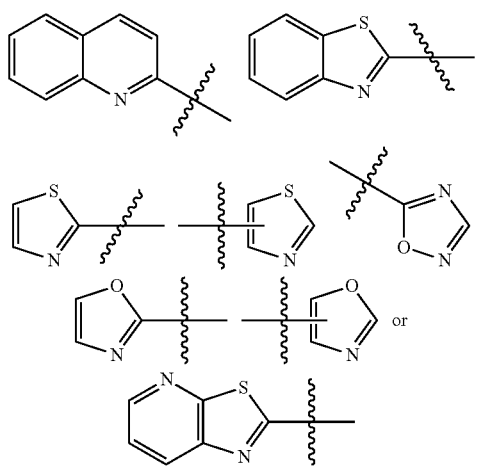

which is optionally substituted with one or more groups independently selected from $R^h$, halo, hydroxy, —$NR^eR^f$, —$CR^g$(=N)N($R^g$)$_2$, —$NR^gC$(=N)—N($R^g$)$_2$, —$NR^g$—C(=$NR^g$)$R^g$, $(C_1$-$C_6)$alkyl, and $(C_3$-$C_8)$cycloalkyl, wherein any $(C_1$-$C_6)$alkyl and $(C_3$-$C_8)$cycloalkyl is optionally substituted with one or more groups independently selected from halo, hydroxy, —$NR^eR^f$, —$CR^g$(=N)N($R^g$)$_2$, —$NR^gC$(=N)—N($R^g$)$_2$, —$NR^g$—C(=$NR^g$)$R^g$, and $(C_1$-$C_6)$alkyl that is optionally substituted with one or more groups independently selected from halo.

In one embodiment of the invention $R^3$ is:

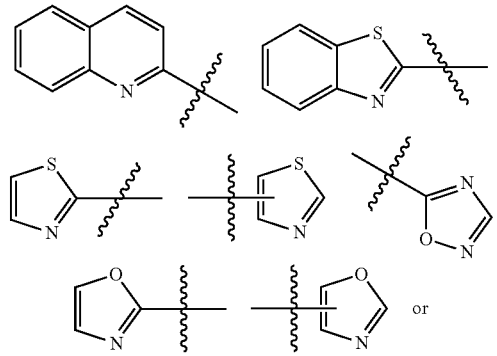

which is optionally substituted with one or more groups independently selected from $(C_1$-$C_6)$alkyl, and $(C_3$-$C_8)$cycloalkyl, wherein any $(C_1$-$C_6)$alkyl and $(C_3$-$C_8)$cycloalkyl is optionally substituted with one or more groups independently selected from halo, hydroxy, and $(C_1$-$C_6)$alkyl that is optionally substituted with one or more groups independently selected from halo.

In one embodiment of the invention $R^3$ is:

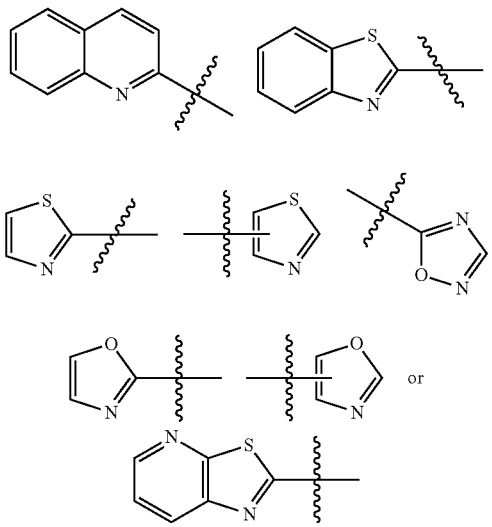

which is optionally substituted with one or more groups independently selected from trifluoromethyl, pentafluoroethyl, or 1-(trifluoromethyl)cyclopropyl.

In one embodiment of the invention:

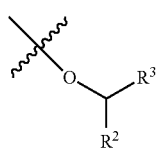

is selected from:

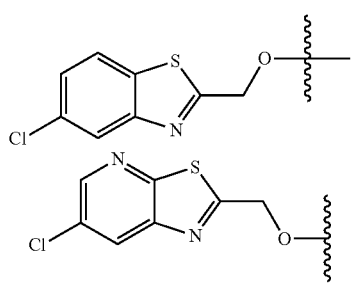

-continued
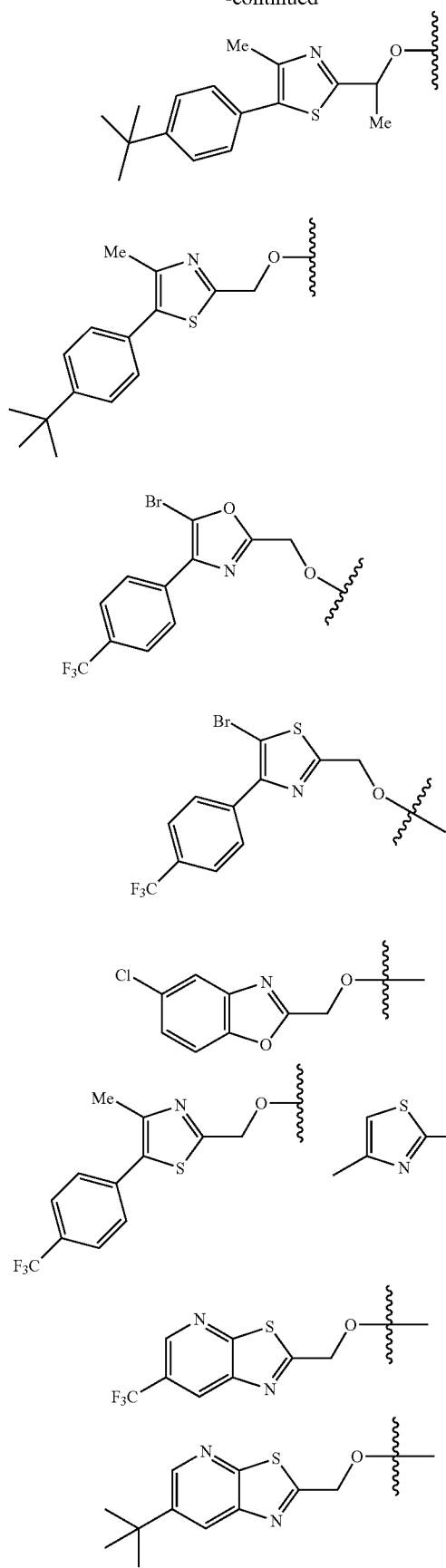
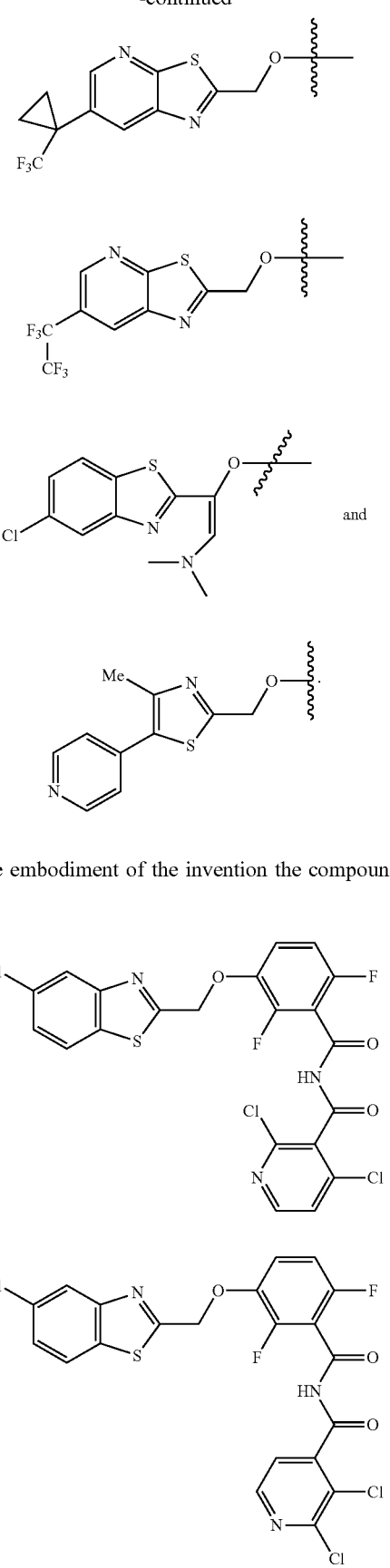
In one embodiment of the invention the compound is:
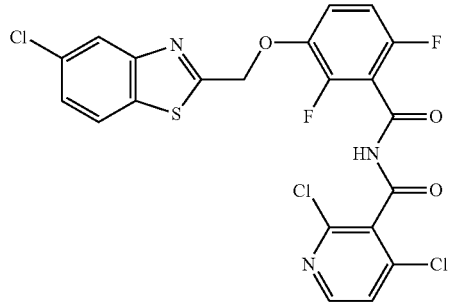 [SMILES: O=C(NC(=O)c1c(F)ccc(OCc2nc3cc(Cl)ccc3s2)c1F)c1c(Cl)ccnc1Cl]
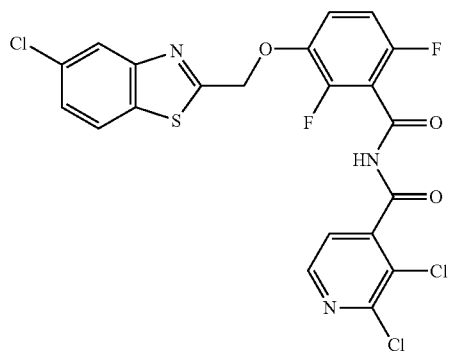 [SMILES: O=C(NC(=O)c1c(F)ccc(OCc2nc3cc(Cl)ccc3s2)c1F)c1ccnc(Cl)c1Cl]

25
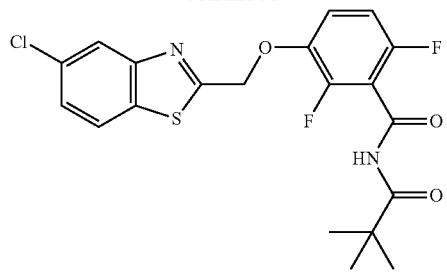 [SMILES: CC(C)(C)C(=O)NC(=O)c1c(F)ccc(OCc2nc3cc(Cl)ccc3s2)c1F]
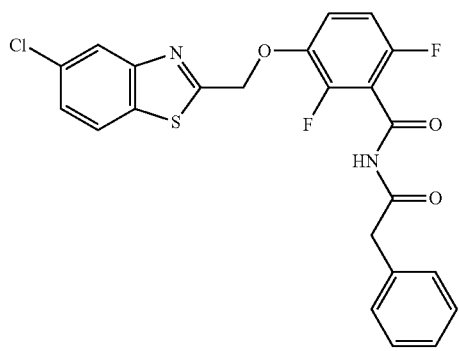 [SMILES: O=C(Cc1ccccc1)NC(=O)c1c(F)ccc(OCc2nc3cc(Cl)ccc3s2)c1F]
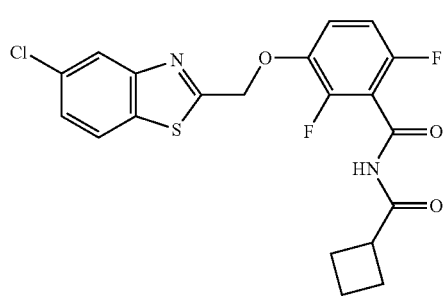 [SMILES: O=C(NC(=O)C1CCC1)c1c(F)ccc(OCc2nc3cc(Cl)ccc3s2)c1F]
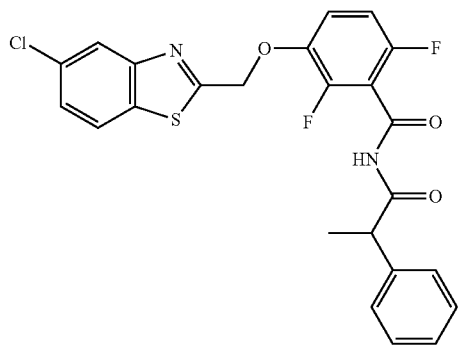 [SMILES: CC(C(=O)NC(=O)c1c(F)ccc(OCc2nc3cc(Cl)ccc3s2)c1F)c1ccccc1]
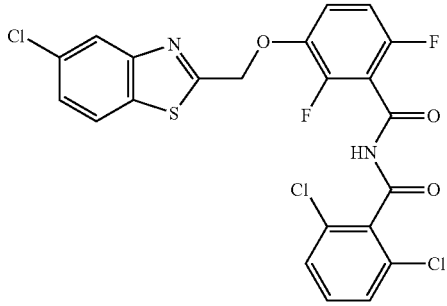 [SMILES: O=C(NC(=O)c1c(F)ccc(OCc2nc3cc(Cl)ccc3s2)c1F)c1c(Cl)cccc1Cl]
26
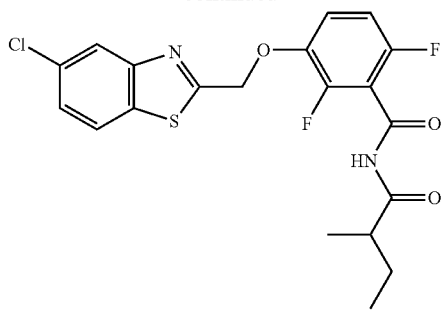
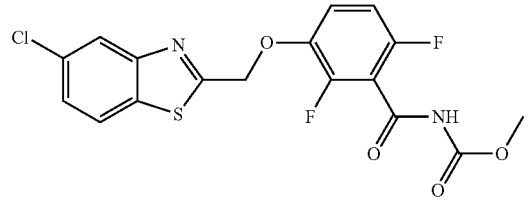
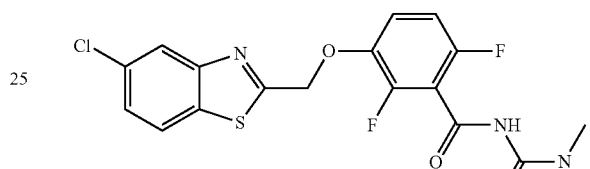
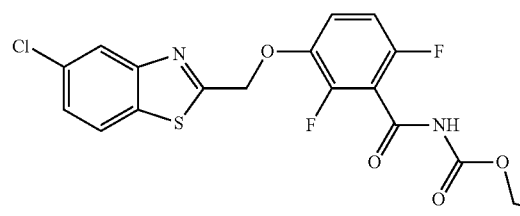
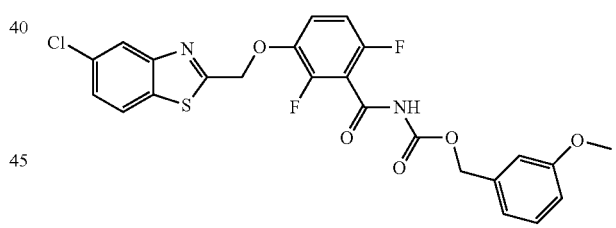
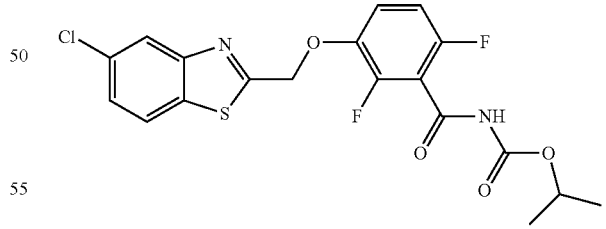
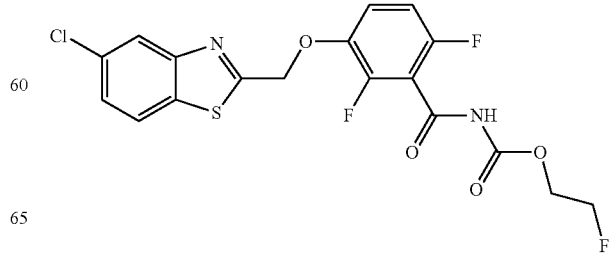

27
-continued
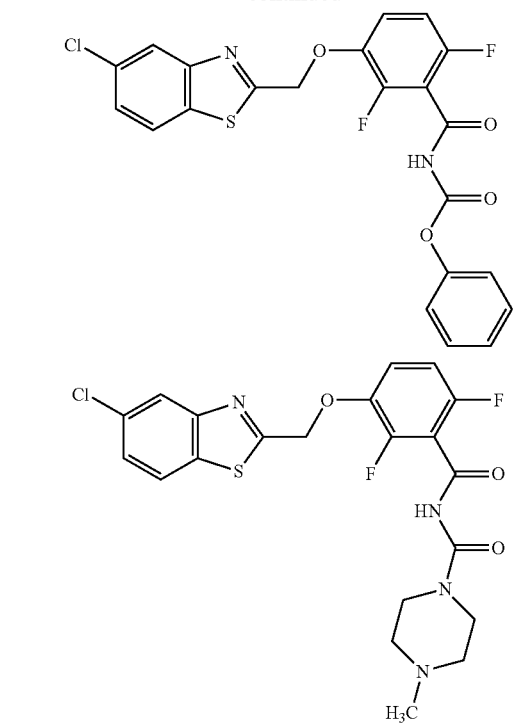
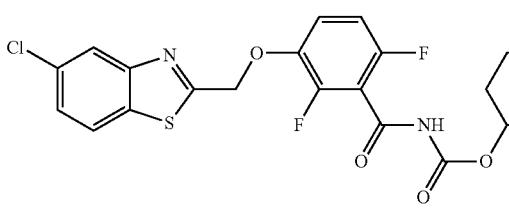
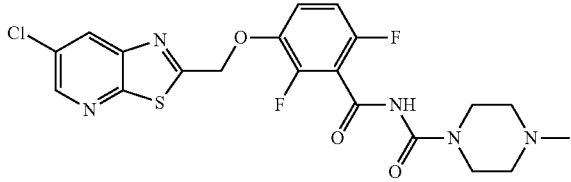 [SMILES: CN1CCN(C(=O)NC(=O)c2c(F)ccc(OCc3nc4cc(Cl)cnc4s3)c2F)CC1]
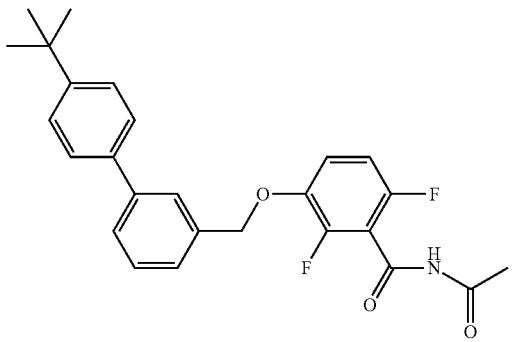 [SMILES: CC(=O)NC(=O)c1c(F)ccc(OCc2cccc(-c3ccc(C(C)(C)C)cc3)c2)c1F]
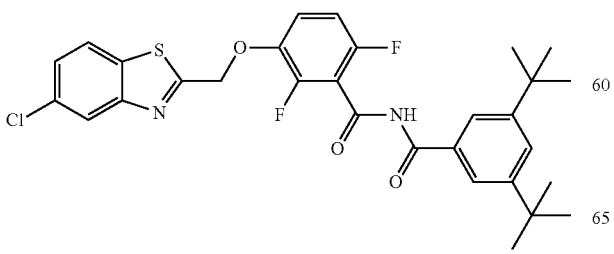
28
-continued
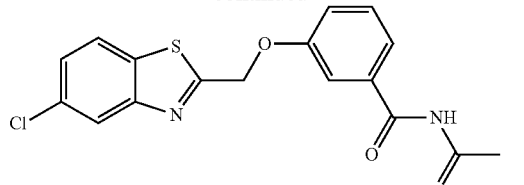
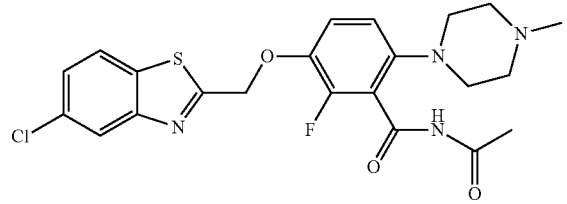 [SMILES: CC(=O)NC(=O)c1c(N2CCN(C)CC2)ccc(OCc2nc3cc(Cl)ccc3s2)c1F]
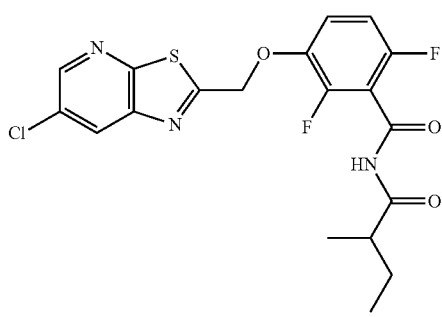 [SMILES: CCC(C)C(=O)NC(=O)c1c(F)ccc(OCc2nc3cc(Cl)cnc3s2)c1F]
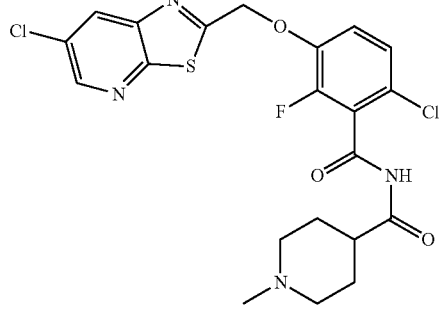
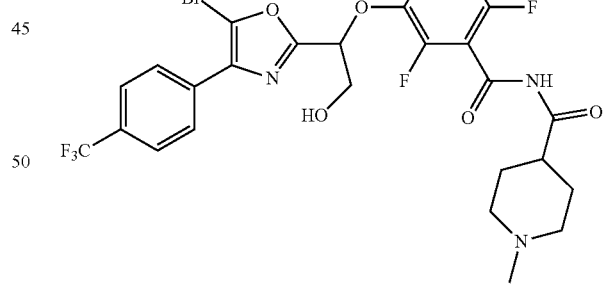
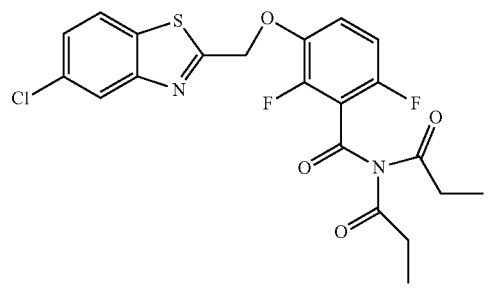

-continued
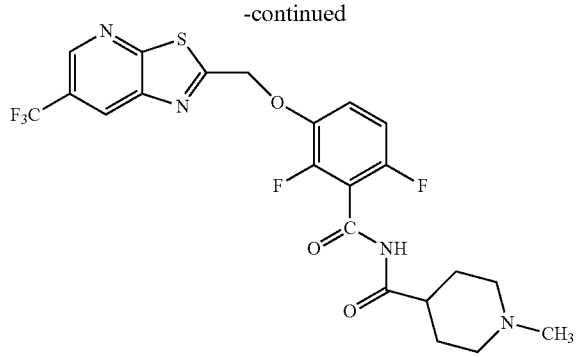
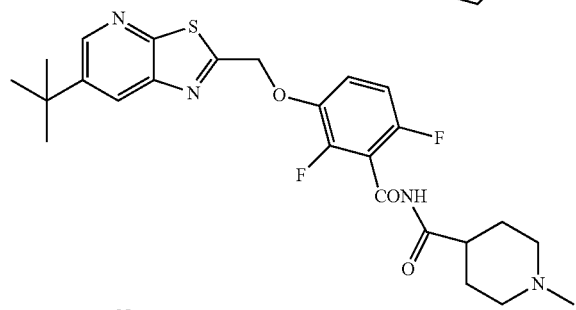
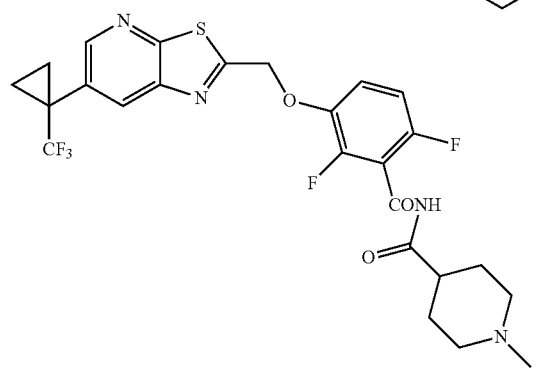
or a salt thereof.
In one embodiment of the invention the compound is:
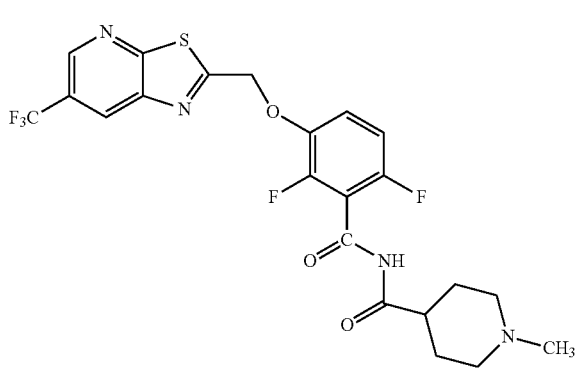 [SMILES: CN1CCC(C(=O)NC(=O)c2c(F)ccc(OCc3nc4cc(C(F)(F)F)cnc4s3)c2F)CC1]
-continued
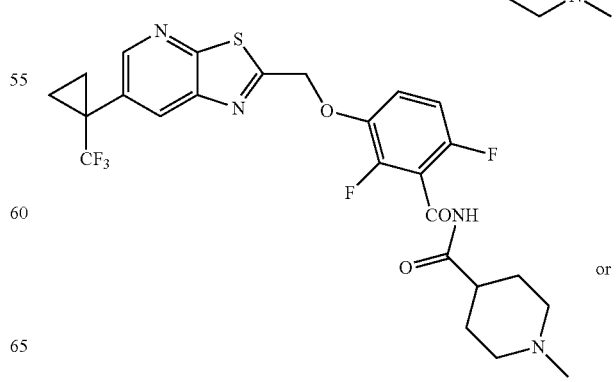
or a salt thereof.
In one embodiment of the invention the compound is:

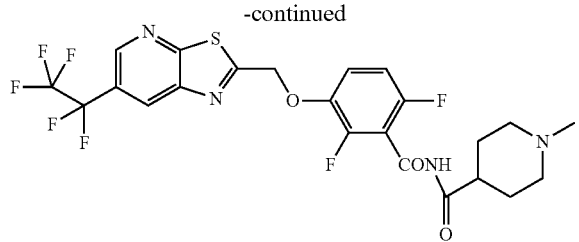

or a salt thereof.

In one embodiment of the invention the compound is:

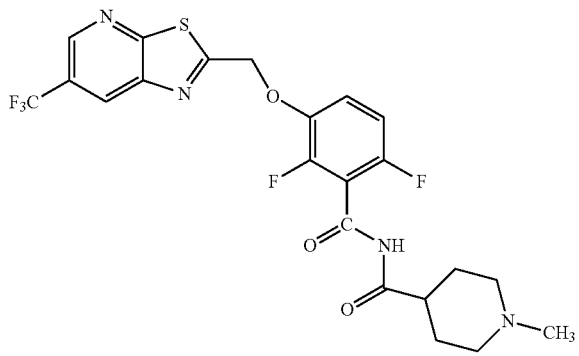

or a salt thereof.

In one embodiment each $R^h$ is independently selected from aryl and heteroaryl, wherein any aryl and heteroaryl of $R^h$ is optionally substituted with one or more groups independently selected from halo, hydroxy, —NR$^e$R$^f$, —CR$^g$(=N)N(R$^g$)$_2$, —NR$^g$C(=N)—N(R$^g$)$_2$, —NR$^g$—C(=NR$^g$)R$^g$ and (C$_1$-C$_6$)alkyl that is optionally substituted with one or more groups independently selected from hydroxy, halo, —NR$^e$R$^f$, —CR$^g$(=N)N(R$^g$)$_2$, —NR$^g$C(=N)—N(R$^g$)$_2$, and —NR$^g$—C(=NR$^g$)R$^g$.

In one embodiment each $R^h$ is independently selected from aryl and heteroaryl, wherein any aryl and heteroaryl of $R^h$ is optionally substituted with one or more groups independently selected from $R^m$.

In one embodiment each $R^h$ is independently selected from aryl and heteroaryl, wherein any aryl and heteroaryl of $R^h$ is substituted with one or more groups independently selected from $R^m$.

In one embodiment each $R^h$ is independently selected from aryl and heteroaryl, wherein any aryl and heteroaryl of $R^h$ is not substituted with one or more groups independently selected from $R^m$.

In one embodiment each $R^m$ is independently selected from (C$_1$-C$_6$)alkoxy that is optionally substituted with one or more groups independently selected from halo, oxo, and (C$_1$-C$_6$)alkoxy.

In one embodiment each $R^m$ is independently selected from (C$_1$-C$_6$)alkoxy that is optionally substituted with one or more groups independently selected from halo.

In one embodiment each $R^m$ is independently selected from trifluoromethoxy.

In one embodiment each $R^h$ is independently selected from aryl and heteroaryl, wherein any aryl and heteroaryl of $R^h$ is optionally substituted with one or more trifluoromethoxy groups.

In one embodiment of the invention $R^3$ is:

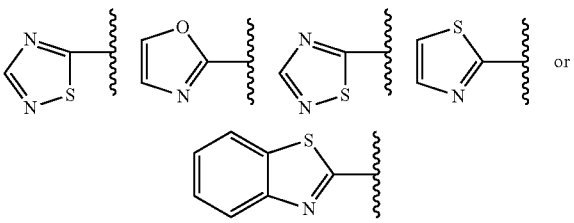

which is optionally substituted with one or more groups independently selected from $R^h$, halo, hydroxy, —NR$^e$R$^f$, —CR$^g$(=N)N(R$^g$)$_2$, —NR$^g$C(=N)—N(R$^g$)$_2$, —NR$^g$—C(=NR$^g$)R$^g$, (C$_1$-C$_6$)alkyl, and (C$_3$-C$_8$)cycloalkyl, wherein any (C$_1$-C$_6$)alkyl and (C$_3$-C$_8$)cycloalkyl is optionally substituted with one or more groups independently selected from halo, hydroxy, —NR$^e$R$^f$, —CR$^g$(=N)N(R$^g$)$_2$, —NR$^g$C(=N)—N(R$^g$)$_2$, —NR$^g$—C(=NR$^g$)R$^g$, and (C$_1$-C$_6$)alkyl that is optionally substituted with one or more groups independently selected from halo.

In one embodiment of the invention $R^3$ is:

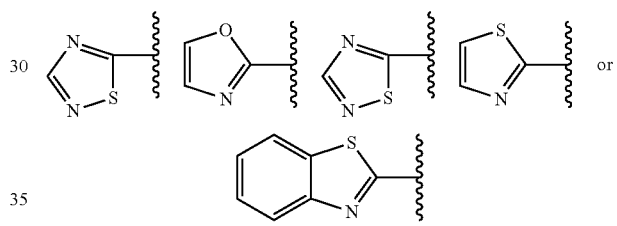

which is optionally substituted with one or more groups independently selected from $R^h$, halo, and (C$_1$-C$_6$)alkyl, wherein any (C$_1$-C$_6$)alkyl is optionally substituted with one or more groups independently selected from halo, hydroxy, —NR$^e$R$^f$, —CR$^g$(=N)N(R$^g$)$_2$, —NR$^g$C(=N)—N(R$^g$)$_2$, —NR$^g$—C(=NR$^g$)R$^g$, and (C$_1$-C$_6$)alkyl that is optionally substituted with one or more groups independently selected from halo.

In one embodiment of the invention:

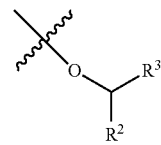

is selected from:

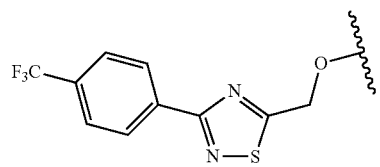

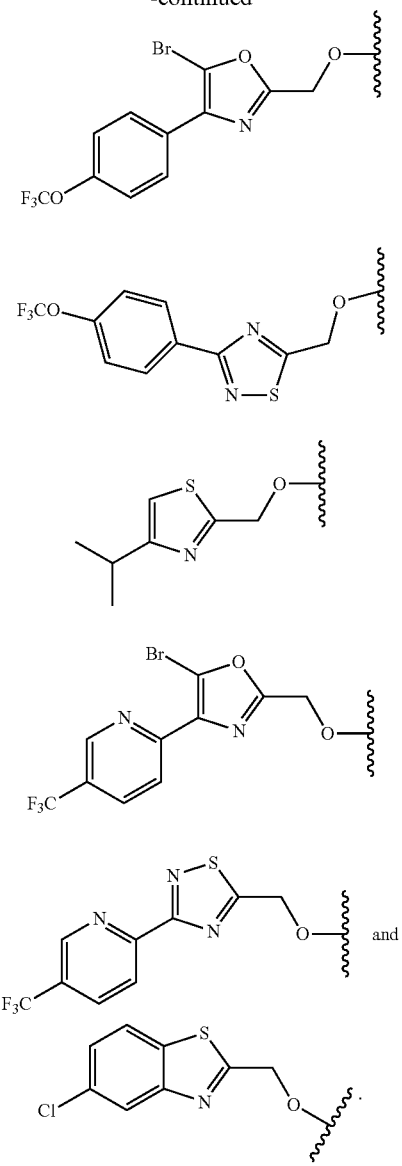
In one embodiment of the invention W is —NHC(=O)NHCH₃ or
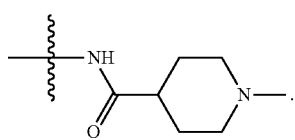
In one embodiment of the invention the compound is:
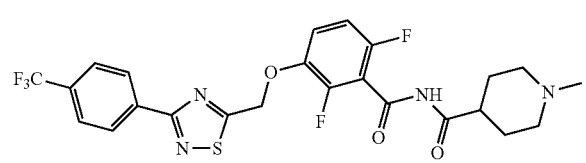 [SMILES: CN1CCC(C(=O)NC(=O)c2c(F)ccc(OCc3nc(-c4ccc(C(F)(F)F)cc4)ns3)c2F)CC1]
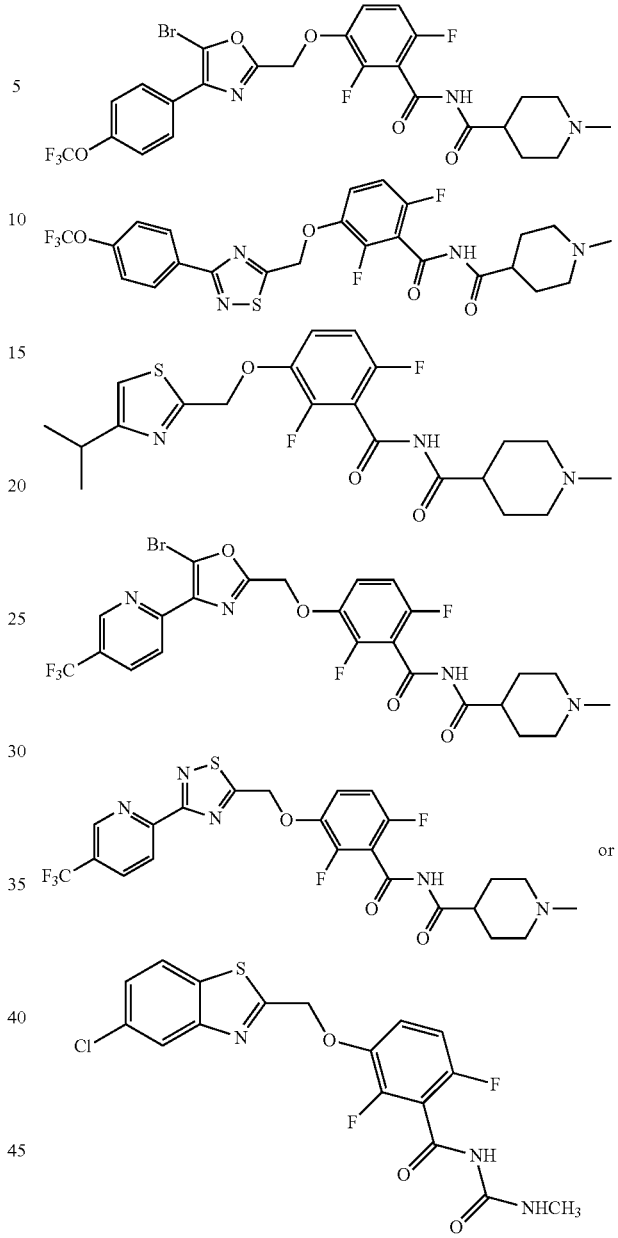
or a salt thereof.
In one embodiment of the invention the compound is not:
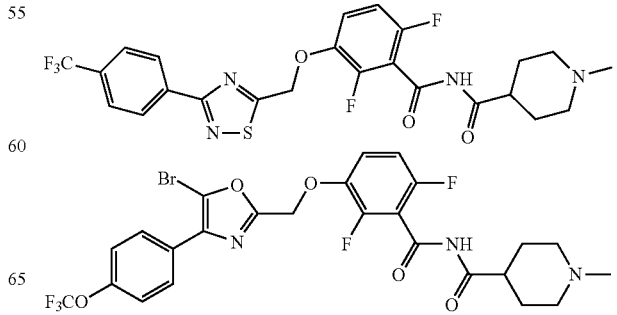

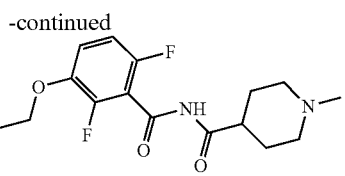

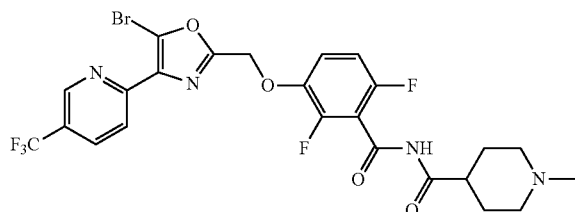

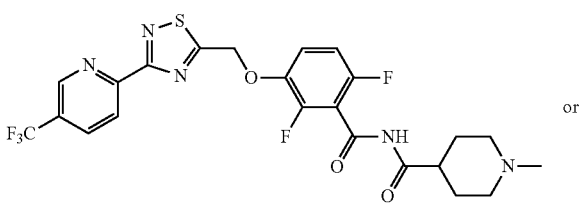

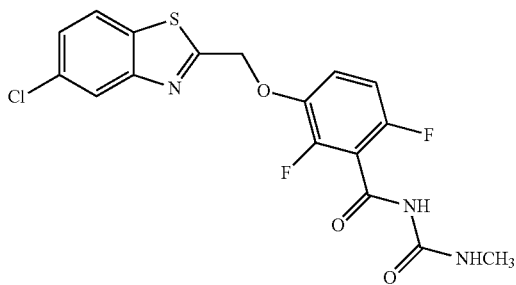 [SMILES: CNC(=O)NC(=O)c1c(F)ccc(OCc2nc3cc(Cl)ccc3s2)c1F]

or a salt thereof.

In one embodiment the invention provides a compound selected from compounds of formula I and salts thereof having a minimal inhibitory concentration against MSSA of less than about 8 µg/ml (see Test C below).

In one embodiment the invention provides a compound selected from compounds of formula I and salts thereof having a minimal inhibitory concentration against MSSA of less than about 4 µg/ml.

In one embodiment the invention provides a compound selected from compounds of formula I and salts thereof having a minimal inhibitory concentration against MSSA of less than about 2 µg/ml.

In one embodiment the invention provides a compound selected from compounds of formula I and salts thereof having a minimal inhibitory concentration against MSSA of less than about 1 µg/ml.

In one embodiment the invention provides a compound selected from compounds of formula I and salts thereof having a minimal inhibitory concentration against MSSA of less than about 0.5 µg/ml.

In one embodiment the invention provides a compound of formula I or a salt thereof that increases the survival percentage by at least 25% at 72 hours when administered at a non-lethal dose against MSSA in Test D below.

In one embodiment the invention provides a compound of formula I or a salt thereof that increases the survival percentage by at least 50% at 72 hours when administered at a non-lethal dose against MSSA in Test D below.

In one embodiment the invention provides a compound of formula I or a salt thereof that increases the survival percentage by at least 75% at 72 hours when administered at a non-lethal dose against MSSA in Test D below.

Generally, compounds of formula I as well as synthetic intermediates that can be used for preparing compounds of formula I can be prepared as illustrated in the following General Methods and Schemes. It is understood that variable groups shown below (e.g. $R^1$, $R^2$, and $R^3$) can represent the final corresponding groups present in a compound of formula I or that these groups can represent groups that can be converted to the final corresponding groups present in a compound of formula I at a convenient point in a synthetic sequence. For example, the variable groups can contain one or more protecting groups that can be removed at a convenient point in a synthetic sequence to provide the final corresponding groups in the compound of formula I.

General Method for N'-substituted N-(2-aminoacetyl) amides and 2-substituted N-(acyl)amides.

General Method for the preparation of substituted N-(1-aminomethylidene)benzamides.

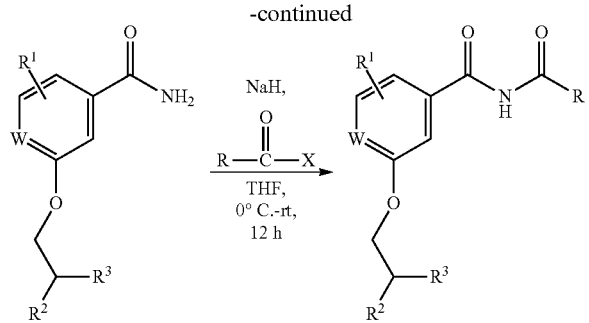

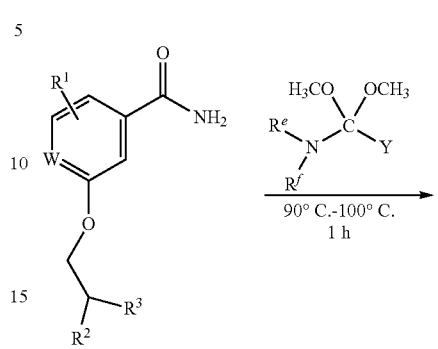

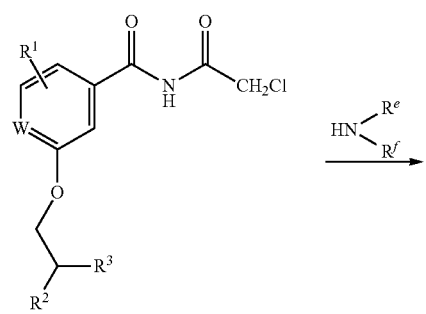

Treatment of the requisite benzamide intermediate with amide acetals, such as N,N-dimethylformamide dimethoxy acetal or N,N-dimethylacetamide dimethoxy acetal, provides the desired N-(1-aminomethylidene)benzamide derivatives.

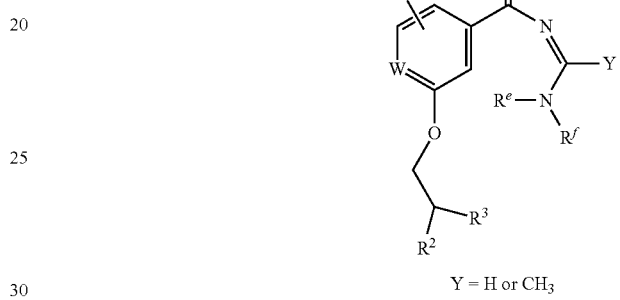

Reaction of the benzamide with an activated acylating agents, such as an acid chloride, anhydride, or mixed anhydride will provide varied N-(acetyl)amides. Alternatively, the use of chloroacetyl chloride provides the N-(2-chloroacetyl)amide, which can be treated with a variety of primary and secondary amines to give various N'substituted N-(2-aminoacetyl)amides.

Scheme 1. Method Used to Prepare N-(Acyl)benzamide Derivatives.

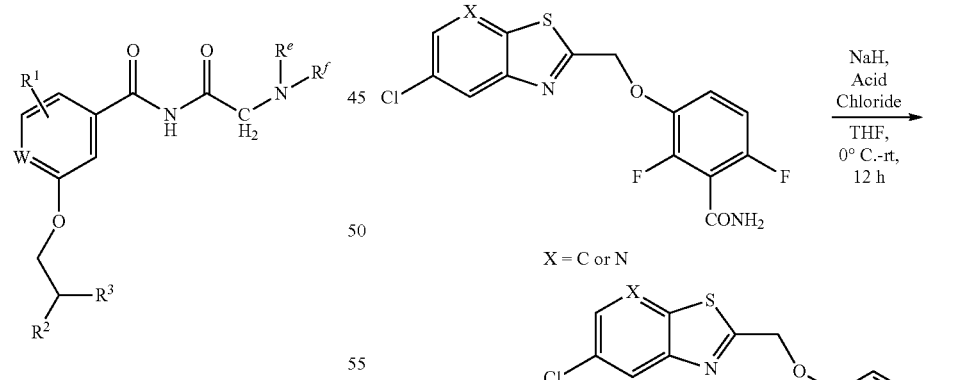

R = ethyl, propyl, cyclohexyl, phenyl etc

Scheme 2. Method Used to Prepare N-[2-(Imidazol-1-yl)acetyl]benzamide and N-[2-(4-Methyl-1-piperdinyl)acetyl]benzamide Derivatives.
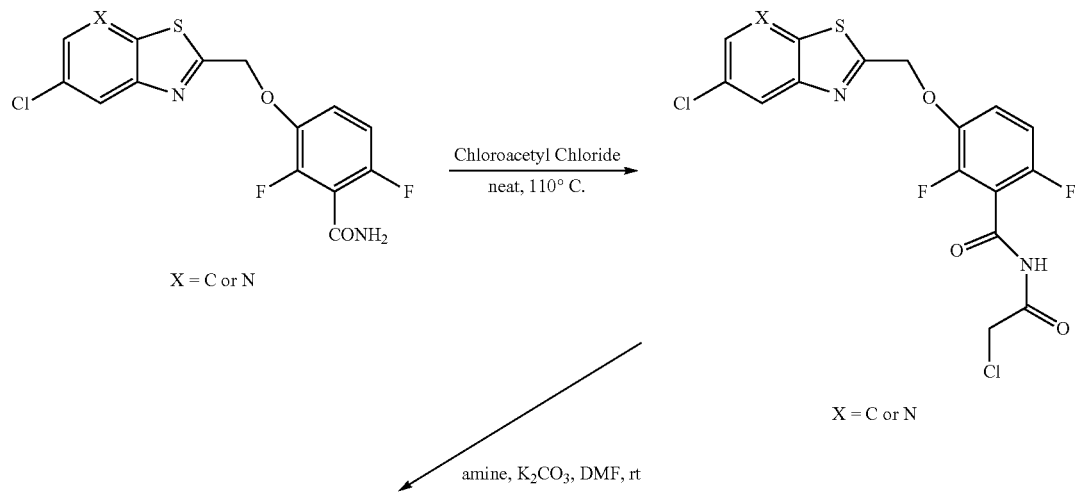
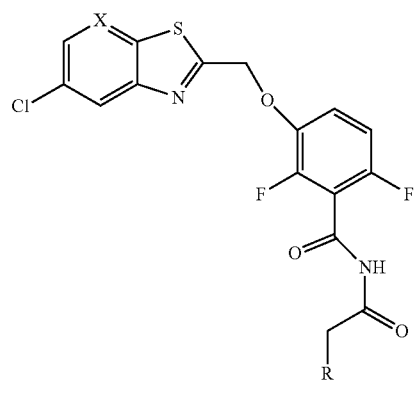
X = C or N
R = imidazole or 4-methyl piperidine
Scheme 3. Method Used to Prepare Substituted N-(1-Aminomethylidene)benzamides, N-(Formyl)benzamide and N-(Acetyl)benzamide Derivatives.
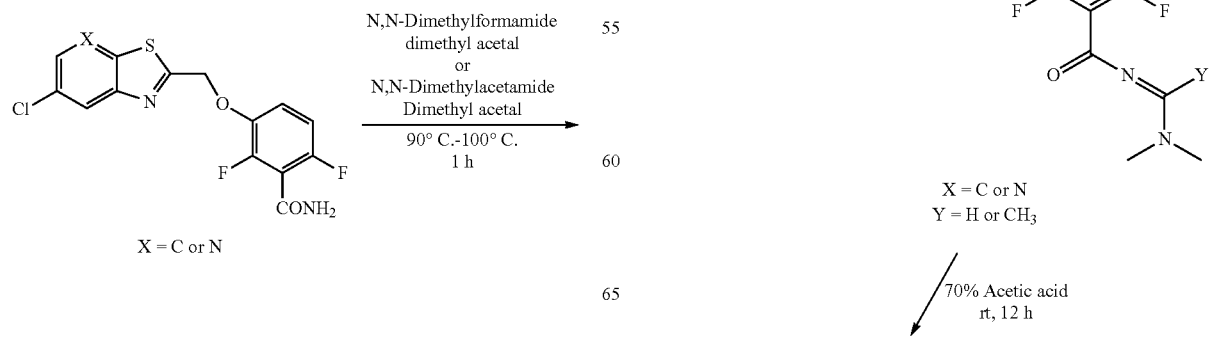

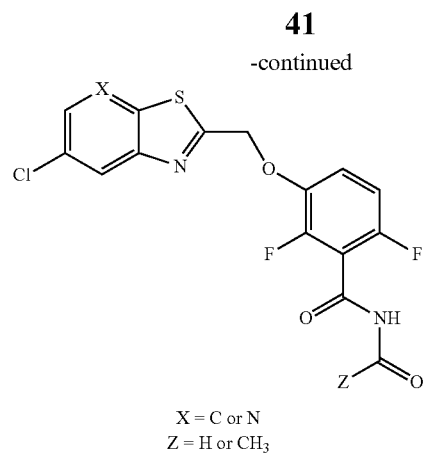
X = C or N
Z = H or CH₃
Scheme 4. Methods for the preparation of t-butyl-,
1-(trifluoromethyl)cyclopropyl-, and pentafluoroethyl-
substituted analogs from bromo or iodo thiazolo[5,4-b]pyridine.
a) Preparation of t-butyl substituted derivatives
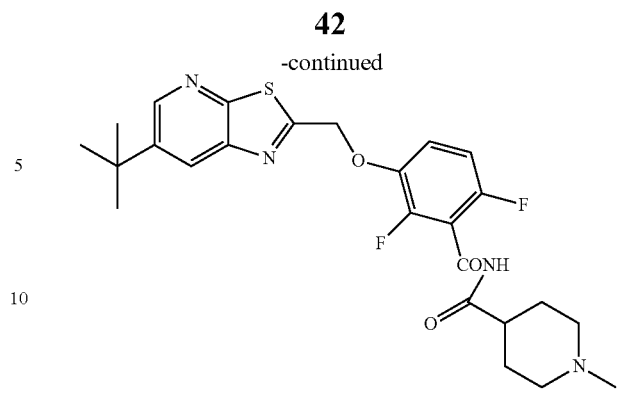
b) Preparation of 1-(trifluoromethyl)cyclopropyl substituted derivatives
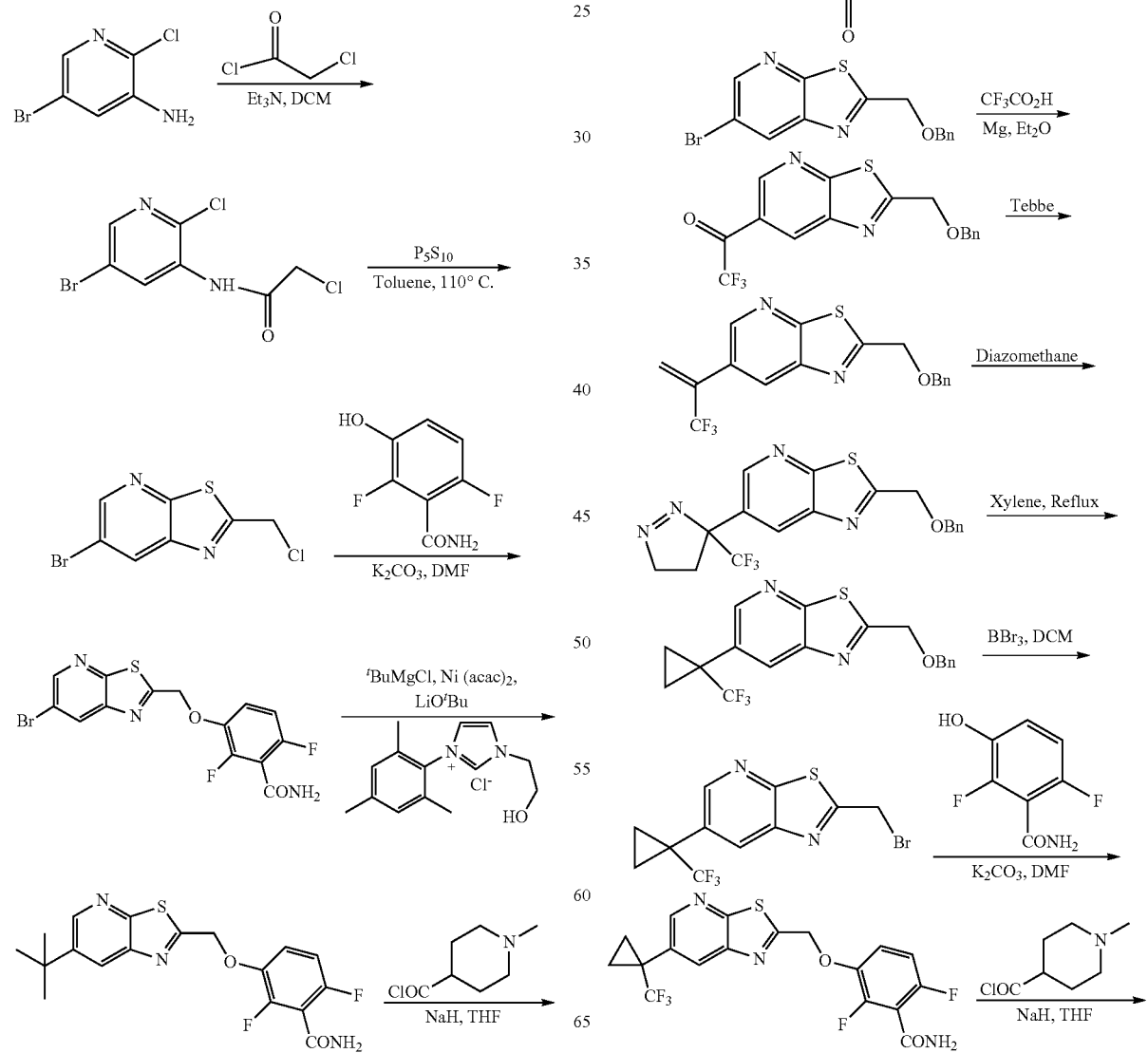

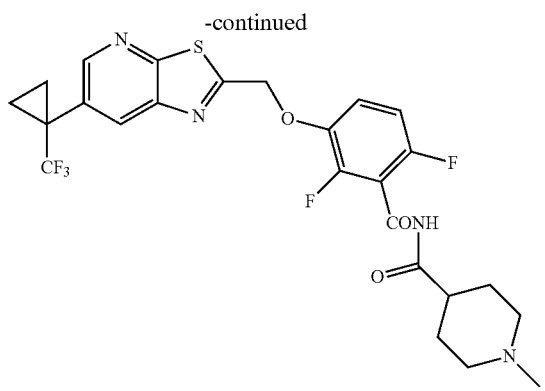

c) Preparation of pentafluoroethyl substituted derivatives.

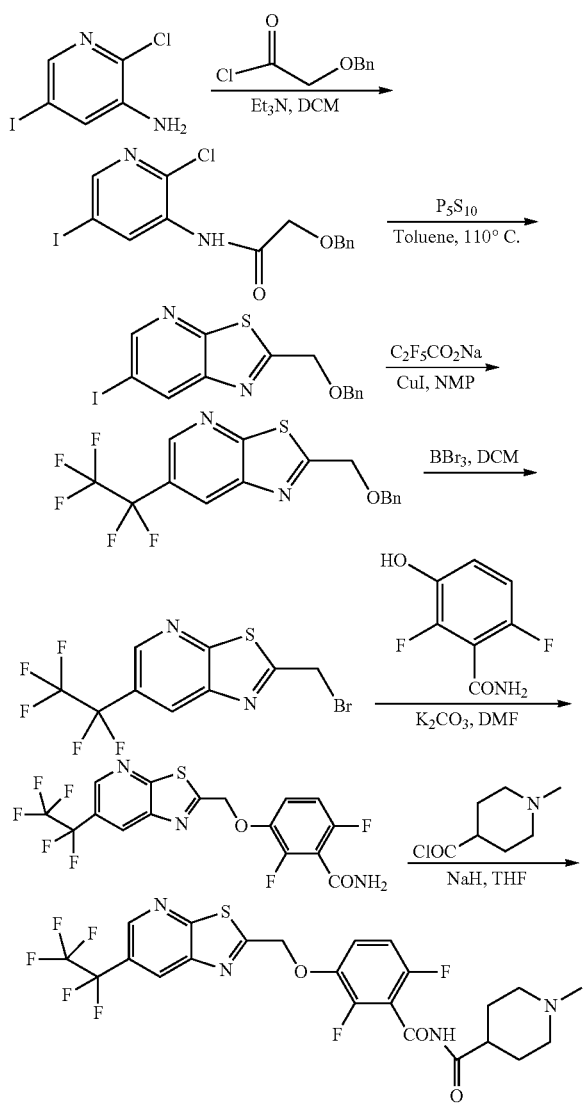

The compounds of the present invention inhibit bacterial Z-ring formation, which is essential for cytokinesis. Since the Z-ring serves as the scaffold for recruitment of all other proteins that comprise the divisome complex, inhibition of Z-ring formation by the compounds of the present invention also results in a corresponding inhibition of divisome protein recruitment.

The compounds of the invention are useful to treat bacterial infections including infections by Gram-positive and Gram-negative bacterial strains, and multiple drug-resistant bacterial strains. For treatment of Gram-negative bacterial strains as well as Gram-positive bacterial strains, the compounds of the invention may be administered in combination with an efflux pump inhibitor to enhance antibacterial activity. See Lomovskaya, O., et al., *Nature Reviews (Drug Discovery)*, 2007, 6, 56-65; and Handzlik, J. et al., *Antibiotics,* 2013, 2, 28-45.

In one embodiment compounds of the present invention may be administered as a composition used to treat and/or prevent a bacterial infection wherein the bacterial cell uses polymerized FtsZ protein, or a homolog thereof, to facilitate cytokinesis. To this end, compounds of the present invention may be administered to treat Staph Infections, Tuberculosis, Urinary Tract Infections, Meningitis, Enteric Infections, Wound Infections, Acne, Encephalitis, Skin Ulcers, Bed Sores, Gastric and Duodenal Ulcers, Eczema, Periodontal disease, Gingivitis, Halitosis, Anthrax, Tularemia, Endocarditis, Prostatitis, Osteomyelitis, Lyme Disease, Pneumonia, or the like.

The compositions can, if desired, also contain other active therapeutic agents, such as a narcotic, a non-steroid anti-inflammatory drug (NSAID), an analgesic, an anesthetic, a sedative, a local anesthetic, a neuromuscular blocker, an anti-cancer, other antimicrobial (for example, an aminoglycoside, an antifungal, an antiparasitic, an antiviral, a carbapenem, a cephalosporin, a flurorquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an anti-tussive, an anti-emetic, an anti-ulcer, a laxative, an anticoagulant, an erythropieitin (for example, epoetin alpha), a filgrastim (for example, G-CSF, Neupogen), a sargramostim (GM-CSF, Leukine), an immunization, an immunoglobulin, an immunosuppressive (for example, basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, an anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), a cytokine, or any combination thereof.

It will be appreciated that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

It will also be appreciated by those skilled in the art that certain compounds of the invention can exist in more than one tautomeric form. For example, a substituent of formula —NH—C(=O)H in a compound of formula (I) could exist in tautomeric form as —N=C(OH)H. The present invention encompasses all tautomeric forms of a compound of formula I as well as mixtures thereof that can exist in equilibrium with non-charged and charged entities depending upon pH, which possess the useful properties described herein.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, fumarate, benzoate, ascorbate, α-ketoglutarate, and α-glycerophosphate. Suitable inorganic salts may also be formed, including hydrochloride, sulfate, nitrate, bicarbonate, and carbonate salts. Salts may be obtained using standard procedures well known in the art, for example by reacting a sufficiently basic compound such as an amine with a suitable acid affording the corresponding anion. Alkali metal (for example, sodium, potassium or lithium) or alkaline earth metal (for example calcium) salts of carboxylic acids can also be made.

Pharmaceutically suitable counterions include pharmaceutically suitable cations and pharmaceutically suitable anions that are well known in the art. Examples of pharmaceutically suitable anions include, but are not limited to those described above (e.g. physiologically acceptable anions) including $Cl^-$, $Br^-$, $I^-$, $CH_3SO_3^-$, $H_2PO_4^-$, $CF_3SO_3^-$, $p$-$CH_3C_6H_4SO_3^-$, citrate, tartrate, phosphate, malate, fumarate, formate, or acetate.

It will be appreciated by those skilled in the art that a compound of the invention comprising a counterion can be converted to a compound of the invention comprising a different counterion. Such a conversion can be accomplished using a variety of well known techniques and materials including but not limited to ion exchange resins, ion exchange chromatography and selective crystallization.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes. For oral administration the compounds can be formulated as a solid dosage form with or without an enteric coating.

Thus, the present compounds may be systemically administered, e.g., orally, in combination with a pharmaceutically acceptable vehicle such as an inert diluent, excipient or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 90% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The active compound may also be administered intravenously or intramuscularly by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.1 to about 500 mg/kg, e.g., from about 0.5 to about 400 mg/kg of body weight per day, such as 1 to about 250 mg per kilogram body weight of the recipient per day.

The compound is conveniently formulated in unit dosage form; for example, containing 0.5 to 500 mg, 1 to 400 mg, or 0.5 to 100 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The antibacterial activity of a compound of the invention can be determined using a method like Test A described below.

Test A. Antibacterial Assay.

Antibacterial activity can be determined as per Clinical and Laboratory Standards Institute (CLSI) guidelines using a broth microdilution assay in which log-phase bacteria are grown at 37° C. in appropriate medium containing two-fold serial dilutions of a compound to yield final concentrations ranging from 256 to 0.06 µg/mL. For determination of minimal inhibitory concentration (MIC) values, bacterial growth is monitored after 24 to 48 hours by measuring optical density at 600 nm. MIC values reflect the minimal compound concentrations at which bacterial growth is completely inhibited. Data for representative compounds of the invention are shown in Table 1.

TABLE 1

Minimal Inhibitory Concentrations against MSSA for representative compounds of the Invention

| Example Number | Drug Structure | MIC MSSA µg/mL | MIC MRSA µg/mL |
| --- | --- | --- | --- |
| 1 | | 0.25 | 0.125 |
| 1b | | 0.125 | 0.125 |

TABLE 1-continued
Minimal Inhibitory Concentrations against MSSA for representative compounds of the Invention
| Example Number | Drug Structure | MIC MSSA µg/mL | MIC MRSA µg/mL |
|---|---|---|---|
| 2 | 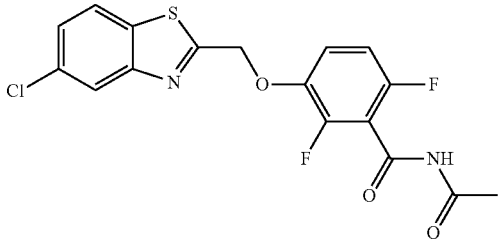 | 2.0 | 4.0 |
| 2a | 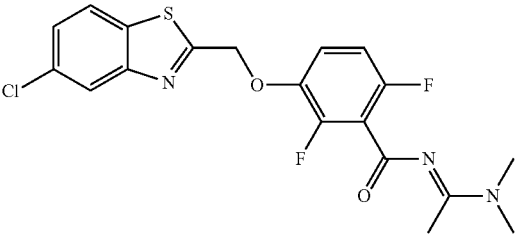 | 2.0 | 4.0 |
| 3 | 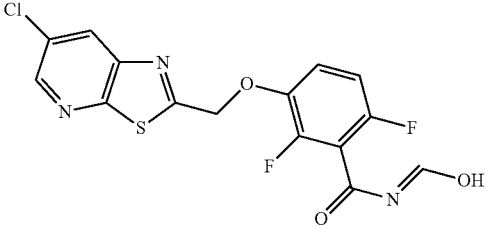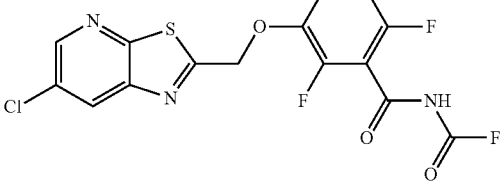 | 0.5 | 0.5 |
| 3b | 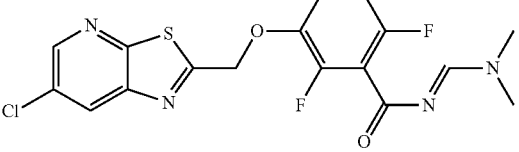 | 0.5 | 1.0 |
| 4 | 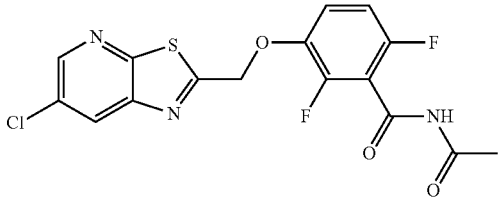 | 2.0* | — |

TABLE 1-continued

Minimal Inhibitory Concentrations against MSSA for representative compounds of the Invention

| Example Number | Drug Structure | MIC MSSA µg/mL | MIC MRSA µg/mL |
|---|---|---|---|
| 4a | | 4.0 | 4.0 |
| 5 | | 2.0** | 2.0** |
| 6 | | 0.5** | 1.0** |
| 7 | | 0.5** | — |
| 8 | | 0.5 | 0.5 |
| 9 | | 0.5** | — |
| 10 | | 0.125 | 0.25 |

TABLE 1-continued

Minimal Inhibitory Concentrations against MSSA for representative compounds of the Invention

| Example Number | Drug Structure | MIC MSSA µg/mL | MIC MRSA µg/mL |
|---|---|---|---|
| 11 | | 0.5 | 1.0 |
| 12 | | 0.125 | 0.25 |
| 13 | | 4.0* | — |
| 14 | | 2.0* | — |
| 15 | | 8.0 | 8.0 |
| 16 | | 2.0 | 2.0 |

TABLE 1-continued

Minimal Inhibitory Concentrations against MSSA for representative compounds of the Invention

| Example Number | Drug Structure | MIC MSSA μg/mL | MIC MRSA μg/mL |
|---|---|---|---|
| 17 | | 2.0 | 4.0 |
| 18 | | >64.0 | >64.0 |
| 19 | | >64.0 | 4.0 |
| 20 | | >64.0 | 4.0 |
| 21 | | >64.0 | 2.0 |

TABLE 1-continued

Minimal Inhibitory Concentrations against MSSA for representative compounds of the Invention

| Example Number | Drug Structure | MIC MSSA μg/mL | MIC MRSA μg/mL |
|---|---|---|---|
| 22 | | 0.5 | 2.0 |
| 23 | | >64.0 | 2.0 |
| 24 | | >64.0 | >64.0 |
| 25 | | >64.0 | 2.0 |
| 26 | | >64.0 | 8.0 |

TABLE 1-continued

Minimal Inhibitory Concentrations against MSSA for representative compounds of the Invention

| Example Number | Drug Structure | MIC MSSA µg/mL | MIC MRSA µg/mL |
|---|---|---|---|
| 27 | | >64.0 | >64.0 |
| 28 | | >64.0 | 8.0 |
| 29 | | 8.0 | 32 |
| 30 | | >64.0 | 2.0 |
| 31 | | >64.0 | 4.0 |

TABLE 1-continued

Minimal Inhibitory Concentrations against MSSA for representative compounds of the Invention

| Example Number | Drug Structure | MIC MSSA μg/mL | MIC MRSA μg/mL |
|---|---|---|---|
| 32 | | 4.0 | 4.0 |
| 33 | | >64.0 | >64.0 |
| 34 | | 32.0 | 4.0 |
| 35 | | 0.25 | 2.0 |
| 36 | | >64.0 | >64.0 |

TABLE 1-continued

Minimal Inhibitory Concentrations against MSSA for representative compounds of the Invention

| Example Number | Drug Structure | MIC MSSA µg/mL | MIC MRSA µg/mL |
|---|---|---|---|
| 37 | | >64.0 | 8.0 |
| 38 | | >64.0 | >64.0 |
| 39 | | >64.0 | >64.0 |
| 40 | | >64.0 | 2.0 |
| 41 | | 4.0 | 8.0 |

TABLE 1-continued

Minimal Inhibitory Concentrations against MSSA for representative compounds of the Invention

| Example Number | Drug Structure | MIC MSSA μg/mL | MIC MRSA μg/mL |
|---|---|---|---|
| 42 | | 1.0 | 16.0 |
| 43 | | 64.0 | 64.0 |
| 44 | | 0.5 | 2.0 |
| 45 | | 0.5 | 4.0 |
| 46 | | 1.0 | 4.0 |

TABLE 1-continued

Minimal Inhibitory Concentrations against MSSA for representative compounds of the Invention

| Example Number | Drug Structure | MIC MSSA µg/mL | MIC MRSA µg/mL |
|---|---|---|---|
| 47 | (structure) | 0.0625 | 1.0 |
| 48 | (structure) | 8.0 | 8.0 |
| 49 | (structure) | 2.0 | 16.0 |
| 50 | (structure) | 1.0 | 4.0 |
| 51 | (structure) | >64.0 | >64.0 |

*MIC determined in the presence of 50% mouse serum
**MIC values may be lower as solubility and aggregate formation may reduce observed activity.

The impact of a compound of the invention on the dynamics of bacterial FtsZ polymerization can be determined using a method like Test B described below.

Test B. FtsZ Polymerization Assay.

Compound-induced alteration in the dynamics of FtsZ polymerization can be tested using a turbidity assay with purified FtsZ protein. Upon addition of GTP, FtsZ self-associates to form polymeric structures that scatter light at 340 nm to a greater extent than the monomeric protein. The impact of the compounds of the invention on the polymerization dynamics of FtsZ can be detected by an increase or decrease in the extent of GTP-induced light scattering (as determined by corresponding changes in optical density at 340 nm) relative to that observed in the absence of compound. Quantitation of the overall extent of light scattering as a function of compound concentration provides an indication of the potency of that compound at altering the dynamics of FtsZ polymerization.

The impact of a compound of the invention on FtsZ Z-ring formation in bacteria can be determined using a method like Test C described below.

Test C. FtsZ Z-Ring Assay.

The impact of a compound on FtsZ Z-ring formation can be determined using a strain of *Bacillus subtilis* (FG347) that expresses a green fluorescent protein (GFP)-ZapA fusion protein upon induction with xylose. ZapA is known to associate with FtsZ Z-rings in *B. subtilis* and, thus, serves as a marker for Z-ring formation. In this assay, log-phase FG347 bacteria are treated with differing concentrations of compound for time periods ranging from 1 to 6 hours. At each time point, aliquots are taken from each culture and then viewed with a fluorescence microscope. In the absence of compound, the bacteria exhibit green fluorescent foci (Z-rings) localized at mid-cell. By contrast, bacteria treated with a compound that disrupts Z-ring formation do not exhibit the green fluorescent Z-rings at mid-cell and are typically associated with an elongated, filamentous phenotype.

The in vivo efficacy of a compound of the invention can be determined using a method like Test D described below.

Test D. In Vivo Efficacy in the Mouse Peritonitis or Mouse Septicemia Model.

Antistaphylococcal efficacy in vivo was assessed in a mouse peritonitis model of systemic infection with *S. aureus* ATCC 19636 (MSSA) or ATCC 43300 (MRSA). These studies were conducted in full compliance with the standards established by the US National Research Council's Guide for the Care and Use of Laboratory Animals, and were approved by the Institutional Animal Care and Use Committee (IACUC) of Rutgers University. Groups of 4-6 female Swiss-Webster mice with an average weight of 25 g were infected intraperitoneally with a lethal inoculum of each bacterial strain in saline. The inoculum of *S. aureus* ATCC 43300 contained $1.0 \times 10^8$ CFUs/mL of bacteria, while the inoculum of *S. aureus* ATCC 19636 contained $0.8 \times 10^7$ CFUs/mL of bacteria. All the inocula also contained porcine mucin (Sigma-Aldrich, Co.) at a (w/v) percentage of 1.5% (in ATCC 19636 inocula) or 5% (in the ATCC 43300 inoculum). The differing compositions of the inocula of these *S. aureus* strains were selected based on the virulence of each strain, with MSSA ATCC 19636 being the more virulent strain and MRSA ATCC 43300 being the less virulent strain.

All compound and vehicle intravenous (i.v.) administrations were by tail vein injection, with 17 being formulated at 2.0 mg/mL and 44 being formulated at both 2.0 and 3.0 mg/ml in 10 mM citrate (pH 2.6).

In the MSSA ATCC 19636 experiments, the first dose of compound was administered 10 minutes after infection, with subsequent doses being administered at 12-minute intervals thereafter unless otherwise noted. In the MRSA studies, the first dose of compound was administered one hour after infection, with subsequent doses being administered at 12-minute intervals thereafter unless otherwise indicated.

The body temperatures of all mice were monitored for a period of 5 days after infection. Body temperatures were recorded at the Xiphoid process using a noninvasive infrared thermometer (Braintree Scientific, Inc., Braintree, Mass.). Infected mice with body temperatures ≤28.9° C. were viewed as being unable to recover from the infection and were euthanized.

| Compound 17 | | ATCC 19636 (MSSA) $0.8 \times 10^7$ cells in 1.5% mucin | | Survival (%) | | |
|---|---|---|---|---|---|---|
| Route | n/Group | Frequency | Total Dose/ Mouse (mg) | 24 Hrs | 48 Hrs | 72 Hrs |
| i.v. | 6 | 1x[a] | 0.6 | 0 | 0 | 0 |
| i.v | 6 | 2x[a] | 1.2 | 0 | 0 | 0 |
| i.v | 6 | 3x[a] | 1.8 | 33.3 | 33.3 | 33.3 |
| i.v | 6 | 4x[a] | 2.4 | 83.3 | 83.3 | 83.3 |
| Vehicle Only i.v. | 6 | 4x[a] | — | 0 | 0 | 0 |
| p.o. | 4 | 1x[b] | 0.8 | 0 | 0 | 0 |
| p.o. | 4 | 2x[b] | 1.6 | 0 | 0 | 0 |
| p.o. | 6 | 4x | 3.2 | 83.3 | 83.3 | 83.3 |
| p.o. | 6 | 4x[b] | 3.2 | 100 | 100 | 100 |
| Vehicle Only p.o. | 6 | 4x | — | 0 | 0 | 0 |

[a]The first ($t_1$) i.v. dose was administered immediately prior to infection; subsequent doses were administered 15 minutes following the first ($t_1$) dose.
[b]The first ($t_1$) p.o. dose was administered 5 minutes prior to infection; subsequent doses were administered 15 minutes apart following infection.

| Compound 17 | | ATCC 43300 (MRSA) $1.0 \times 10^8$ cells in 5% mucin | | Survival (%) | | |
|---|---|---|---|---|---|---|
| Route | n/Group | Frequency | Total Dose/ Mouse (mg) | 24 Hrs | 48 Hrs | 72 Hrs |
| p.o. | 6 | 3x[c] | 2.4 | 66.7 | 16.7 | 16.7 |
| p.o. | 6 | 6x[c] | 4.8 | 100 | 100 | 100 |
| p.o | 6 | 6x | 4.8 | 83.3 | 50 | 50 |
| p.o | 6 | 6x[d] | 4.8 | 100 | 100 | 100 |
| Vehicle Only p.o. | 6 | 6x | — | 0 | 0 | 0 |

[c]The first ($t_1$) p.o. dose was administered 5 minutes prior to infection; subsequent doses were administered 12 minutes apart following infection.
[d]The first ($t_1$) p.o. dose was administered 10 minutes post-infection; subsequent doses were administered 12 minutes apart.

| Compound 44 | | ATCC 19636 (MSSA) $0.8 \times 10^7$ cells in 1.5% mucin | | Survival (%) | | |
|---|---|---|---|---|---|---|
| Route | n/Group | Frequency | Total Dose/ Mouse (mg) | 24 Hrs | 48 Hrs | 72 Hrs |
| i.v. | 6 | 1x | 0.9 | 83.3 | 83.3 | 83.3 |
| i.v | 6 | 2x | 1.8 | 100 | 100 | 100 |
| Vehicle Only i.v. | 6 | 1x | — | 0 | 0 | 0 |
| p.o. | 6 | 1x | 0.8 | 50 | 50 | 50 |
| p.o. | 6 | 2x | 1.6 | 100 | 100 | 100 |
| p.o | 6 | 3x | 2.4 | 100 | 100 | 100 |

| p.o | 4 | 4x | 3.2 | 100 | 100 | 100 |
| Vehicle Only p.o. | 6 | 3x | — | 0 | 0 | 0 |

The invention will now be illustrated by the following non-limiting examples.

EXAMPLES

Example 1

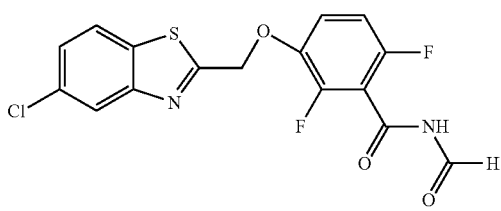 [SMILES: O=CNC(=O)c1c(F)ccc(OCc2nc3cc(Cl)ccc3s2)c1F]

3-((5-Chlorobenzo[d]thiazol-2-yl)methoxy)-N-((dimethylamino)methylene)-2,6-difluorobenzamide (50 mg, 0.122 mmol) was treated with 70% acetic acid (1 ml) at room temperature for 12 hours. Water is added and the resulting solid was collected by filtration and was washed with cold water to afford the product as white solid (39 mg, 83% yield). $^1$H NMR (DMSO-d6, 300 MHz) δ: 9.2 (s, 1H), 8.21 (d, J=9.0 Hz, 1H), 8.14 (s, 1H), 7.54 (m, 2H), 7.25 (m, 1H), 5.76 (s, 2H).

The requisite intermediates were prepared as follows.
a. Preparation of Compound

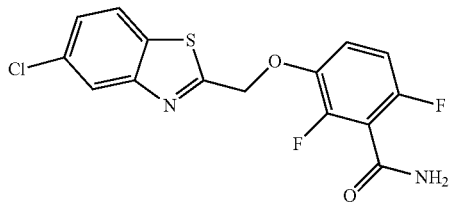 [SMILES: NC(=O)c1c(F)ccc(OCc2nc3cc(Cl)ccc3s2)c1F]

Prepared as described in the literature method by Haydon, Bennett, et al., *J. Med. Chem.*, 2010, 53, 3927.
b. Preparation of Compound

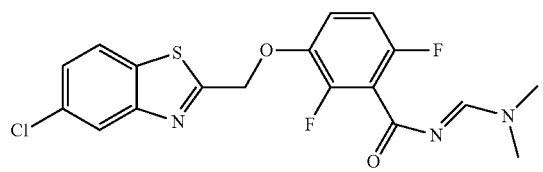 [SMILES: CN(C)/C=N/C(=O)c1c(F)ccc(OCc2nc3cc(Cl)ccc3s2)c1F]

A suspension of 3-((5-chlorobenzo[d]thiazol-2-yl)methoxy)-2,6-difluorobenzamide (110 mg, 0.31 mmol) in 2.0 mL of dimethylformamide dimethyl acetal was stirred at 100° C. for 1 hour. The excess dimethylformamide dimethyl acetal was removed under vacuum and the resulting solid was triturated with diethyl ether to afford the pure product as white solid (90 mg, 71% yield). $^1$H NMR (300 MHz, CDCl$_3$) δ: 8.62 (s, 1H), 8.01 (s, 1H), 7.82 (d, J=8.4 Hz, 1H), 7.4 (m, 1H), 7.07-6.99 (m, 1H), 6.81 (m, 1H), 5.49 (s, 2H), 3.21 (s, 3H), 3.16 (s, 3H).

Example 2

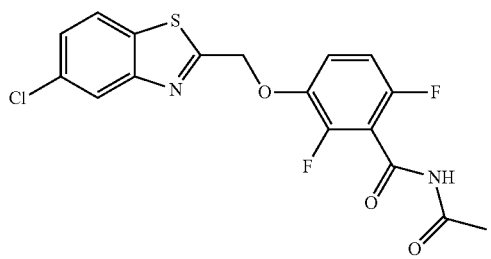 [SMILES: CC(=O)NC(=O)c1c(F)ccc(OCc2nc3cc(Cl)ccc3s2)c1F]

3-((5-Chlorobenzo[d]thiazol-2-yl)methoxy)-N-(1-(dimethylamino)ethylidene)-2,6-difluorobenzamide (50 mg, 0.118 mmol) was treated with 70% acetic acid (1.0 ml) at room temperature for 12 hours. Water is added and the resulting solid was collected by filtration and was washed with cold water to afford the product as white solid (37 mg, 79% yield). $^1$H NMR (DMSO-d6, 300 MHz) δ: 8.65 (d, J=8.4 Hz, 1H), 8.57 (s, 1H), 7.98 (d, J=9.0 Hz, 1H), 7.92 (m, 1H), 7.62 (m, 1H), 6.17 (s, 2H), 2.65 (s, 3H).

The requisite intermediates were prepared as follows.
a. Preparation of Compound

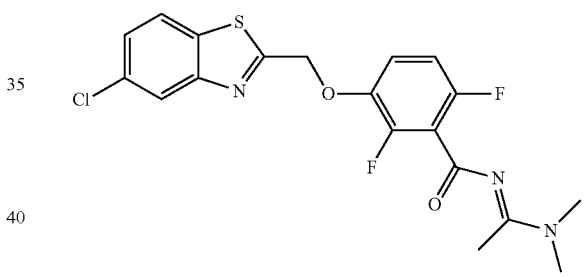

A suspension of 3-((5-chlorobenzo[d]thiazol-2-yl)methoxy)-2,6-difluorobenzamide (110 mg, 0.31 mol) in 1.5 mL of N,N-Dimethylacetamide Dimethyl acetal was stirred at 90° C. for 1 hour. The excess dimethylacetamide dimethyl acetal was removed under vacuum and the resulting solid was triturated with diethyl ether to afford the pure product as off white solid (50 mg, 79% yield). $^1$H NMR (300 MHz, CDCl$_3$) δ: 8.01 (s, 1H), 7.82 (d, J=8.7 Hz, 1H), 7.39 (dd, J=6.6, 1.8 Hz, 1H), 6.99 (m, 1H), 6.8 (m, 1H), 5.48 (s, 2H), 3.17 (s, 3H), 3.14 (s, 3H), 2.44 (s, 3H).

Example 3

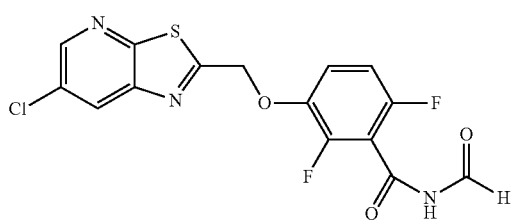 [SMILES: O=CNC(=O)c1c(F)ccc(OCc2nc3cc(Cl)cnc3s2)c1F]

3-((6-Chlorothiazolo[5,4-b]pyridin-2-yl)methoxy)-N-((dimethylamino)methylene)-2,6-difluorobenzamide (100 mg, 0.243 mmol) was treated with 70% acetic acid (1.0 ml) at room temperature for 12 hours. Water is added and the resulting solid was collected by filtration and was washed with cold water to afford the product as white solid (67 mg, 71% yield). $^1$H NMR (DMSO-d6, 300 MHz) δ: 9.19 (bs, 1H), 8.76-8.70 (m, 2H), 7.60 (m, 1H), 7.28 (m, 1H), 5.79 (s, 2H).

The requisite intermediates were prepared as follows.
a. Preparation of Compound

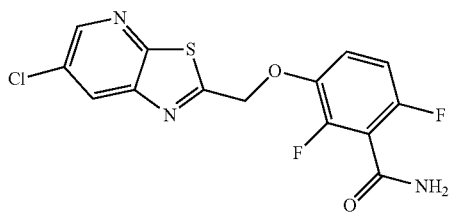 [SMILES: NC(=O)c1c(F)ccc(OCc2nc3cc(Cl)cnc3s2)c1F]

Prepared as described in the literature method by Haydon, Stokes, et al., Science, 2008, 321, 1673, Haydon, Bennett, et al., *J. Med. Chem.*, 2010, 53, 3927, Sorto, et al., *J. Org. Chem.*, 2010, 75, 7946, and Ding et al., Synlett, 2012, 23, 1039.
b. Preparation of Compound

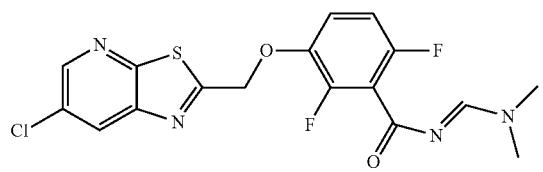 [SMILES: CN(C)/C=N/C(=O)c1c(F)ccc(OCc2nc3cc(Cl)cnc3s2)c1F]

A suspension of 3-((6-chlorothiazolo[5,4-b]pyridin-2-yl)methoxy)-2,6-difluorobenzamide (20 mg, 0.06 mmol) in 1.0 mL of dimethylformamide dimethyl acetal was stirred at 90° C. for 1 hour. The excess dimethylformamide dimethyl acetal was removed under vacuum and the resulting solid was triturated with diethyl ether to afford the pure product as off white solid (10 mg, 45% yield). $^1$H NMR (300 MHz, CDCl$_3$) δ: 8.63 (s, 1H), 8.57 (d, J=2.4 Hz, 1H), 7.05 (m, 1H), 6.92 (m, 1H), 5.47 (s, 2H), 3.22 (s, 3H), 3.16 (s, 3H).

Example 4

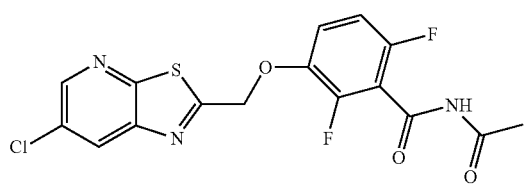 [SMILES: CC(=O)NC(=O)c1c(F)ccc(OCc2nc3cc(Cl)cnc3s2)c1F]

3-((6-Chlorothiazolo[5,4-b]pyridin-2-yl)methoxy)-N-(1-(dimethylamino)ethylidene)-2,6-difluorobenzamide (36 mg, 0.08 mmol) was treated with 70% acetic acid (0.5 ml) at room temperature for 12 hours. Water is added and the resulting solid was collected by filtration and was washed with cold water to afford the product as off white solid (25 mg, 89% yield). $^1$H NMR (300 MHz, CDCl$_3$) δ: 8.58 (d, J=2.4 Hz, 1H), 8.24 (d, J=2.1 Hz, 1H), 7.26-7.18 (m, 1H), 6.97-6.90 (m, 1H), 5.50 (s, 2H), 2.55 (s, 3H).

The requisite intermediate was prepared as follows.
a. Preparation of Compound

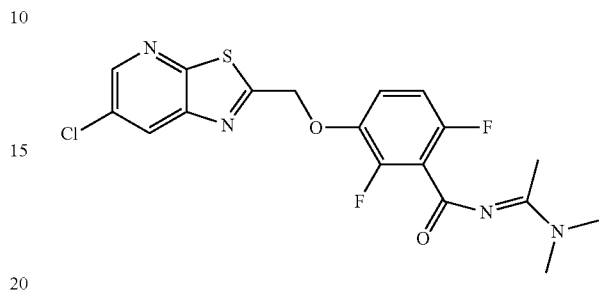

A suspension of 3-((6-chlorothiazolo[5,4-b]pyridin-2-yl)methoxy)-2,6-difluorobenzamide (100 mg, 0.28 mmol) in 1.0 mL of N,N-dimethylacetamide dimethyl acetal was stirred at 90° C. for 1 hour. The excess dimethylacetamide dimethyl acetal was removed under vacuum and the resulting solid was triturated with diethyl ether to afford the pure product as light yellow solid (95 mg, 79% yield). $^1$H NMR (300 MHz, CDCl$_3$) δ: 8.56 (s, 1H), 8.22 (s, 1H), 6.99 (m, 1H), 6.8 (m, 1H), 5.48 (s, 2H), 3.17 (s, 3H), 3.17 (s, 3H), 2.45 (s, 3H).

Example 5

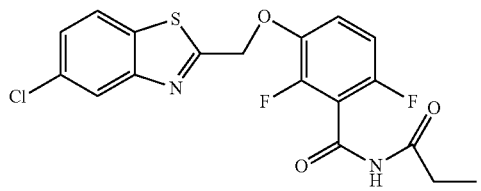 [SMILES: CCC(=O)NC(=O)c1c(F)ccc(OCc2nc3cc(Cl)ccc3s2)c1F]

In a round bottom flask 3-((5-chlorobenzo[d]thiazol-2-yl)methoxy)-2,6-difluorobenzamide (35 mg, 0.1 mmol) was dissolved in 2 ml of dry THF, and the solution was cooled to 0° C. under nitrogen. This was followed by portion wise addition of NaH (8 mg, 0.2 mmol, 60% dispersion in mineral oil). The mixture was stirred at 0° C. for 10 minutes and at room temperature for 45 minutes. The mixture was cooled to 0° C., and a solution of propionyl chloride (8 μl, 0.1 mmol) in 1 ml of THF was added dropwise. The resulting reaction mixture was stirred at 0° C. for 10 minutes and at room temperature for 4 hours. After completion of the reaction, it was quenched by the addition of few drops of 1N HCl, and diluted with ethyl acetate. The organic phase was separated, washed successively with sat. NaHCO$_3$, brine and dried. The solvent was removed in vacuo, and the resulting residue was purified by ISCO using 20% EtOAc in hexane as the elutant to afford the pure product as white solid (13 mg, 32% yield). $^1$H NMR (300 MHz, CDCl$_3$) δ: 8.23 (s, 1H), 8.04 (s, 1H), 7.85 (d, J=8.4 Hz, 1H), 7.44 (d, J=9.0 Hz, 1H), 7.22 (m, 1H), 6.93 (m, 1H), 5.54 (s, 2H), 2.89 (qt, J=7.2 Hz, 2H), 1.27-1.16 (m, 3H).

Example 6

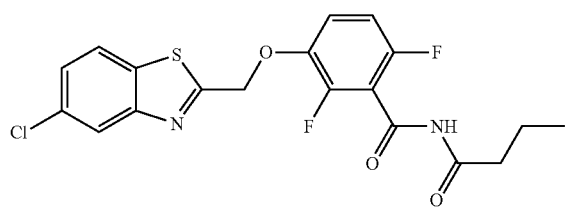 [SMILES: CCCC(=O)NC(=O)c1c(F)ccc(OCc2nc3cc(Cl)ccc3s2)c1F]

In a round bottom flask 3-((5-chlorobenzo[d]thiazol-2-yl)methoxy)-2,6-difluorobenzamide (55 mg, 0.155 mmol) was dissolved in 3 ml of dry THF, and the solution was cooled to 0° C. under nitrogen. This was followed by portion wise addition of NaH (13 mg, 0.310 mmol, 60% dispersion in mineral oil). The mixture was stirred at 0° C. for 10 minutes and at room temperature for 1 hour. The mixture was cooled to 0° C., and a solution of butyryl chloride (0.016 ml, 0.155 mmol) in 1 ml of THF was added dropwise. The resulting reaction mixture was stirred at 0° C. for 10 minutes and at room temperature for overnight. After completion of the reaction, it was quenched by the addition of few drops of 1N HCl, and diluted with ethyl acetate. The organic phase was separated, washed successively with sat. NaHCO$_3$, brine and dried. The solvent was removed in vacuo, and the resulting residue was purified by ISCO using 40% EtOAc in hexane as the elutant to afford the desired product as white solid (20 mg, 31% yield). $^1$H NMR (300 MHz, CDCl$_3$) δ: 8.24 (s, 1H), 8.05 (s, 1H), 7.86 (d, J=8.7 Hz, 1H), 7.45 (d, J=9.0 Hz, 1H), 7.22 (m, 1H), 6.93 (m, 1H), 5.54 (s, 2H), 2.84 (m, 2H), 1.75 (m, 2H), 1.04 (m, 3H).

Example 7

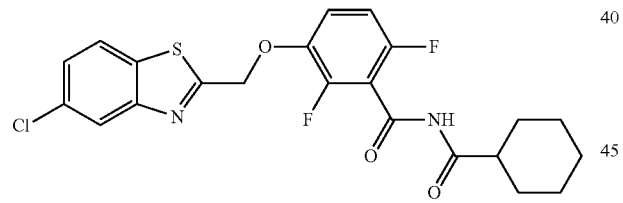

In a round bottom flask 3-((5-chlorobenzo[d]thiazol-2-yl)methoxy)-2,6-difluorobenzamide (35 mg, 0.1 mmol) was dissolved in 2 ml of dry THF, and the solution was cooled to 0° C. under nitrogen. This was followed by portion wise addition of NaH (12 mg, 0.3 mmol, 60% dispersion in mineral oil). The mixture was stirred at 0° C. for 10 minutes and at room temperature for 30 minutes. The mixture was cooled to 0° C., and a solution of cyclohexanecarbonyl chloride (0.013 ml, 0.1 mmol) in 1 ml of THF was added dropwise. The resulting reaction mixture was stirred at 0° C. for 10 minutes and at room temperature for 12 hours. After completion of the reaction, it was quenched by the addition of few drops of 1N HCl, and diluted with ethyl acetate. The organic phase was separated, washed successively with sat. NaHCO$_3$, brine and dried. The solvent was removed in vacuo, and the resulting residue was purified by ISCO using 20% EtOAc in hexane to afford desired product as yellow solid (16 mg, 35% yield). $^1$H NMR (300 MHz, CDCl$_3$) δ: 8.27 (s, 1H), 8.03 (d, J=2.1 Hz, 1H), 7.84 (d, J=8.7 Hz, 1H), 7.43 (dd, J=6.9, 2.1 Hz, 1H), 7.23-7.15 (m, 1H), 6.93-6.87 (m, 1H), 5.53 (s, 2H), 2.80 (m, 1H), 2.20-1.23 (m, 10H).

Example 8

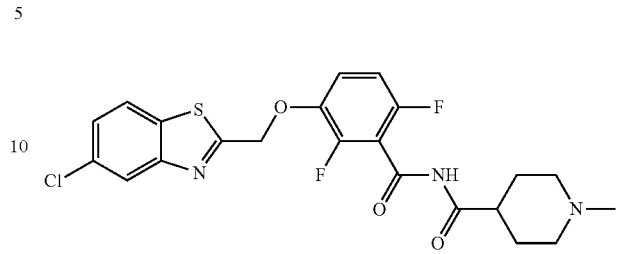

In a round bottom flask 3-((5-chlorobenzo[d]thiazol-2-yl)methoxy)-2,6-difluorobenzamide (25 mg, 0.07 mmol) was dissolved in 2.0 ml of dry THF, and the solution was cooled to 0° C. under nitrogen. This was followed by portionwise addition of NaH (11 mg, 0.24 mmol, 60% dispersion in mineral oil). The mixture was stirred at 0° C. for 10 minutes and at room temperature for 30 minutes. The mixture was cooled to 0° C., and a solution of acyl chloride 8a (28 mg, 0.14 mmol) in 1 ml of THF was added dropwise. The resulting reaction mixture was stirred at 0° C. for 10 minutes and at room temperature overnight. After completion of the reaction, it was quenched by the addition of few drops of 1N NaOH, and diluted with ethyl acetate. The organic phase was separated, washed successively with sat. NaHCO$_3$, brine and dried. The solvent was removed in vacuo, and the resulting residue was purified by ISCO using 10% MeOH in CH$_2$Cl$_2$+1% NH$_4$OH to afford yellow solid (16 mg, 36% yield). $^1$H NMR (300 MHz, CDCl$_3$) δ: 8.01 (d, J=2.1 Hz, 1H), 7.82 (d, J=8.7 Hz, 1H), 7.40 (dd, J=6.6, 1.8 Hz, 1H), 7.25-7.14 (m, 1H), 6.93-6.87 (m, 1H), 5.51 (s, 2H), 2.94-2.85 (m, 3H), 2.28 (s, 3H), 2.09-1.69 (m, 6H).

The requisite intermediate was prepared as follows.

a. Preparation of Compound

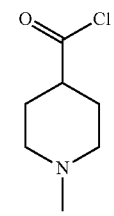

N-Methylisonipecotic acid hydrochloride (0.5 g) was dissolved in dry SOCl$_2$ (1.5 mL) The mixture was then heated at 80° C. for 2 hours under argon. Cooling and evaporation to dryness afforded a yellow solid which was used without further purification.

Example 9

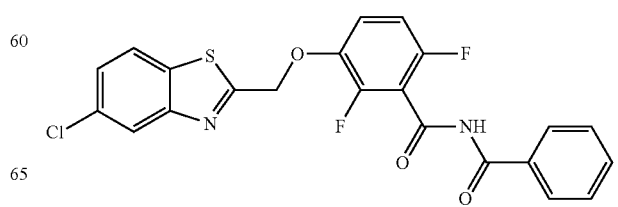

In a round bottom flask 3-((5-chlorobenzo[d]thiazol-2-yl)methoxy)-2,6-difluorobenzamide (30 mg, 0.08 mmol) was dissolved in 2 ml of dry THF, and the solution was cooled to 0° C. under nitrogen. This was followed by portion wise addition of NaH (10 mg, 0.24 mmol, 60% dispersion in mineral oil). The mixture was stirred at 0° C. for 10 minutes and at room temperature for 30 minutes. The mixture was cooled to 0° C., and a solution of benzoyl chloride (10 μl, 0.08 mmol) in 1 ml of THF was added dropwise. The resulting reaction mixture was stirred at 0° C. for 10 minutes and at room temperature overnight. After completion of the reaction, it was quenched by the addition of few drops of 1N HCl, and diluted with ethyl acetate. The organic phase was separated, washed successively with sat. NaHCO$_3$, brine and dried. The solvent was removed in vacuo, and the resulting residue was purified by ISCO using 20% EtOAc in hexane to yield pure product as yellow solid (15 mg, 38% yield). $^1$H NMR (300 MHz, CDCl$_3$) δ: 9.18 (s, 1H), 8.03 (s, 1H), 7.88 (m, 1H), 7.84 (d, J=9.0 Hz, 1H), 7.68-7.63 (m, 1H), 7.56-7.51 (m, 2H), 7.45-7.40 (m, 1H), 7.24-7.17 (m, 1H), 6.96-6.89 (m, 1H), 5.53 (s, 2H).

Example 10

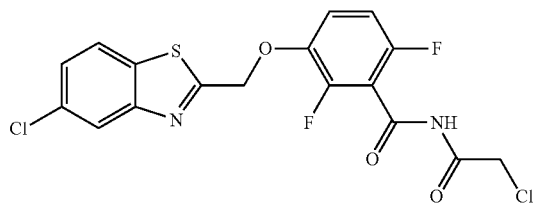 [SMILES: O=C(CCl)NC(=O)c1c(F)ccc(OCc2nc3cc(Cl)ccc3s2)c1F]

The mixture of 3-((5-chlorobenzo[d]thiazol-2-yl)methoxy)-2,6-difluorobenzamide (40 mg, 0.113 mmol) and chloroacetyl chloride (0.5 mL) is heated at 110° C. for 1 hour in a small reaction vial. The excess chloroacetyl chloride was removed under vacuum and the resulting residue was subjected to purification using ISCO to afford white solid (37 mg, 76% yield). $^1$H NMR (300 MHz, CDCl$_3$) δ: 8.81 (s, 1H), 8.04 (s, 1H), 7.86 (d, J=8.7 Hz, 1H), 7.43 (d, J=8.7 Hz, 1H), 7.27 (m, 1H), 6.95 (m, 1H), 5.55 (s, 2H), 4.60 (s, 2H).

Example 11

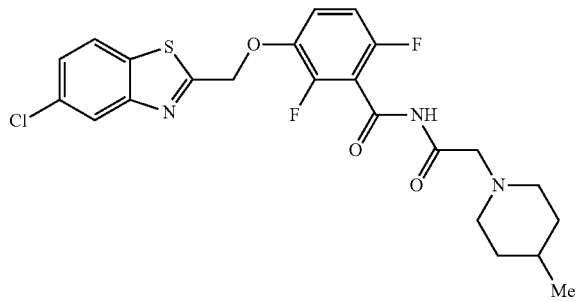 [SMILES: CC1CCN(CC(=O)NC(=O)c2c(F)ccc(OCc3nc4cc(Cl)ccc4s3)c2F)CC1]

To a mixture of 3-((5-chlorobenzo[d]thiazol-2-yl)methoxy)-2,6-difluorobenzoyl chloride (33 mg, 0.076 mmol), K$_2$CO$_3$ (13 mg, 0.09 mmol) in DMF (1.5 ml) was added 4-methylpiperidine (0.010 ml, 0.09 mmol) at room temperature. The reaction mixture was stirred at room temperature for 1 hour, after which it was diluted with ethyl acetate and washed with water once. Evaporation of the solvent followed by ISCO purification using 10% MeOH in CH$_2$Cl$_2$ afforded the pure product as colorless oil (12 mg, 33% yield). $^1$H NMR (300 MHz, CDCl$_3$) δ: 8.04 (s, 1H), 7.85 (d, J=8.7 Hz, 1H), 7.43 (d, J=8.4 Hz, 1H), 7.18 (m, 1H), 6.92 (m, 1H), 5.53 (s, 2H), 3.12 (s, 2H), 2.85 (m, 2H), 2.27 (m, 2H), 1.68 (m, 2H), 1.28 (m, 1H), 0.98 (d, J=6.0 Hz, 3H).

Example 12

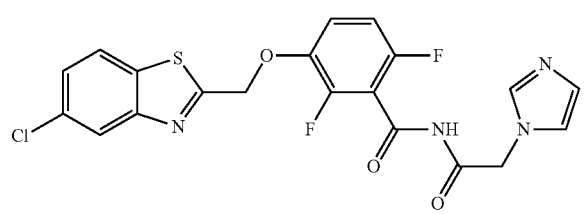 [SMILES: O=C(Cn1ccnc1)NC(=O)c1c(F)ccc(OCc2nc3cc(Cl)ccc3s2)c1F]

To the solution of 3-((5-chlorobenzo[d]thiazol-2-yl)methoxy)-2,6-difluorobenzoyl chloride (65 mg, 0.14 mmol) in DMF (1.5 ml) was added excess imidazole (48 mg, 0.70 mmol) and the mixture was stirred at room temperature overnight. The reaction mixture was poured into cold water and the solid thus formed was collected by filtration and was washed with ether to afford the desired compound as light yellow solid (58 mg, 90% yield). $^1$H NMR (DMSO-d6, 300 MHz) δ: 11.97 (s, 1H), 8.20 (d, J=8.7 Hz, 1H), 8.14 (s, 1H), 7.64 (s, 1H), 7.54 (m, 2H), 7.21 (m, 1H), 7.16 (s, 1H), 6.88 (s, 1H), 5.78 (s, 2H), 5.22 (s, 2H).

Example 13

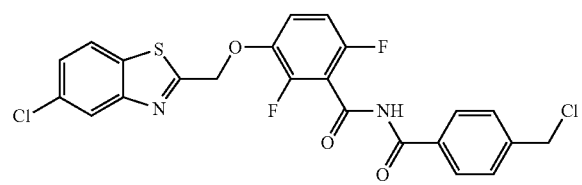 [SMILES: O=C(NC(=O)c1c(F)ccc(OCc2nc3cc(Cl)ccc3s2)c1F)c1ccc(CCl)cc1]

In a round bottom flask 3-((5-chlorobenzo[d]thiazol-2-yl)methoxy)-2,6-difluorobenzamide (55 mg, 0.155 mmol) was dissolved in 3 ml of dry THF, and the solution was cooled to 0° C. under nitrogen. This was followed by portion wise addition of NaH (13 mg, 0.310 mmol, 60% dispersion in mineral oil). The mixture was stirred at 0° C. for 10 minutes and at room temperature for 1 hour. The mixture was cooled to 0° C., and a solution of chlorobenzoyl chloride (0.1 ml) in 1 ml of THF was added dropwise. The resulting reaction mixture was stirred at 0° C. for 10 minutes and at room temperature for overnight. After completion of the reaction, it was quenched by the addition of few drops of 1N HCl, and diluted with ethyl acetate. The organic phase was separated, washed successively with sat. NaHCO$_3$, brine and dried. The solvent was removed in vacuo, and the resulting residue was purified by ISCO using 50% EtOAc in hexane to afford the desired product as white solid (52 mg, 66% yield). $^1$H NMR (300 MHz, CDCl$_3$) δ: 9.10 (s, 1H), 8.04 (s, 1H), 7.91-7.83 (m, 3H), 7.56 (d, J=9.0 Hz, 2H), 7.43 (d, J=6.0 Hz, 1H), 7.25-7.18 (m, 1H), 6.97-6.90 (m, 1H), 5.54 (s, 2H), 4.65 (s, 2H).

Example 14

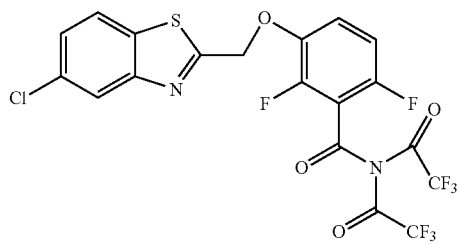 [SMILES: O=C(c1c(F)ccc(OCc2nc3cc(Cl)ccc3s2)c1F)N(C(=O)C(F)(F)F)C(=O)C(F)(F)F]

Trifluroacetic anhydride (0.05 ml, 0.339 mmol) is added to the solution of 3-((5-chlorobenzo[d]thiazol-2-yl)methoxy)-2,6-difluorobenzamide (100 mg, 0.282 mmol) in anhydrous THF (2 ml) and anhydrous pyridine (0.045 ml) at room temperature with stirring, followed by heating the mixture to 78° C. for 12 hours. The reaction mixture was cooled to room temperature, concentrated on a rotary evaporator and azeotroped with toluene once. The solid is re dissolved in $CH_2Cl_2$, washed with water, dried over $Na_2SO_4$ and concentrated to give crude product. Purification using 40% EtOAc in hexane afforded the desired product (10 mg) as white solid. $^1$H NMR (DMSO-d6, 300 MHz) δ: 8.21 (d, J=8.7 Hz, 1H), 8.14 (s, 1H), 7.84-7.79 (m, 1H), 7.54 (d, J=8.4 Hz, 1H), 7.47-7.40 (m, 1H), 5.76 (s, 2H).

Example 15

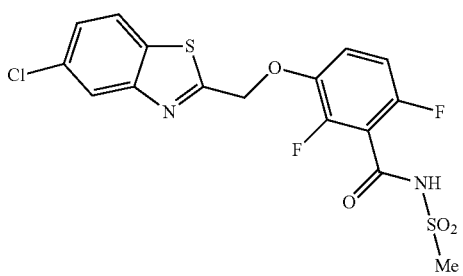 [SMILES: CS(=O)(=O)NC(=O)c1c(F)ccc(OCc2nc3cc(Cl)ccc3s2)c1F]

To a mixture of 3-((5-chlorobenzo[d]thiazol-2-yl)methoxy)-2,6-difluorobenzoyl chloride (97 mg, 0.26 mmol), methyl sulfonamide (26 mg, 0.26 mmol) in THF (1.5 mL) was added $Et_3N$ (0.1 ml, 0.66 mmol) followed by catalytic amount of DMAP. The mixture was heated in a sealed tube at 60° C. for 1.5 hours. The reaction mixture was cooled to room temperature, diluted with ethyl acetate, washed with 1N HCl and brine. The organic phase was dried over $Na_2SO_4$, concentrated and purified by ISCO using 50% EtOAc in hexane to afford the desired product as off white solid (68 mg, 61% yield). $^1$H NMR (300 MHz, $CDCl_3$) δ: 8.04 (s, 1H), 7.85 (d, 1H), 7.40 (d, 1H), 7.18 (m, 1H), 6.89 (m, 1H), 5.52 (s, 2H), 3.42 (s, 3H).

The requisite intermediates were prepared as follows.
a. Preparation of Compound

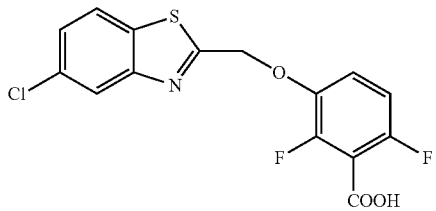 [SMILES: O=C(O)c1c(F)ccc(OCc2nc3cc(Cl)ccc3s2)c1F]

A suspension of 3-((5-chlorobenzo[d]thiazol-2-yl)methoxy)-2,6-difluorobenzamide (354 mg, 1.0 mmol) in 50% $H_2SO_4$ (6.0 ml) was heated at 120° C. for 3 hours. The reaction mixture was cooled down to room temperature, water was added and the resulting solid was filtered to afford a yellow solid as desired product (301 mg, 86% yield). $^1$H NMR (DMSO-d6, 300 MHz) δ: 8.20 (d, J=9.0 Hz, 1H), 8.13 (d, J=2.1 Hz, 1H), 7.56-7.47 (m, 2H), 7.21-7.15 (m, 1H), 5.73 (s, 2H).

b. Preparation of Compound

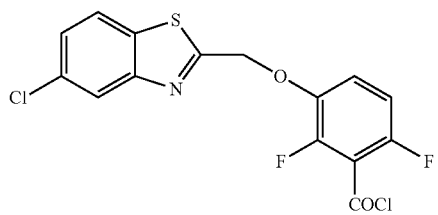 [SMILES: O=C(Cl)c1c(F)ccc(OCc2nc3cc(Cl)ccc3s2)c1F]

To a suspension of 3-((5-chlorobenzo[d]thiazol-2-yl)methoxy)-2,6-difluorobenzoic acid (200 mg) in $CH_2Cl_2$ (5.0 ml) was added catalytic amount of DMF followed by 1.5 equiv. oxalyl chloride. The reaction mixture was stirred at room temperature for 2 hours. The solvent was removed to afford crude acid chloride which was used for the next step without further purification.

Example 16

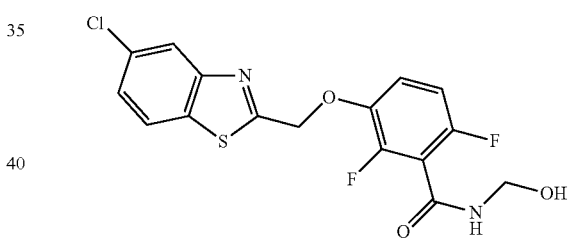

A mixture of 3-((5-chlorobenzo[d]thiazol-2-yl)methoxy)-2,6-difluorobenzamide (200 mg, 0.56 mmol), formaldehyde (1.5 ml), 5% $K_2CO_3$ (3.0 ml) in THF (1.5 ml) was heated to 65° C. overnight. After cooling to room temperature, water was added and the resulting solid was filtered and was washed with ether to give light yellow solid (190 mg, 88% yield). $^1$H NMR (DMSO-d6, 300 MHz) δ: 9.34 (bs, 1H), 8.20 (d, J=9.0 Hz, 1H), 8.14 (d, J=2.1 Hz, 1H), 7.54 (m, 1H), 7.45-7.38 (m, 1H), 7.17-7.10 (m, 1H), 5.72 (s, 2H), 4.66 (d, J=6.0 Hz, 2H).

Example 17

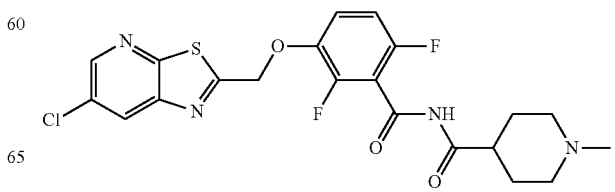

In a round bottom flask 3-((6-chlorothiazolo[5,4-b]pyridin-2-yl)methoxy)-2,6-difluorobenzamide (250 mg, 0.7 mmol) was dissolved in 4 ml of dry THF, and the solution was cooled to 0° C. under nitrogen. This was followed by portion wise addition of NaH (110 mg, 2.4 mmol, 60% dispersion in mineral oil). The mixture was stirred at 0° C. for 10 minutes and at room temperature for 30 minutes. The mixture was cooled to 0° C., and a solution of acyl chloride 8a (280 mg, 1.4 mmol) in 1 ml of THF was added dropwise. The resulting reaction mixture was stirred at 0° C. for 10 minutes and at room temperature overnight. After completion of the reaction, it was quenched by the addition of few drops of 1N NaOH, and diluted with ethyl acetate. The organic phase was separated, washed successively with sat. NaHCO$_3$, brine and dried. The solvent was removed in vacuo, and the resulting residue was purified by ISCO using 10% MeOH in CH$_2$Cl$_2$+1% NH$_4$OH to afford a light brown solid (50 mg, 15% yield). $^1$H NMR (300 MHz, CDCl$_3$) δ: 8.58 (s, 1H), 8.25 (s, 1H), 7.24 (m, 1H), 6.92 (m, 1H), 5.5 (s, 2H), 2.91 (m, 3H), 2.3 (s, 3H), 2.07-1.85 (m, 5H).

Example 18

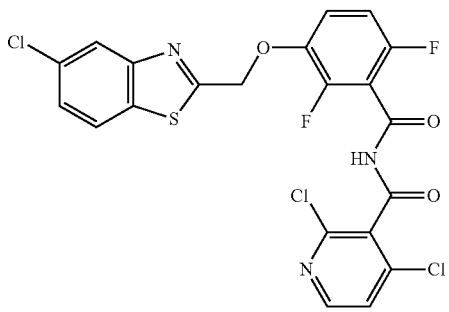 [SMILES: O=C(NC(=O)c1c(F)ccc(OCc2nc3cc(Cl)ccc3s2)c1F)c1c(Cl)ccnc1Cl]

3-((5-Chlorobenzo[d]thiazol-2-yl)methoxy)-2,6-difluorobenzamide (25.3 mg) and a stir bar were placed under vacuum in a 2-dram vial. The vial was then filled with N$_2$ (g). 3-((5-Chlorobenzo[d]thiazol-2-yl)methoxy)-2,6-difluorobenzamide was dissolved in anhydrous THF (3.5 mL) and the resulting solution was stirred under N$_2$(g) while at room temperature. 2,4-Dichloropyridine-3-carbonyl chloride (0.01 mL, 1.0 eq., Sigma-Aldrich Co.) was added dropwise via syringe, followed by addition of sodium hydride (60% in oil dispersion) (14.3 mg, 5.0 eq.). The reaction was heated at 50° C. for 1 hour 30 min. After cooling to room temperature, the reaction was concentrated to a solid and then dissolved in EtOAc/H$_2$O. After shaking, the aqueous phase was separated and then extracted with EtOAc. The combined EtOAc phases were dried over Na$_2$SO$_4$, filtered, and concentrated to a solid. Chromatography with solvent gradient 0>30% EtOAc/hexanes isolated the product as a solid (23 mg, 61% yield). $^1$H NMR (400 MHz) (CDCl$_3$) δ: 8.73 (br. s, 1H), 8.315 (d, J=5.4 Hz, 1H), 7.93 (d, J=2 Hz, 1H), 7.76 (d, J=8.6 Hz, 1H), 7.34 (dd, H=8.6 Hz, J=2 Hz, 2H), 7.30 (d, J=5.4 Hz, 1H), 7.18 (m, 1H), 6.88 (ddd, J=9 Hz, J=2 Hz, 1H), 5.45 (s, 2H). MS: m/e=528 (M+1).

Example 19

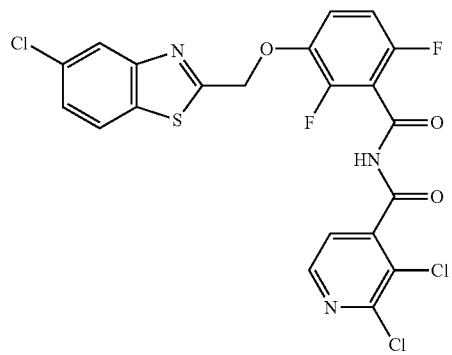 [SMILES: O=C(NC(=O)c1c(F)ccc(OCc2nc3cc(Cl)ccc3s2)c1F)c1ccnc(Cl)c1Cl]

3-((5-Chlorobenzo[d]thiazol-2-yl)methoxy)-2,6-difluorobenzamide (25.1 mg) and a stir bar were placed under vacuum in a 2-dram vial. The vial was then filled with N$_2$ (g). 3-((5-Chlorobenzo[d]thiazol-2-yl)methoxy)-2,6-difluorobenzamide was dissolved in anhydrous THF (3.5 mL) and the resulting solution was stirred under N$_2$ (g) while at room temperature. 2,3-Dichloropyridine-4-carbonyl chloride (0.0095 mL, 1.0 eq., Sigma-Aldrich Co.) was added dropwise via syringe, followed by addition of sodium hydride (60% in oil dispersion) (14.2 mg, 5.0 eq.) The reaction was heated at 50° C. for 2 hours. After cooling to room temperature, the reaction was concentrated to a residue and then dissolved in EtOAc/H$_2$O. After shaking, the aqueous phase was separated and extracted with EtOAc. The combined EtOAc phases were dried over Na$_2$SO$_4$, filtered, and concentrated to a solid. Chromatography with solvent gradient 0>30% EtOAc/hexanes isolated the product as a solid (15 mg, 39% yield). $^1$H NMR (400 MHz) (CDCl$_3$) δ: 8.60 (br. s, 1H), 8.37 (d, J=4.84 Hz, 1H), 7.95 (d, J=2 Hz, 1H), 7.76 (d, J=8.6 Hz, 1H), 7.33 (dd, J=8.6 Hz, J=2 Hz, 1H), 7.27 (d, J=4.84 Hz, 1H), 7.20 (m, 1H), 6.88 (ddd, J=9 Hz, J=9 Hz, J=2 Hz, 1H), 5.46 (s, 2H). MS: m/e=528 (M+1).

Example 20

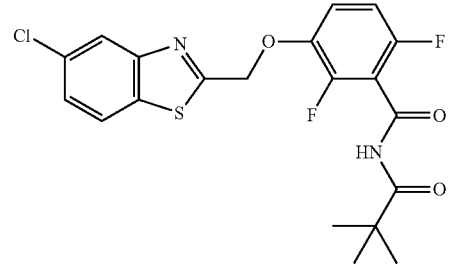

3-((5-Chlorobenzo[d]thiazol-2-yl)methoxy)-2,6-difluorobenzamide (25.8 mg) and a stir bar were placed under vacuum in a 2-dram vial. The vial was then filled with N$_2$ (g). 3-((5-chlorobenzo[d]thiazol-2-yl)methoxy)-2,6-difluorobenzamide was dissolved in anhydrous THF (3.5 mL) and the resulting solution was stirred under N$_2$ (g) while at room temperature. Trimethylacetyl chloride (0.009 mL, 1.0 eq., Sigma-Aldrich Co.) was added dropwise via syringe, followed by addition of sodium hydride (60% in oil dispersion) (13.4 mg, 4.6 eq.). The reaction was heated at 50° C. for 2 hours. After cooling to room temperature, the reaction was concentrated to a residue and then dissolved in EtOAc/H$_2$O.

After shaking, the aqueous phase was separated and then extracted with EtOAc. The combined EtOAc phases were dried over Na$_2$SO$_4$, filtered, and concentrated to a solid. Chromatography with solvent gradient 0>30% EtOAc/hexanes isolated the product as a solid (15.6 mg, 49% yield). $^1$H NMR (400 MHz) (CD$_3$OD) δ: 7.92 (d, J=8.6 Hz, 1H), 7.91 (d, J=2 Hz, 1H), 7.38 (dd, J=8.6 Hz, J=2 Hz, 1H), 7.27 (ddd, J=9 Hz, J=9 Hz, J=5.1 Hz, 1H), 6.89 (ddd, J=9 Hz, J=9 Hz, J=2 Hz, 1H), 5.50 (s, 2H), 1.14 (s, 9H). MS: m/e=439 (M+1).

Example 21

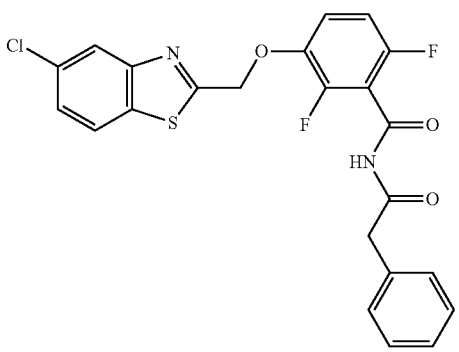

3-((5-Chlorobenzo[d]thiazol-2-yl)methoxy)-2,6-difluorobenzamide (25.3 mg) and a stir bar were placed under vacuum in a 2-dram vial. The vial was then filled with N$_2$ (g). 3-((5-Chlorobenzo[d]thiazol-2-yl)methoxy)-2,6-difluorobenzamide was dissolved in anhydrous THF (3.5 mL) and the resulting solution was stirred under N$_2$ (g) while at room temperature. Phenylacetyl chloride (9.4 μL, 1.0 eq., Sigma-Aldrich Co.) was added dropwise via syringe, followed by addition of sodium hydride (60% in oil dispersion) (14.3 mg, 5.0 eq.). The reaction was heated at 50° C. for 2 hours. After cooling to room temperature, the reaction was concentrated to a residue and then dissolved in EtOAc/H$_2$O. After shaking, the aqueous phase was separated and then extracted with EtOAc. The combined EtOAc phases were dried over Na$_2$SO$_4$, filtered, and concentrated to a solid. Chromatography with solvent gradient 0>30% EtOAc/hexanes isolated the product as a solid (7.6 mg, 22% yield). $^1$H NMR (400 MHz) (CDCl$_3$) δ: 8.15 (br. s, 1H), 7.95 (d, J=2 Hz, 1H), 7.76 (d, J=8.54 Hz, 1H), 7.34 (dd, J=8.54 Hz, J=2 Hz, 1H), 7.31-7.22 (m, 5H), 7.11 (ddd, J=9 Hz, J=9 Hz, J=5.1 Hz, 1H), 6.82 (ddd, J=9 Hz, J=9 Hz, J=2 Hz, 1H), 5.45 (s, 2H), 4.0 (s, 2H). MS: m/e=473 (M+1).

Example 22

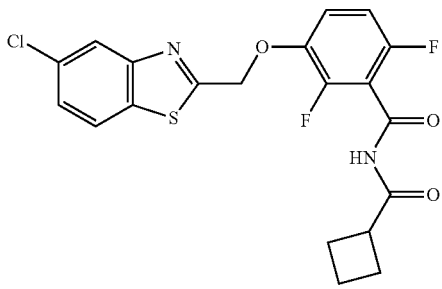 [SMILES: O=C(NC(=O)C1CCC1)c1c(F)ccc(OCc2nc3cc(Cl)ccc3s2)c1F]

3-((5-Chlorobenzo[d]thiazol-2-yl)methoxy)-2,6-difluorobenzamide (25.1 mg) and a stir bar were placed under vacuum in a 2-dram vial. The vial was then filled with N$_2$ (g). 3-((5-chlorobenzo[d]thiazol-2-yl)methoxy)-2,6-difluorobenzamide was dissolved in anhydrous THF (4.0 mL) and the resulting solution was stirred under N$_2$ (g) while at room temperature. Cyclobutanecarbonyl chloride (8.1 μL, 1.0 eq., Sigma-Aldrich Co.) was added dropwise via syringe, followed by addition of sodium hydride (60% in oil dispersion) (14.3 mg, 5.0 eq.). The reaction was heated at 50° C. for 2 hours. After cooling to room temperature, the reaction was concentrated to a residue and then dissolved in EtOAc/H$_2$O. After shaking, the aqueous phase was separated and then extracted with EtOAc. The combined EtOAc phases were dried over Na$_2$SO$_4$, filtered, and concentrated to a solid. Chromatography with solvent gradient 0>30% EtOAc/hexanes isolated the product as a solid (22.9 mg, 74% yield). $^1$H NMR (400 MHz) (CD$_3$OD) δ: (d, J=8.5 Hz, 1H), 7.906 (d, J=2.1 Hz, 1H), 7.37 (dd, J=8.5 Hz, J=2.1 Hz, 1H), 7.28 (ddd, J=9.2 Hz, J=9.2 Hz, J=5.1 Hz, 1H), 6.91 (ddd, J=9.2 Hz, J=9.2 Hz, J=2 Hz, 1H), 5.50 (s, 2H), 3.38 (m, 1H), 2.18 (m, 4H), 1.92 (m, 1H), 1.79 (m, 1H). MS: m/e=437 (M+1).

Example 23

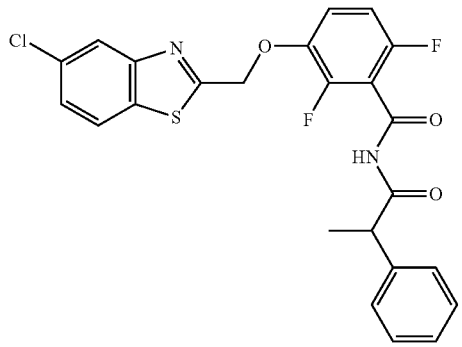 [SMILES: CC(C(=O)NC(=O)c1c(F)ccc(OCc2nc3cc(Cl)ccc3s2)c1F)c1ccccc1]

3-((5-Chlorobenzo[d]thiazol-2-yl)methoxy)-2,6-difluorobenzamide (25.6 mg) and a stir bar were placed under vacuum in a 2-dram vial. The vial was then filled with N$_2$ (g). 3-((5-Chlorobenzo[d]thiazol-2-yl)methoxy)-2,6-difluorobenzamide was dissolved in anhydrous THF (4.0 mL) and the resulting solution was stirred under N$_2$ (g) while at room temperature. 2-Phenylpropionyl chloride (12.3 mg, 1.0 eq., Sigma-Aldrich Co.) was added dropwise via syringe, followed by addition of sodium hydride (60% in oil dispersion) (8.7 mg, 3.0 eq.). The reaction was heated at 50° C. for 30 min. After cooling to room temperature, the reaction was concentrated to a residue and then dissolved in EtOAc/H$_2$O. After shaking, the aqueous phase was separated and then extracted with EtOAc. The combined EtOAc phases were dried over Na$_2$SO$_4$, filtered, and concentrated to a solid. Chromatography with solvent gradient 0>20% EtOAc/hexanes isolated the product as a solid (17.9 mg, 51% yield). $^1$H NMR (400 MHz) (CDCl$_3$) δ: (br. s, 1H), 8.04 (d, J=2 Hz, 1H), 7.85 (d, J=8.56 Hz, 1H), 7.45-7.29 (m, 6H), 7.18 (ddd, J=9.1 Hz, J=9.1 Hz, J=5 Hz, 1H), 6.88 (ddd, J=9.1 Hz, J=9.1 Hz, J=2 Hz, 1H), 5.51 (s, 2H), 4.09 (q, J=7.1 Hz, 1H), 1.54 (d, J=7.1 Hz, 3H). MS: m/e=487 (M+1).

Example 24

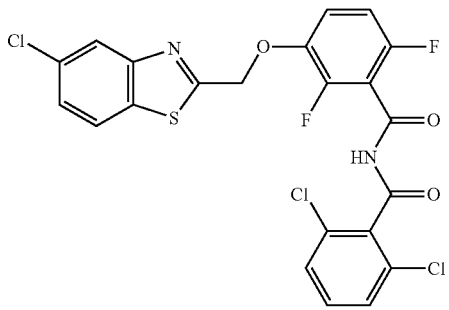 [SMILES: O=C(NC(=O)c1c(F)ccc(OCc2nc3cc(Cl)ccc3s2)c1F)c1c(Cl)cccc1Cl]

3-((5-Chlorobenzo[d]thiazol-2-yl)methoxy)-2,6-difluorobenzamide (25.2 mg) and a stir bar were placed under vacuum in a 2-dram vial. The vial was then filled with N₂ (g). 3-((5-chlorobenzo[d]thiazol-2-yl)methoxy)-2,6-difluorobenzamide was dissolved in anhydrous THF (4.0 mL) and the resulting solution was stirred under N₂ (g) while at room temperature. 2,6-Dichlorobenzoyl chloride (10 µL, 1.0 eq., Sigma-Aldrich Co.) was added dropwise via syringe, followed by addition of sodium hydride (60% in oil dispersion) (8.5 mg, 3.0 eq.). The reaction was heated at 50° C. for 30 min. After cooling to room temperature, the reaction was concentrated to an oil which was then dissolved in EtOAc/H₂O. After shaking, the aqueous phase was separated and extracted with EtOAc. The combined EtOAc phases were dried over Na₂SO₄, filtered, and concentrated to provide an oil. Chromatography with solvent gradient 0>20% EtOAc/hexanes isolated the product as a solid (15.4 mg, 39% yield). ¹H NMR (400 MHz) (CDCl₃) δ: 8.50 (br. s, 1H), 7.94 (d, J=2 Hz, 1H), 7.76 (d, J=8.6 Hz, 1H), 7.33 (dd, J=8.6 Hz, J=2 Hz, 1H), 7.32-7.13 (m, 4H), 6.86 (ddd, J=9.12 Hz, J=9.12 Hz, J=2 Hz, 1H), 5.45 (s, 2H). MS: m/e=527 (M+1).

Example 25

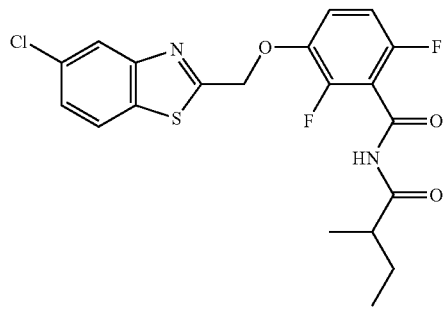 [SMILES: CCC(C)C(=O)NC(=O)c1c(F)ccc(OCc2nc3cc(Cl)ccc3s2)c1F]

3-((5-Chlorobenzo[d]thiazol-2-yl)methoxy)-2,6-difluorobenzamide (26.6 mg) and a stir bar were placed under vacuum in a 2-dram vial. The vial was then filled with N₂ (g). 3-((5-Chlorobenzo[d]thiazol-2-yl)methoxy)-2,6-difluorobenzamide was dissolved in anhydrous THF (4.0 mL) and the resulting solution was stirred under N₂ (g) while at room temperature. 2-Methylbutyryl chloride (9.3 µL, 1.0 eq., Sigma-Aldrich Co.) was added dropwise via syringe, followed by addition of sodium hydride (60% in oil dispersion) (9.0 mg, 3.0 eq.). The reaction continued to stir under N₂ (g) while at room temperature for 30 min. The reaction was concentrated to a residue which was then dissolved in EtOAc/H₂O. After shaking, the aqueous phase was separated and extracted with EtOAc. The combined EtOAc phases were dried over Na₂SO₄, filtered, and concentrated to a solid. Chromatography with solvent gradient 10>30% EtOAc/hexanes isolated the product as a solid (15.5 mg, 47% yield). ¹H NMR (400 MHz) (CDCl₃) δ: 8.21 (br. s, 1H), 8.04 (d, J=2 Hz, 1H), 7.85 (d, J=8.55 Hz, 1H), 7.43 (dd, J=8.55 Hz, J=2 Hz, 1H), 7.20 (ddd, J=9 Hz, J=9 Hz, J=5.1 Hz, 1H), 6.91 (ddd, J=9 Hz, J=9 Hz, J=2 Hz, 1H), 5.05 (s, 2H), 1.81 (m, J=7 Hz, 1H), 1.54 (d, J=7 Hz, 2H), 1.25 (d, J=7 Hz, 3H), 1.00 (t, J=7 Hz, 3H). MS: m/e=439 (M+1).

Example 26

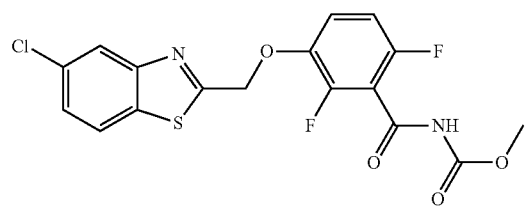 [SMILES: COC(=O)NC(=O)c1c(F)ccc(OCc2nc3cc(Cl)ccc3s2)c1F]

3-((5-Chlorobenzo[d]thiazol-2-yl)methoxy)-2,6-difluorobenzamide (25.4 mg) and a stir bar were placed under vacuum in a 2-dram vial. The vial was then filled with N₂ (g). 3-((5-Chlorobenzo[d]thiazol-2-yl)methoxy)-2,6-difluorobenzamide was dissolved in THF (3.5 mL) and the resulting solution was stirred under N₂ (g) while at room temperature. Methyl chloroformate (5.5 µL, 1.0 eq., Acros Organics) was added dropwise via syringe, followed by addition of sodium hydride (60% in oil dispersion) (14.3 mg, 5.0 eq.). The reaction was heated to 50° C. with gradual warming to 70° C. over a two hour period. After cooling to room temperature, and the reaction was concentrated to a solid and dissolved in EtOAc/H₂O. After shaking, the aqueous phase was separated and extracted with EtOAc. The combined EtOAc phases were dried over Na₂SO₄, filtered, and concentrated to a solid. Chromatography with solvent gradient 10>30% EtOAc/hexanes isolated the product as a solid (12.1 mg, 41% yield). ¹H NMR (400 MHz) (CD₃OD) δ: 7.92 (d, J=8.6 Hz, 1H), 7.91 (d, J=2 Hz, 1H), 7.37 (dd, J=8.6 Hz, J=2 Hz, 1H), 7.29 (ddd, J=9 Hz, J=9 Hz, J=5.1 H_Z, 1H), 6.91 (ddd, J=9 Hz, J=9 Hz, J=2 Hz, 1H), 5.50 (s, 2H), 3.66 (s, 3H). MS: m/e=413 (M+1).

Example 27

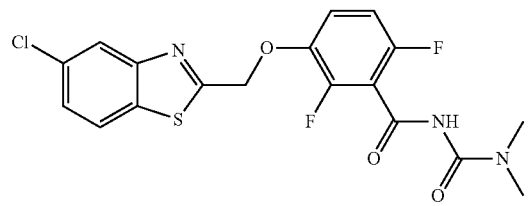

3-((5-Chlorobenzo[d]thiazol-2-yl)methoxy)-2,6-difluorobenzamide (26.4 mg) and a stir bar were placed under vacuum in a 2-dram vial. The vial was then filled with N₂ (g). 3-((5-chlorobenzo[d]thiazol-2-yl)methoxy)-2,6-difluorobenzamide was dissolved in THF (3.5 mL) and the resulting solution was stirred under N₂ (g) while at room temperature. Dimethylcarbamoyl chloride (6.8 µL, 1.0 eq., TCI America, Inc.) was added dropwise via syringe, followed by addition of sodium hydride (60% in oil dispersion) (14.9 mg, 5.0 eq.). The reaction was stirred at 65° C. while under N₂ (g) for 2 hours. After cooling to room temperature, the reaction was concentrated to a solid and dissolved in EtOAc/H₂O. After shaking, the aqueous phase was separated and extracted with EtOAc. The combined EtOAc phases were dried over Na₂SO₄, filtered, and concentrated to a solid. Chromatography with solvent gradient 45>50% EtOAc/hexanes isolated the product as a solid (14.0 mg, 44% yield). ¹H NMR (400 MHz) (CD₃OD) δ: 7.91 (d, J=8.6 Hz, 1H), 7.90 (d, J=2 Hz, 1H), 7.37 (dd, J=8.6 Hz, J=2 Hz, 1H), 7.265 (ddd, J=9 Hz, J=9 Hz, J=5.1, 1H), 6.895 (ddd, J=9 Hz, J=9 Hz, J=2 Hz, 1H), 5.49 (s, 2H), 2.92 (br. s, 6H). MS: m/e=426 (M+1).

Example 28

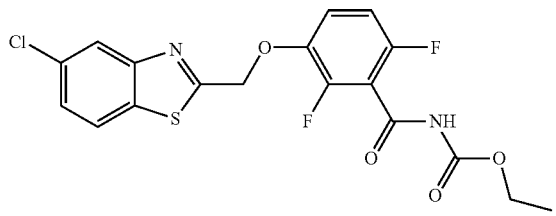 [SMILES: CCOC(=O)NC(=O)c1c(F)ccc(OCc2nc3cc(Cl)ccc3s2)c1F]

3-((5-Chlorobenzo[d]thiazol-2-yl)methoxy)-2,6-difluorobenzamide (26.9 mg) and a stir bar were placed under vacuum in a 2-dram vial. The vial was then filled with N₂ (g). 3-((5-Chlorobenzo[d]thiazol-2-yl)methoxy)-2,6-difluorobenzamide was dissolved in THF (3.5 mL) and the resulting solution was stirred under N₂ (g) while at room temperature. Ethyl chloroformate (7.25 µL, 1.0 eq., Sigma-Aldrich Co.) was added dropwise via syringe, followed by addition of sodium hydride (60% in oil dispersion) (15.2 mg, 5.0 eq.). The reaction was heated to 75° C. for 2 hours while under N₂ (g). After cooling to room temperature, and the reaction was concentrated to a solid and dissolved in EtOAc/H₂O. After shaking, the aqueous phase was separated and extracted with EtOAc. The combined EtOAc phases were dried over Na₂SO₄, filtered, and concentrated to a solid. Chromatography with solvent gradient 10>30% EtOAc/hexanes isolated the product as a solid (17.9 mg, 55% yield). ¹H NMR (400 MHz) (CD₃OD) δ: 7.91 (d, J=8.6 Hz, 1H), 7.91 (d, J=2 Hz, 1H), 7.37 (dd, J=8.6 Hz, J=2 Hz, 1H) 7.28 (ddd, J=9 Hz, J=9 Hz, J=5.1 Hz, 1H), 6.90 (ddd, J=9 Hz, J=9 Hz, J=2 Hz, 1H), 5.50 (s, 2H), 4.10 (q, J=7.12 Hz, 2H), 1.15 (t, J=7.12 Hz, 3H).

Example 29

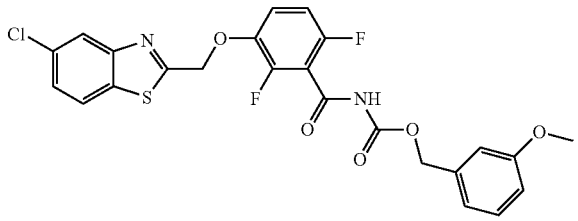 [SMILES: COc1cccc(COC(=O)NC(=O)c2c(F)ccc(OCc3nc4cc(Cl)ccc4s3)c2F)c1]

3-((5-Chlorobenzo[d]thiazol-2-yl)methoxy)-2,6-difluorobenzamide (26.0 mg) and a stir bar were placed under vacuum in a 2-dram vial. The vial was then filled with N₂ (g). 3-((5-Chlorobenzo[d]thiazol-2-yl)methoxy)-2,6-difluorobenzamide was dissolved in THF (3.5 mL) and the resulting solution was stirred under N₂ (g) while at room temperature. 3-Methoxyphenylacetyl chloride (11.4 µL, 1.0 eq., Sigma-Aldrich Co.) was added dropwise via syringe, followed by addition of sodium hydride (60% in oil dispersion) (14.7 mg, 5.0 eq.). The reaction was heated to 50° C. for 1 hour and 75° C. for 30 min. After cooling to room temperature, the reaction was concentrated to a solid and dissolved in EtOAc/H₂O. After shaking, the aqueous phase was separated and extracted with EtOAc. The combined EtOAc phases were dried over Na₂SO₄, filtered, and concentrated to a solid. Chromatography with solvent gradient 10>30% EtOAc/hexanes isolated the product as a solid (3.2 mg, 8.4% yield). ¹H NMR (400 MHz) (CD₃OD) δ: 7.91 (m, 2H), 7.37 (dd, J=8.68 Hz, J=1.92 Hz, 1H), 7.28 (ddd, J=9 Hz, J=9 Hz, J=5 Hz, 1H), 7.13 (m, 1H), 6.90 (ddd, J=9 Hz, J=9 Hz, J=2 Hz, 1H), 6.78-6.71 (m, 3H), 5.5 (s, 2H).

Example 30

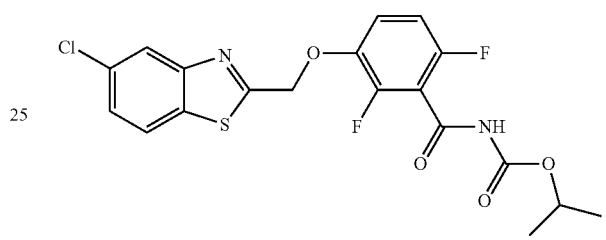

3-((5-Chlorobenzo[d]thiazol-2-yl)methoxy)-2,6-difluorobenzamide (26.8 mg) and a stir bar were placed under vacuum in a 2-dram vial. The vial was then filled with N₂ (g). 3-((5-chlorobenzo[d]thiazol-2-yl)methoxy)-2,6-difluorobenzamide was dissolved in THF (3.5 mL) and the resulting solution was stirred under N₂ (g) while at room temperature. Isopropyl chloroformate (1M in toluene) (75.5 µl, 1.0 eq., Sigma-Aldrich Co.) was added dropwise via syringe, followed by addition of sodium hydride (60% in oil dispersion) (15.1 mg, 5.0 eq.). The reaction was heated to 50° C., then gradually warmed to 75° C. over 3 hours 45 min. After cooling to room temperature, and the reaction was concentrated to a solid and dissolved in EtOAc/H₂O. After shaking, the aqueous phase was separated and then extracted with EtOAc. The combined EtOAc phases were dried over Na₂SO₄, filtered, and concentrated to a solid. Chromatography with solvent gradient 10>30% EtOAc/hexanes isolated a solid (8.5 g, 25% yield). ¹H NMR (400 MHz) (CDCl₃) δ: 7.945 (d, J=2 Hz, 1H), 7.76 (d, J=8.6 Hz, 1H), 7.655 (br. s, 1H), 7.34 (dd, J=8.6 Hz, J=2 Hz, 1H), 7.09 (ddd, J=9 Hz, J=9 Hz, J=5.1 Hz, 1H), 6.81 (ddd, J=9 Hz, J=9 Hz, J=2 Hz, 1H), 5.44 (s, 2H), 4.89 (m, J=6.28 Hz, 1H), 1.19 (d, J=6.28 Hz, 6H). MS: m/e=441 (M+1).

Example 31

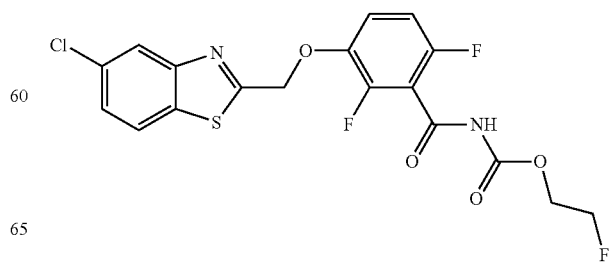

3-((5-Chlorobenzo[d]thiazol-2-yl)methoxy)-2,6-difluorobenzamide (25.7 mg) and a stir bar were placed under vacuum in a 2-dram vial. The vial was then filled with $N_2$ (g). 3-((5-Chlorobenzo[d]thiazol-2-yl)methoxy)-2,6-difluorobenzamide was dissolved in THF (3.5 mL) and the resulting solution was stirred under $N_2$ (g) while at room temperature. 2-Fluoroethylformate (7.0 μL, 1.0 eq., Sigma-Aldrich Co.) was added dropwise, followed by addition of sodium hydride (60% in oil dispersion) (14.5 mg, 5.0 eq.). The reaction was heated at 50° C. for 1 hour and then at 75° C. for 2 hours. After cooling to room temperature, and the reaction was concentrated to a solid and dissolved in EtOAc/$H_2O$. After shaking, the aqueous phase was separated and then extracted with EtOAc. The combined EtOAc phases were dried over $Na_2SO_4$, filtered, and concentrated to a solid. Chromatography with solvent gradient 0>45% EtOAc/hexanes isolated a solid (15.7 mg, 49% yield). $^1H$ NMR (400 MHz) (CDCl$_3$) δ: 7.95 (d, J=2 Hz, 1H), 7.84 (br. s, 1H), 7.76 (d, J=8.6 Hz, 1H), 7.34 (dd, J=8.6 Hz, J=2 Hz, 1H), 7.11 (ddd, J=9 Hz, J=9 Hz, J=5.1 Hz, 1H), 6.82 (ddd, J=9 Hz, J=9 Hz, J=2 Hz, 1H), 4.54 (dt, J=47.28 Hz, J=4.1 Hz, 2H), 4.34 (dt, J=28.2 Hz, J=4.1 Hz, 2H). MS: m/e=445 (M+1).

Example 32

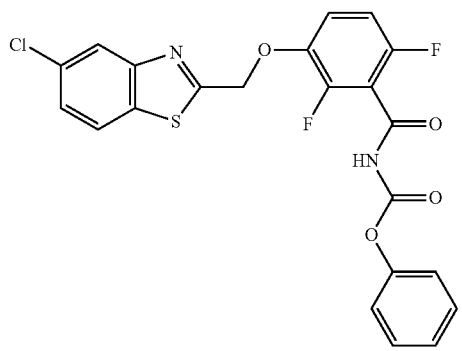 [SMILES: O=C(NC(=O)c1c(F)ccc(OCc2nc3cc(Cl)ccc3s2)c1F)Oc1ccccc1]

3-((5-Chlorobenzo[d]thiazol-2-yl)methoxy)-2,6-difluorobenzamide (26.5 mg) and a stir bar were placed under vacuum in a 2-dram vial. The vial was then filled with $N_2$ (g). 3-((5-Chlorobenzo[d]thiazol-2-yl)methoxy)-2,6-difluorobenzamide was dissolved in anhydrous THF (3.5 mL) and the resulting solution was stirred under $N_2$ (g) while at room temperature. Phenylchloroformate (9.4 μL, 1.0 eq., Sigma-Aldrich Co.) was added dropwise via syringe, followed by addition of sodium hydride (60% in oil dispersion) (15 mg, 5.0 eq.). The reaction was heated at 75° C. for 2 hours. After cooling to room temperature, the reaction was concentrated to a residue and then dissolved in EtOAc/$H_2O$. After shaking, the aqueous phase was separated and then extracted with EtOAc. The combined EtOAc phases were dried over $Na_2SO_4$, filtered, and concentrated to a solid. Chromatography with solvent gradient 10>45% EtOAc/hexanes isolated the product as a solid (12.8 mg, 36% yield). $^1H$ NMR (300 MHz) (CD$_3$OD) δ: 8.03 (d, J=8.6 Hz, 1H), 8.02 (d, J=2 Hz, 1H), 7.49 (dd, J=8.6 Hz, J=2 Hz, 1H), 7.43 (m, 3H), 7.29 (ddd, J=9 Hz, J=9 Hz, J=5.1 Hz, 1H), 7.20 (m, 2H), 7.05 (ddd, J=9 Hz, J=9 Hz, J=2 Hz, 1H), 5.65 (s, 2H).

Example 33

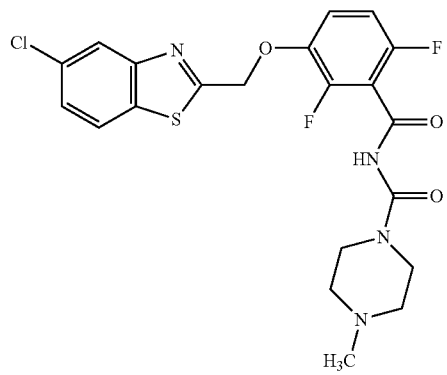 [SMILES: CN1CCN(C(=O)NC(=O)c2c(F)ccc(OCc3nc4cc(Cl)ccc4s3)c2F)CC1]

Phenyl(3-((5-chlorobenzo[d]thiazol-2-yl)methoxy)-2,6-difluorobenzoyl)carbamate (6.5 mg, 1.0 eq.) and 1-methylpiperazine (2.0 μL, 1.0 eq.) were placed in toluene (0.2 mL) and stirred at 100° C. for 1 hour. After cooling to room temperature, the reaction was concentrated to a solid. Chromatography with $CH_2Cl_2$, (90 $CH_2Cl_2$: 10 MeOH: 1 NH$_4$OH) isolated the product as a solid (4.9 mg, 74%). $^1H$ NMR (300 MHz) (CDCl$_3$) δ: 8.05 (d, J=2 Hz, 1H), 7.85 (d, J=8.7 Hz, 1H), 7.67 (br. s, 1H), 7.43 (dd, J=8.7 Hz, J=2 Hz, 1H), 7.16 (ddd, J=9 Hz, J=9 Hz, J=5.1 Hz, 1H), 6.91 (ddd, J=9 Hz, J=9 Hz, J=2 Hz, 1H), 5.5 (s, 2H), 3.56 (m, 4H), 2.5 (m, 4H), 2.35 (s, 3H). MS: m/e=481 (M+1).

Example 34

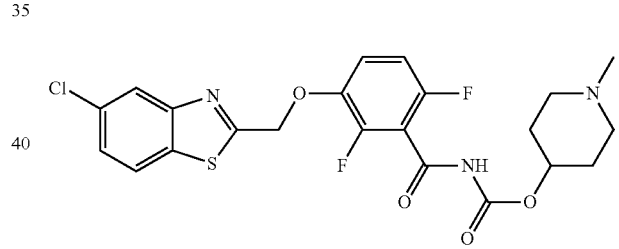

3-((5-Chlorobenzo[d]thiazol-2-yl)methoxy)-2,6-difluorobenzamide (26.3 mg, 0.074 mmol, 1.0 eq.) and a stir bar were placed under vacuum in a 2-dram vial. The vial was then filled with $N_2$ (g). 3-((5-Chlorobenzo[d]thiazol-2-yl)methoxy)-2,6-difluorobenzamide was dissolved in anhydrous THF (3.5 mL) and stirred at room temperature. 1-Methylpiperidin-4-yl carbonochloridate HCl salt (19 mg, 0.09 mmol, 1.2 eq.) was added, followed by addition of sodium hydride (60% in oil dispersion) (14.8 mg, 0.37 mmol, 5.0 eq.). Stirring continued at room temperature for 1 hour and at 50° C. for 10 minutes. The reaction suspension concentrated to a solid and dissolved in EtOAc/$H_2O$. After stirring, the aqueous phase was separated and extracted with EtOAc. The combined EtOAc layers were dried over $Na_2SO_4$, filtered, and concentrated to a solid. Chromatography with (95 $CH_2Cl_2$: 5 MeOH: 1 NH$_4$OH) and (90 $CH_2Cl_2$: 10 MeOH: 1 NH$_4$OH) isolated 1-methylpiperidin-4-yl (3-((5-chlorobenzo[d]thiazol-2-yl)methoxy)-2,6-difluorobenzoyl)carbamate as a solid (10 mg, 27%). $^1H$ NMR (300 MHz) (DMSO) δ: 11.55 (br, s, 1H), 8.2 (d, J=8.5 Hz, 1H), 8.13 (d, J=2 Hz, 1H), 7.55 (dd, J=8.5 Hz, J=2 Hz, 1H), 7.47 (ddd, J=9 Hz, J=9 Hz, J=5.1 Hz, 1H), 7.16 (ddd, J=9

Hz, J=9 Hz, J=2 Hz, 1H), 5.72 (s, 2H), 4.62 (m, 1H), 2.13 (s, 3H), 2.09 (m, 2H), 1.81 (m, 3H), 1.55 (m, 3H). MS: m/e=496 (M+1).

a. Preparation of Compound

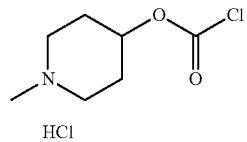

HCl

4-Hydroxy-1-methyl piperidine (0.51 mL, 4.34 mmol, 1.0 eq.) was placed under $N_2$ (g) and dissolved in 10 mL of anhydrous acetonitrile. The resulting solution was cooled to 0° C. in an ice/water bath. Trichloromethylchloroformate (0.68 mL, 5.64 mmol, 1.3 eq.) was added dropwise, and a suspension formed. After stirring for 30 min at 0° C., the reaction was warmed to room temperature and stirred overnight under $N_2$ (g). The reaction suspension was filtered, and the collected solid was washed with acetonitrile. After further drying under vacuum, the solid was triturated with diethyl ether and collected by filtration to yield 1-methyl-piperidin-4-yl carbonochloridate, HCl salt (0.52 g, 55%). $^1$H NMR (300 MHz) (CD$_3$OD) δ: 4.95 (m, 1H), 3.6 (m, 1H), 3.4 (m, 1H), 3.2 (m, 2H), 2.85 (s, 3H), 2.5 (m, 1H), 2.2 (m, 2H), 1.9 (m, 1H), MS: m/e=178 (M+1).

Example 35

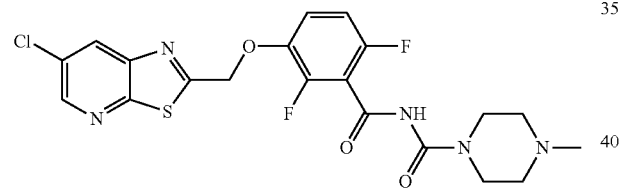

3-((6-Chlorothiazolo[5,4-b]pyridin-2-yl)methoxy)-2,6-difluorobenzamide (0.1 g, 0.281 mmol, 1.0 eq.) was suspended in 3 mL CH$_2$Cl$_2$ while stirring at room temperature. Oxalyl chloride (0.1 mL, 1.2 mmol, 4.2 eq.) was added dropwise, and stirring continued in a sealed flask at 45° C. for 20 hours. The reaction was cooled to room temperature and then concentrated to a residue. The residue was partially dissolved in 5 mL CH$_2$Cl$_2$. The suspension was cooled to −78° C. in a dry ice/acetone bath. Triethylamine (0.2 mL, 1.44 mmol, 5.1 eq.) was added dropwise and stirring continued for approximately 5 min. 1-Methylpiperazine (32 μL, 0.30 mmol, 1.1 eq.) was added dropwise and the reaction was warmed to room temperature. After stirring for 30 min, the reaction was concentrated to a brown oil, which was then dissolved in EtOAc/H$_2$O. The EtOAc phase was washed with brine, dried over Na$_2$SO$_4$, filtered, and concentrated to a residue. Chromatography with 0>10% MeOH/CH$_2$Cl$_2$ isolated the product as a solid (27.0 mg, 20%). $^1$H NMR (300 MHz) (CDCl$_3$) δ: 8.61 (d, J=2.2 Hz, 1H), 8.267 (d, 2.2 Hz, 1H), 8.199 (br. s, 1H), 7.18 (ddd, J=9.0 Hz, J=5.0 Hz, 1H), 6.915 (ddd, J=9.0 Hz, J=9.0 Hz, J=2.1 Hz, 1H), 5.505 (s, 2H), 3.59 (m, 4H), 2.51 (m, 4H), 2.36 (s, 3H). MS: m/e=482 (M+1).

Example 36

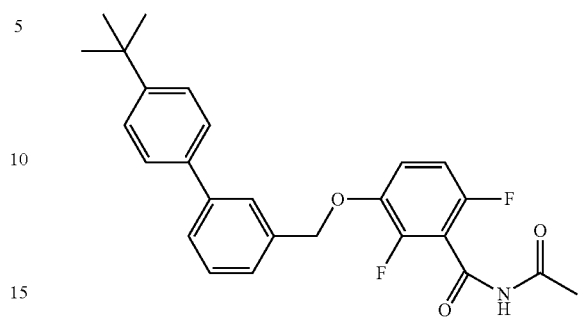

In a 2-dram vial, a suspension of 3-((4'-(tert-butyl)-[1,1'-biphenyl]-3-yl)methoxy)-2,6-difluorobenzamide (20 mg, 0.05 mmol) in 1 ml of N,N-dimethylacetamide dimethyl acetal was capped and stirred at 90° C. for 1 hour. The excess dimethylacetamide dimethyl acetal was removed under vacuum and the residue was treated with 70% acetic acid (1.0 mL) at room temperature for 12 hours. After the solvent was removed, the residue was purified on silica gel. Elution with 20% EtOAc/hexanes afforded the desired product as a light yellow solid (15 mg, 68% yield). $^1$H NMR (CDCl$_3$, 300 MHz) δ: 8.40 (broad s, 1H), 7.65-7.33 (m, 8H), 7.13-7.06 (m, 1H), 6.92-6.82 (m, 1H), 5.19 (s, 2H), 2.57 (s, 3H), 1.36 (s, 9H).

The requisite intermediates were prepared as follows a. Preparation of Compound

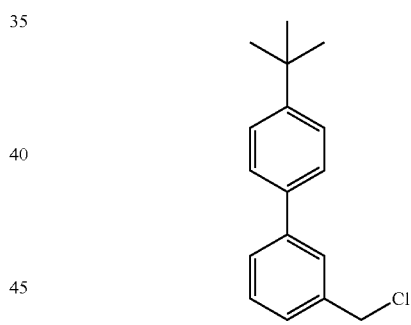

Prepared according to the literature method. See Kaul M, Parhi A K, Zhang Y, LaVoie E J, Tuske S, Arnold E, Kerrigan J E, Pilch D S; J Med Chem. 2012 Nov. 26; 55(22):10160-76.

b. Preparation of Compound

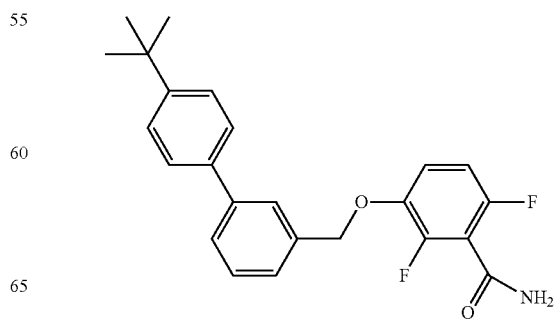

A 10-ml flask was added 4'-(tert-butyl)-3-(chloromethyl)-1,1'-biphenyl (20 mg, 0.08 mmol), 2,6-difluoro-3-hydroxybenzamide (14 mg, 0.08 mmol), K$_2$CO$_3$ (22 mg, 0.16 mmol), and DMF (1.5 mL). The reaction mixture was stirred at 50° C. overnight. After cooling to room temperature, the reaction mixture was diluted with EtOAc and washed with water, brine, and dried over Na$_2$SO$_4$. The organic solvent was removed and the residue was purified on silica gel. Elution with 10% EtOAc/hexanes afforded the desired product as white solid (22 mg, 72% yield). $^1$H NMR (CDCl$_3$, 300 MHz) δ: 7.65-7.33 (m, 8H), 7.09-6.99 (m, 1H), 6.89-6.79 (m, 1H), 5.95 (broad s, 1H), 5.86 (broad s, 1H), 5.19 (s, 2H), 1.37 (s, 9H).

Example 37

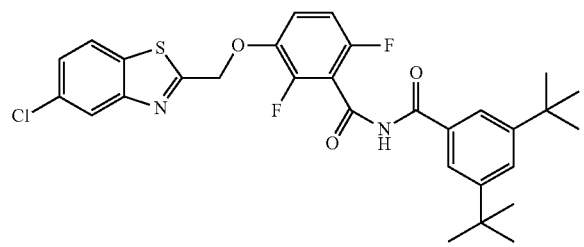 [SMILES: CC(C)(C)c1cc(C(=O)NC(=O)c2c(F)ccc(OCc3nc4cc(Cl)ccc4s3)c2F)cc(C(C)(C)C)c1]

A 2-dram vial was added 3-((5-chlorobenzo[d]thiazol-2-yl)methoxy)-2,6-difluorobenzamide (25 mg, 0.07 mmol), 3,5-di-tert-butylbenzoyl chloride (18 mg, 0.07 mmol), and THF (2 mL). With stirring, NaH (9 mg, 60% in mineral oil, 0.21 mmol) was added. The resulting mixture was stirred at room temperature overnight. The solvent was removed and the residue was purified on silica gel. Elution with 30% EtOAc/hexanes afforded the desired product as white solid (14 mg, 35% yield). $^1$H NMR (CDCl$_3$, 300 MHz) δ: 9.08 (broad s, 1H), 8.02 (d, J=2.1 Hz, 1H), 7.94 (s, 1H), 7.83 (d, J=8.7 Hz, 1H), 7.68 (s, 2H), 7.41 (dd, J=6.7, 1.8 Hz), 7.22-7.14 (m, 1H), 6.94-6.88 (m, 1H), 5.52 (s, 2H), 1.38 (s, 18H).

Example 38

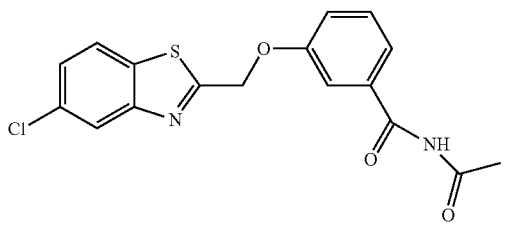 [SMILES: CC(=O)NC(=O)c1cccc(OCc2nc3cc(Cl)ccc3s2)c1]

In a 2-dram vial, a suspension of 3-((5-chlorobenzo[d]thiazol-2-yl)methoxy)benzamide (20 mg, 0.05 mmol) in 1 ml of N,N-dimethylacetamide dimethyl acetal was capped and stirred at 100° C. for 1 hour. The excess dimethylacetamide dimethyl acetal was removed under vacuum and the residue was treated with 70% acetic acid (1.0 mL) at room temperature for 12 hours. After the solvent was removed, the residue was purified on silica gel. Elution with 20% EtOAc/hexanes afforded the desired product as white solid (15 mg, 54% yield). $^1$H NMR (CDCl$_3$, 300 MHz) δ: 8.49 (broad s, 1H), 8.04 (d, J=2.4H), 7.83 (d, J=9 Hz, 1H), 7.56 (s, 1H), 7.45-7.39 (m, 4H), 5.55 (s, 2H), 2.62 (s, 3H).

a. Preparation of Compound

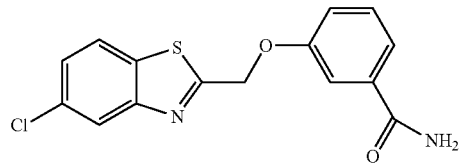 [SMILES: NC(=O)c1cccc(OCc2nc3cc(Cl)ccc3s2)c1]

A 2-dram vial was added 2-(bromomethyl)-5-chlorobenzo[d]thiazole (42 mg, 0.16 mmol), 3-hydroxybenzamide (21 mg, 0.15 mmol), K$_2$CO$_3$ (44 mg, 0.32 mmol), and DMF (0.5 mL). The reaction mixture was stirred at 50° C. overnight. After cooling to room temperature, water was added. The yellow solid was collected by filtration and washed with water. After air drying, the solid was triturated with CH$_2$Cl$_2$. There was obtained the desired product (29 mg, 59%) as yellow solid. $^1$H NMR (DMSO, 300 MHz) δ: 8.19 (d, J=9.0 Hz, 1H), 8.14 (d, J=3.0 Hz, 1H), 8.00 (broad s, 1H), 7.61 (s, 1H), 7.56 (s, 1H), 7.53 (s, 1H), 7.45-7.38 (m, 2H), 7.29-7.25 (m, 1H), 5.68 (s, 2H).

Example 39

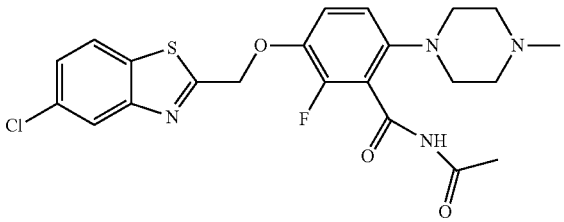 [SMILES: CC(=O)NC(=O)c1c(N2CCN(C)CC2)ccc(OCc2nc3cc(Cl)ccc3s2)c1F]

A suspension of 3-((5-chlorobenzo[d]thiazol-2-yl)methoxy)-2-fluoro-6-(4-methylpiperazin-1-yl)benzamide (25 mg, 0.06 mmol) in 1 ml of N,N-dimethylacetamide dimethyl acetal was stirred at 90° C. for 1 hour. The excess dimethylacetamide dimethyl acetal was removed under vacuum and the residue was treated with 70% acetic acid (1.0 mL) at room temperature for 12 hours. After the solvent was removed, the residue was purified on silica gel. Elution with 10% MeOH/EtOAc afforded the desired product as an off white solid (19 mg, 70% yield.). $^1$H NMR (CDCl$_3$, 300 MHz) δ: 8.98 (broad s, 1H), 8.01 (d, J=2.0 Hz, 1H), 7.81 (d, J=8.8 Hz, 1H), 7.40 (dd, J=6.8, 1.8 Hz), 7.02-6.86 (m, 2H), 5.50 (s, 2H), 3.30 (broad s, 4H), 2.52 (broad s, 4H), 2.57 (s, 3H), 2.35 (s, 3H).

The requisite intermediate was prepared as follows
a. Preparation of Compound

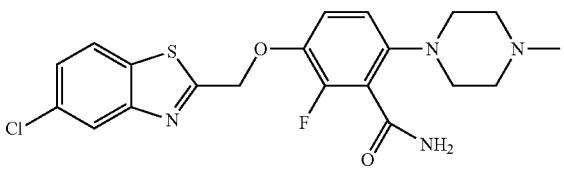 [SMILES: CN1CCN(c2ccc(OCc3nc4cc(Cl)ccc4s3)c(F)c2C(N)=O)CC1]

In a 2-dram vial was added 3-((5-chlorobenzo[d]thiazol-2-yl)methoxy)-2,6-difluorobenzamide (40 mg, 0.11 mmol), and 1-methylpiperazine (0.02 mL), then sealed. The reaction mixture was heated to 125° C. with stirring for 1 hour. After cooling to room temperature, water was added. The resulting solid was collected by filtration. After drying, there was obtained the desired product as a light yellow solid (42 mg, 86% yield). ¹H NMR (CDCl₃, 300 MHz) δ: 8.01 (d, J=2.0 Hz, 1H), 7.82 (d, J=8.8 Hz, 1H), 7.41 (dd, J=6.8, 1.8 Hz), 6.97-6.80 (m, 2H), 6.02 (broad s, 1H), 5.79 (broad s, 5.47 (s, 2H), 3.35-3.29 (m, 4H), 2.57-2.48 (m, 4H), 2.34 (s, 3H).

Example 40

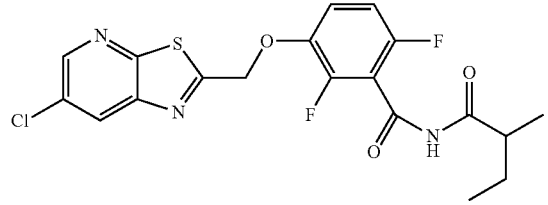 [SMILES: CCC(C)C(=O)NC(=O)c1c(F)ccc(OCc2nc3cc(Cl)cnc3s2)c1F]

A 2-dram vial was added 3-((6-chlorothiazolo[5,4-b]pyridin-2-yl)methoxy)-2,6-difluorobenzamide (25 mg, 0.07 mmol), 2-methylbutanoyl chloride (9 mg, 0.07 mmol), and THF (2 mL) With stirring, NaH (9.0 mg, 60% in mineral oil, 0.21 mmol) was added. The resulting mixture was stirred at 50° C. for 1 hour. The solvent was removed and the residue was purified on silica gel. Elution with 30% EtOAc/hexanes afforded the desired product as off white solid (12 mg, 39% yield). ¹H NMR (CDCl₃, 300 MHz) δ: 8.58 (s, 1H), 8.25 (s, 1H), 8.15 (broad s, 1H), 7.22-7.12 (m, 1H), 6.95-6.86 (m, 1H), 5.48 (s, 2H), 2.81 (m, 1H), 1.76 (m, 1.22 (d, J=6.6 Hz, 3H), 0.98 (t, J=7.5 Hz).

Example 41

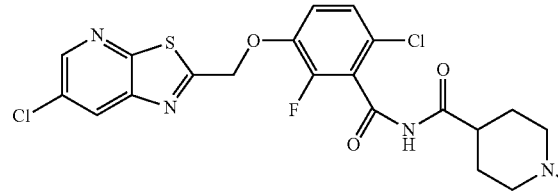

A 25-mL round bottom flask was added 6-chloro-3-((6-chlorothiazolo[5,4-b]pyridin-2-yl)methoxy)-2-fluorobenzamide (200 mg, 0.54 mmol), 1-methylpiperidine-4-carbonyl chloride hydrochloride (200 mg, 1.01 mmol), and THF (4 mL). With stirring, NaH (120 mg, 60% in mineral oil, 3.0 mmol) was added in several portions. After 10 min, a solution of water (20 ml) in THF (1 mL) was added via a syringe. After 10 min, the reaction was completed. It was quenched by a few drop of water, and diluted with CH₂Cl₂. The organic solution was washed with brine and dried over Na₂SO₄. The solvent was removed and the resulting residue was purified by ISCO using 10% MeOH in CH₂Cl₂+1% NH₄OH to afford a beige solid (106 mg, 40% yield). ¹H NMR (CDCl₃, 300 MHz) δ: 8.58 (s, 1H), 8.25 (s, 1H), 7.20-7.07 (m, 2H), 5.52 (s, 2H), 3.05-2.84 (m, 3H), 2.39 (s, 3H), 2.33-1.87 (m, 6H).

The requisite intermediate was prepared as follows a. Preparation of Compound

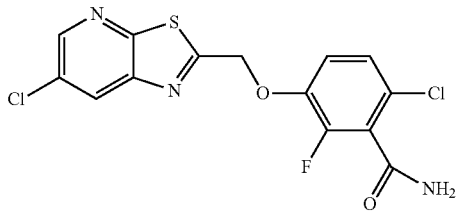 [SMILES: NC(=O)c1c(Cl)ccc(OCc2nc3cc(Cl)cnc3s2)c1F]

A 25-mL round bottom flask equipped with a magnetic stirrer was charged with 6-chloro-2-(chloromethyl)thiazolo[5,4-b]pyridine (326 mg, 1.49 mmol), DMF (4 mL), K₂CO₃ (414 mg, 3.0 mmol), and 6-chloro-2-fluoro-3-hydroxybenzamide (270 mg, 1.42 mmol). The reaction mixture was stirred at room temperature for 12 hours then water was added. The solid was collected by filtration and washed with water. After air drying, the solid was triturated with CH₂Cl₂. There was obtained the desired product (330 mg) as brown solid with 60% yield. ¹H NMR (DMSO, 300 MHz) δ: 8.74 (d, J=2.1 Hz, 1H), 8.70 (d, J=2.1 Hz, 1H), 8.17 (s, 1H), 7.91 (s, 1H), 7.43-7.30 (m, 2H), 5.78 (s, 2H).

Example 42

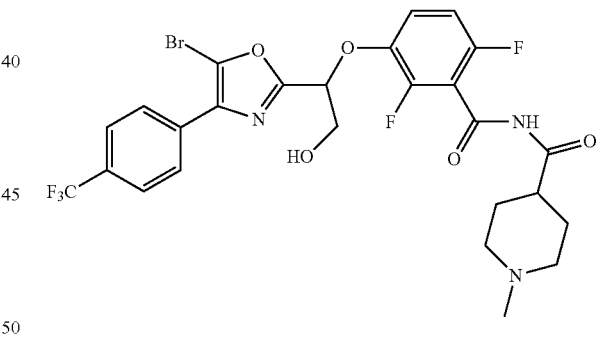

A 15-mL round bottom flask equipped with a magnetic stirrer was charged with 3-(1-(5-bromo-4-(4-(trifluoromethyl)phenyl)oxazol-2-yl)-2-hydroxyethoxy)-2,6-difluorobenzamide (25 mg, 0.04 mmol, 1-methylpiperidine-4-carbonyl chloride hydrochloride (50 mg, 0.25 mmol), and THF (2 mL). With stirring NaH (25 mg, 0.60 mmol, 60% dispersion in mineral oil) was added. The resulting reaction mixture was stirred for 10 minutes, then a solution of water (4 μl) in THF (0.5 mL) was added via a syringe. After 10 min, the reaction was completed. it was quenched by the addition of few drops of water, and diluted with dichloromethane. The organic phase was separated, washed with brine and dried over Na₂SO₄. The solvent was removed in vacuo, and the resulting residue was purified by ISCO using 10% MeOH in CH$_2$Cl$_2$+1% NH$_4$OH to afford an off white solid (11 mg, 40% yield). LC-MS: 632, 634 (M+1).

The requisite intermediates were prepared as follows a. Preparation of Compound

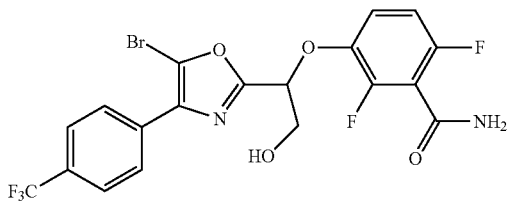 [SMILES: NC(=O)c1c(F)ccc(OC(CO)c2nc(-c3ccc(C(F)(F)F)cc3)c(Br)o2)c1F]

Prepared according to the literature method:

Haydon, David John; Czaplewski, Lloyd George; Stokes, Neil Robert; Davies, David; Collins, Ian; Palmer, James T.; Mitchell, Jeffrey Peter; Pitt, Gary Robert William; Offermann, Daniel PCT Int. Appl. (2012), WO2012142671A1 2012 1026.

Example 43

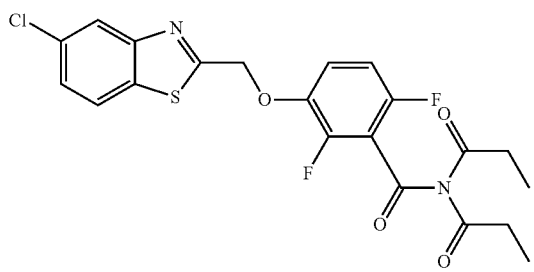 [SMILES: CCC(=O)N(C(=O)CC)C(=O)c1c(F)ccc(OCc2nc3cc(Cl)ccc3s2)c1F]

In a round bottom flask 3-((5-chlorobenzo[d]thiazol-2-yl)methoxy)-2,6-difluorobenzamide (35 mg, 0.1 mmol) was dissolved in 2 ml of dry THF, and the solution was cooled to 0° C. under nitrogen. This was followed by portion wise addition of NaH (8 mg, 0.2 mmol, 60% dispersion in mineral oil). The mixture was stirred at 0° C. for 10 minutes and at room temperature for 45 minutes. The mixture was cooled to 0° C., and a solution of propionyl chloride (8.0 µl, 0.1 mmol) in 1 ml of THF was added drop-wise. The resulting reaction mixture was stirred at 0° C. for 10 minutes and at room temperature for 4 hours. After completion of the reaction, it was quenched by the addition of few drops of 1N HCl, and diluted with ethyl acetate. The organic phase was separated, washed successively with sat. NaHCO$_3$, brine and dried. The solvent was removed in vacuo, and the resulting residue was purified by ISCO using 20% EtOAc in hexane as the elutant to afford the pure product as white solid (8 mg, 18% yield) along with mono acetylated product and recovered starting material. $^1$H NMR (300 MHz, CDCl$_3$) δ: 8.047 (s, 1H), 7.85 (d, J=8.7 Hz, 1H), 7.43 (dd, J=8.7, 2.1 Hz, 1H), 7.22-7.16 (m, 1H), 6.93-6.87 (m, 1H), 5.53 (s, 2H), 2.77 (qt, 4H), 1.20 (t, 6H).

Example 44

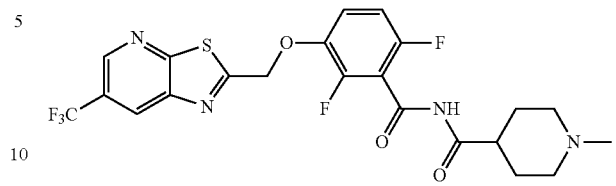

A 25-mL round bottom flask equipped with a magnetic stirrer was charged with 2,6-difluoro-3-((6-(trifluoromethyl)thiazolo[5,4-b]pyridin-2-yl)methoxy)benzamide (300 mg, 0.77 mmol, 1-methylpiperidine-4-carbonyl chloride hydrochloride (50 mg, 0.25 mmol) (300 mg, 1.51 mmol), and THF (6 mL). With stirring NaH (180 mg, 4.5 mmol, 60% dispersion in mineral oil) was added portionwise over 5 min. The resulting reaction mixture was stirred for 10 minutes, then a solution of water (30 ul) in THF (2 mL) was added via a syringe dropwise over 5 min. The reaction mixture changed from suspension to a brown solution. After completion of the reaction, it was quenched by the addition of few drops of water, and diluted with dichloromethane. The organic phase was separated, washed with brine and dried over Na$_2$SO$_4$. The solvent was removed in vacuo, and the resulting residue was purified by ISCO using 10% MeOH in CH$_2$Cl$_2$+1% NH$_4$OH to afford a light brown solid, which was triturated with EtOAc to give a beige solid (218 mg, 55% yield). $^1$H NMR (300 MHz, CDCl$_3$) δ: 8.58 (s, 1H), 8.31 (broad s, 1H), 8.24 (s, 1H), 7.24-7.14 (m, 1H), 6.94-6.87 (m, 1H), 5.50 (s, 2H), 2.94-2.80 (m, 3H), 2.28 (s, 3H), 2.10-1.74 (m, 6H). LC-MS: 515 (M+1).

The requisite intermediates were prepared as follows a. Preparation of Compound

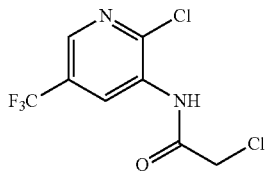 [SMILES: O=C(CCl)Nc1cc(C(F)(F)F)cnc1Cl]

A 100-mL round bottom flask equipped with a magnetic stirrer was charged with 2-chloro-5-(trifluoromethyl)pyridine-3-amine (1.0 g, 5.1 mmol), CH$_2$Cl$_2$ (15 mL), TEA (1.42 ml, 10.2 mmol). The reaction mixture was cooled under ice-bath and chloroacetyl chloride (0.81 ml, 10.2 mmol) was slowly added. The reaction mixture was stirred at room temperature for 2 hours. The solvent was removed under vacuum. The residue was purified by column chromatography using 20% EtOAc/hexane to afford the desired product as off-white solid (1.22 g, 88% yield).). $^1$H NMR (300 MHz, CDCl$_3$) δ: 9.05 (s, 2H), 8.44 (s, 1H), 4.27 (s, 2H).

b. Preparation of Compound

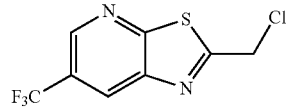

A 100-mL round bottom flask equipped with a magnetic stirrer was charged with 2-chloro-N-(2-chloro-5-(trifluoromethyl)pyridine-3-yl)acetamide (1.22 g, 4.47 mmol), P₅S₁₀ (750 mg,), and toluene (20 mL). The resulting mixture was refluxed for 30 minutes. The reaction mixture was cooled to room temperature and the solids were filtered off. The solvent was removed and the crude product was purified by column chromatography using hexanes to 5% EtOAc/hexane to afford the pure product as a light yellow solid (935 mg, 84% yield). ¹H NMR (300 MHz, CDCl₃) δ: 8.90 (s, 1H), 8.50 (s, 1H), 4.98 (s, 2H). LC-MS: 253 (M+1).

c. Preparation of Compound

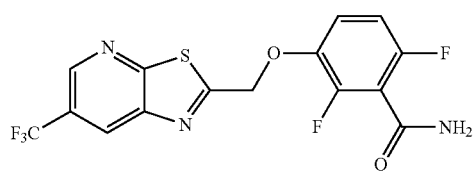 [SMILES: NC(=O)c1c(F)ccc(OCc2nc3cc(C(F)(F)F)cnc3s2)c1F]

A 25-mL round bottom flask equipped with a magnetic stirrer was charged with 2-(chloromethyl)-6-(trifluoromethyl)thiazolo[5,4-b]pyridine (350 mg, 1.39 mmol), DMF (2.0 mL), NaHCO₃ (277 mg, 3.30 mmol), and 2,6-difluoro-3-hydroxybenzamide (230 mg, 1.32 mmol). The reaction mixture was heated at 50° C. overnight. After cooling to room temperature, water was added to the reaction mixture and the precipitate was collected by filtration to give a brown solid. After drying, the crude product was triturated with CH₂Cl₂ to afford the desired product as light brown solid in high purity (380 mg, 71% yield). ¹H NMR (300 MHz, DMSO-d₆) δ: 9.05 (s, 1H), 8.93 (s, 1H), 8.17 (bs, 1H), 7.89 (bs, 1H), 7.45-7.37 (m, 1H), 7.11 (m, 1H), 5.77 (s, 2H). LC-MS: 390 (M+1).

Example 45

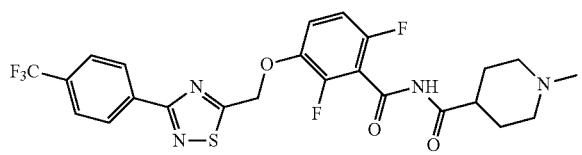 [SMILES: CN1CCC(C(=O)NC(=O)c2c(F)ccc(OCc3nc(-c4ccc(C(F)(F)F)cc4)ns3)c2F)CC1]

A 25-mL round bottom flask was added amide 2,6-difluoro-3-((3-(4-(trifluoromethyl)phenyl)-1,2,4-thiadiazol-5-yl)methoxy)benzamide (137 mg, 0.33 mmol), 1-methyl-piperidine-4-carbonyl chloride hydrochloride (137 mg, 0.69 mmol), and THF (3.0 mL). With stirring, NaH (80 mg, 60% in mineral oil, 2.0 mmol) was added in several portions. After 5 minutes, a solution of water (4 μl) in THF (0.5 mL) was added via a syringe. After 10 minutes, the reaction was completed. It was quenched by a few drop of water, and diluted with CH₂Cl₂. The organic solution was washed with brine and dried over Na₂SO₄. The solvent was removed and the resulting residue was purified by silica gel ISCO chromatography using 10% MeOH in DCM+1% NH₄OH to afford an off white solid (115 mg, 65% yield). ¹H NMR (DMSO-d₆, 300 MHz) δ 11.6 (s, 1H) 8.47 (d, J=6.0 Hz, 2H), 7.98 (d, J=6.0 Hz, 2H), 7.58 (m, 1H), 7.20 (m, 2H), 5.91 (s, 2H), 2.84 (m, 2H), 2.17 (s, 3H), 2.03-1.7 (m, 6H).

The following requisite intermediate was prepared according to the following literature method.

a. Preparation of Compound

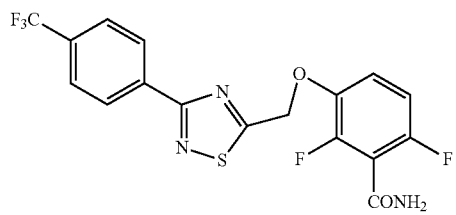 [SMILES: NC(=O)c1c(F)ccc(OCc2nc(-c3ccc(C(F)(F)F)cc3)ns2)c1F]

WO2009037485 A1 by Haydon, David John; Collins, Ian; Czaplewski, Lloyd George

Example 46

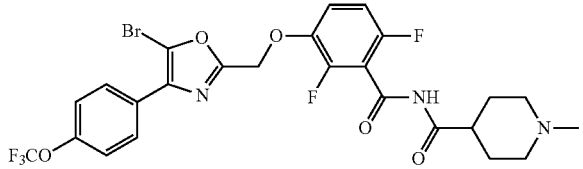 [SMILES: CN1CCC(C(=O)NC(=O)c2c(F)ccc(OCc3nc(-c4ccc(OC(F)(F)F)cc4)c(Br)o3)c2F)CC1]

A 15-mL round bottom flask equipped with a magnetic stirrer was charged with amide 3-((5-bromo-4-(4-(trifluoromethoxy)phenyl)oxazol-2-yl)methoxy)-2,6-difluorobenzamide (130 mg, 0.21 mmol, acyl chloride (130 mg, 0.66 mmol), and THF (3 mL). With stirring NaH (60 mg, 1.5 mmol, 60% dispersion in mineral oil) was added. The resulting reaction mixture was stirred for 5 minutes, then a solution of water (4 μL) in THF (0.5 ML) was added via a syringe. After 10 minutes, the reaction was completed. The reaction was quenched by the addition of few drops of water, and diluted with dichloromethane. The organic phase was separated, washed with brine and dried over Na₂SO₄. The solvent was removed under reduced pressure, and the resulting residue was purified by silica gel ISCO chromatography using 10% MeOH in DCM+1% NH₄OH to afford a white solid (104 mg, 64% Yield). 1H NMR (CDCl₃, 300 MHz) δ 7.97 (d, J=6.0 Hz, 2H), 7.28 (d, J=6.0 Hz, 2H), 7.24 (m, 1H), 6.95 (m, 1H), 5.19 (s, 2H), 3.05 (m, 3H), 2.40 (s, 3H), 2.13-1.7 (m, 6H).

The requisite intermediates were prepared as follows:

a. Preparation of Compound

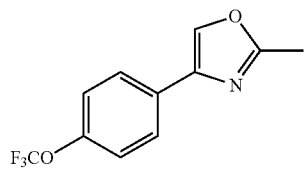 [SMILES: Cc1nc(-c2ccc(OC(F)(F)F)cc2)co1]

A mixture of 4-trifluoromethoxyphenacyl bromide (700 mg, 2.47 mmol) and acetamide (360 mg, 6.1 mmol) was heated to 110° C. for 12 hours. When the reaction was complete, water was added and the mixture was washed with ethyl acetate (3×100 mL) The combined organic layers were washed with water, dried with Na₂SO₄, filtered and concentrated. The crude mixture was purified by silica gel ISCO chromatography using 20% EtOAC/hexane to give an off white solid (420 mg, 70% yield). 1H NMR (CDCl3, 300 MHz) δ 7.82 (s, 1H), 7.74 (d, J=6.0 Hz, 2H), 7.25 (d, J=6.0 Hz, 2H), 2.53 (s, 3H).

b. Preparation of Compound

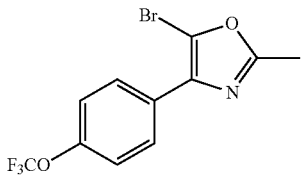

To a solution of 2-methyl-4-(4-(trifluoromethoxy)phenyl)oxazole (316 mg, 1.48 mmol) in AcOH (7.0 mL) was added NBS (315 mg, 1.77 mmol) and the resulting mixture was stirred at room temperature for 4 hours. After the completion of the reaction, acetic acid was removed from the reaction mixture and was diluted with ethyl acetate. The mixture was then washed with 1N NaOH and brine, dried over $Na_2SO_4$, filtered and concentrated. The residue was purified by silica gel ISCO chromatography to give the product as off white solid (280 mg, 59% yield). LC/MS (M+H): 323.3.

c. Preparation of Compound

To a solution of 5-bromo-2-methyl-4-(4-(trifluoromethoxy)phenyl)oxazole (280 mg, 0.869 mmol) in CCl4 (5.0 mL) was added NBS (178 mg, 1.04 mmol). The resulting mixture was heated under light for 2 hours. The mixture was filtered, concentrated under reduced pressure and purified by silica gel ISCO chromatography to give the product (300 mg) along with dibromo product and recovered starting material which was used for the next step without further purification.

d. Preparation of Compound

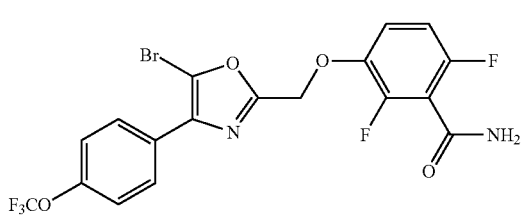 [SMILES: NC(=O)c1c(F)ccc(OCc2nc(-c3ccc(OC(F)(F)F)cc3)c(Br)o2)c1F]

A 25-mL round bottom flask equipped with a magnetic stirrer was charged with 5-bromo-2-(bromomethyl)-4-(4-(trifluoromethoxy)phenyl)oxazole (300 mg, 0.75 mmol), DMF (3.0 mL), $NaHCO_3$ (170 mg, 2.02 mmol), and 2,6-difluoro-3-hydroxybenzamide (150 mg, 1.16 mmol). The reaction mixture was stirred at room temperature for 12 hours then water was added. The solid was collected by filtration and washed with water. After air drying, the solid was triturated with $CH_2Cl_2$. There was obtained the desired product (140 mg, 43% yield) as white solid. $^1$H NMR (DMSO, 300 MHz) δ: 8.17 (s, 1H), 8.02 (d, J=6.0 Hz, 2H), 7.90 (s, 1H), 7.54 (d, J=6.0 Hz, 2H), 7.45-7.37 (m, 1H), 7.18-7.11 (m, 1H), 5.42 (s, 2H).

Example 47

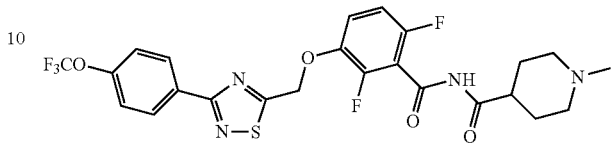

A 25-mL round bottom flask was added 2,6-difluoro-3-((3-(4-(trifluoromethoxy)phenyl)-1,2,4-thiadiazol-5-yl)methoxy)benzamide (100 mg, 0.23 mmol), 1-methylpiperidine-4-carbonyl chloride hydrochloride (100 mg, 0.51 mmol), and THF (5.0 mL). With stirring, NaH (60 mg, 60% in mineral oil, 1.5 mmol) was added in several portions. After 5 minutes, a solution of water (4 μl) in THF (0.5 mL) was added via a syringe. After 10 minutes, the reaction was completed. It was quenched by a few drop of water, and diluted with $CH_2Cl_2$ The organic solution was washed with brine and dried over $Na_2SO_4$. The solvent was removed and the resulting residue was purified by silica gel ISCO chromatography using EtOAc to afford a white solid (80.5 mg, 62% yield). $^1$H NMR (CDCl$_3$, 300 MHz) δ: 8.4 (d, J=6.0 Hz, 2H), 7.4 (d, J=6.0 Hz, 2H), 7.20 (m, 1H), 7.0 (m, 1H), 5.62 (s, 2H), 3.05-2.94 (m, 3H), 2.38 (s, 3H), 2.23-1.87 (m, 6H).

The following requisite intermediate was prepared from following literature method.

a. Preparation of Compound

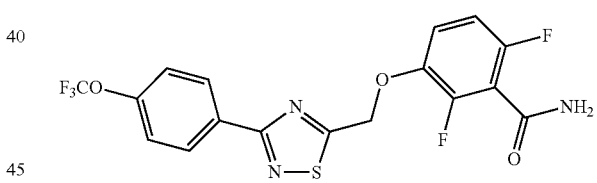

WO2009037485 A1 by Haydon, David John; Collins, Ian; Czaplewski, Lloyd George

Example 48

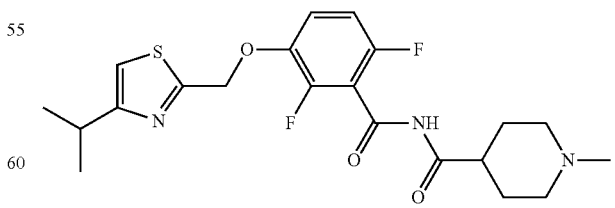

A 25-mL round bottom flask was added 2,6-difluoro-3-((4-isopropylthiazol-2-yl)methoxy)benzamide (70 mg, 0.22 mmol), 1-methylpiperidine-4-carbonyl chloride hydrochloride (70 mg, 0.35 mmol), and THF (4 mL). With stirring, NaH (45 mg, 60% in mineral oil, 1.1 mmol) was added in several portions. After 10 minutes, a solution of water (4 μl) in THF (0.5 mL) was added via a syringe. After 10 minutes, the reaction was completed. It was quenched by a few drop of water, and diluted with $CH_2Cl_2$. The organic solution was washed with brine and dried over $Na_2SO_4$. The solvent was removed and the resulting residue was purified by silica gel ISCO chromatography using EtOAc to afford a white solid (45 mg, 46% yield). $^1$H NMR ($CDCl_3$, 300 MHz) δ: 7.18 (m, 1H), 7.9 (s, 1H), 7.83 (m, 1H), 5.37 (s, 2H), 3.08 (m, 1H), 3.05-2.94 (m, 3H), 2.38 (s, 3H), 2.23-1.87 (m, 6H), 1.30 (s, 3H), 1.28 (s, 3H).

The requisite intermediates were prepared as follows
a. Preparation of

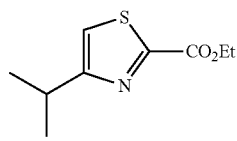

A mixture of 1-bromo-3-methylbutan-2-one (1.1 g, 6.66 mmol), ethyl thioxamate (600 mg, 4.51 mmol) in 5.0 mL ethanol was refluxed overnight. After the completion of the reaction the solvent was removed and the crude mixture was dissolved in ethyl acetate. The organic layer was washed with water, brine and was dried under sodium sulfate. Evaporation of the solvent produced the desired product mixed with impurities which was used for the next step without further purification (400 mg, 30% yield).
b. Preparation of

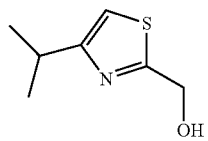

To a solution of ethyl 4-isopropylthiazole-2-carboxylate (400 mg, 2.0 mmol) in EtOH (5.0 mL) at room temperature was added $LiBH_4$ (100 mg, 4.6 mmol). After stirring for 120 minutes, EtOH was evaporated, and the residue was partitioned between $CH_2Cl_2$ and 1N HCl. The organic phase was dried ($Na_2SO_4$) and concentrated to give crude which was purified by silica gel ISCO chromatography using 50% EtOAC in hexane to give the desired product (140 mg, 44% yield) as white solid in very purity high. $^1$H NMR ($CDCl_3$, 300 MHz) δ: 6.89 (s, 1H), 4.97 (s, 2H), 3.12 (m, 1H), 1.37 (s, 3H), 1.34 (s, 3H).
c. Preparation of

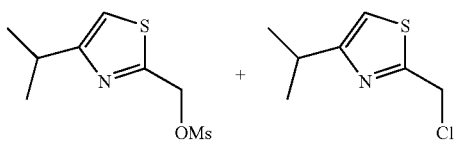

A 25-mL round bottom flask equipped with a magnetic stirrer under nitrogen was charged with (4-isopropylthiazol-2-yl)methanol (120 mg, 0.764 mmol), $CH_2Cl_2$ (4.0 mL), and triethylamine (0.12 ml). Methanesulfonyl chloride (0.115 mL, 1.5 mmol) was added via a syringe over 1 minute. The resulting reaction mixture was stirred at room temperature overnight. The reaction mixture was concentrated under reduced pressure to afford the crude product as a mixture of chloride and mesylate (125 mg), which was used without further purification.

d. Preparation of

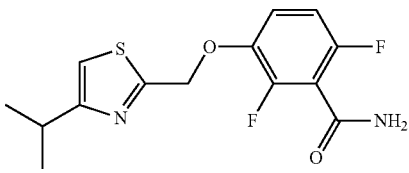 [SMILES: CC(C)c1csc(COc2ccc(F)c(C(N)=O)c2F)n1]

A 25-mL round bottom flask equipped with a magnetic stirrer was charged with mixture of 2-(chloromethyl)-4-isopropylthiazole and (4-isopropylthiazol-2-yl)methyl methanesulfonate (80 mg, 0.34 mmol), DMF (3.0 mL), $NaHCO_3$ (80 mg, 0.95 mmol), and 2,6-difluoro-3-hydroxybenzamide (80 mg, 0.46 mmol). The reaction mixture was stirred at room temperature for 12 hours then water was added. The solid was collected by filtration and washed with water. After air drying, the solid was triturated with $CH_2Cl_2$. There was obtained the desired product (60 mg) as white solid with 75% yield. $^1$H NMR (DMSO, 300 MHz) δ: 8.19 (s, 1H), 7.90 (s, 1H), 7.42-7.37 (m, 2H), 7.17-7.11 (m, 1H), 5.50 (s, 2H), 3.07 (m, 1H), 1.28 (s, 3H), 1.27 (s, 3H).

Example 49

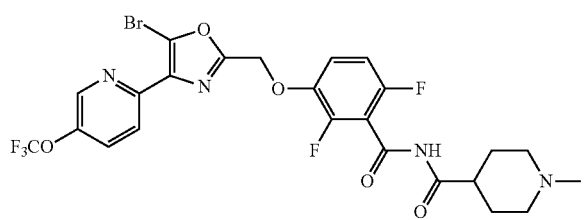 [SMILES: CN1CCC(C(=O)NC(=O)c2c(F)ccc(OCc3nc(-c4ccc(OC(F)(F)F)cn4)c(Br)o3)c2F)CC1]

A 25-mL round bottom flask was added 3-((5-bromo-4-(5-(trifluoromethyl)pyridin-2-yl)oxazol-2-yl)methoxy)-2,6-difluorobenzamide (300 mg, 0.63 mmol), 1-methylpiperidine-4-carbonyl chloride hydrochloride (300 mg, 1.52 mmol), and THF (15 mL). With stirring, NaH (180 mg, 60% in mineral oil, 4.5 mmol) was added in several portions. After 5 minutes, a solution of water (10 μl) in THF (1 mL) was added via a syringe. After 10 minutes, the reaction was completed. It was quenched by a few drop of water, and diluted with $CH_2Cl_2$. The organic solution was washed with brine and dried over $Na_2SO_4$. The solvent was removed and the resulting residue was purified by silica gel ISCO chromatography using EtOAc to afford a white solid (274 mg, 72% yield). $^1$H NMR ($CDCl_3$, 300 MHz) δ: 8.98 (s, 1H), 8.10-8.0 (m, 2H), 7.28 (m, 1H), 6.9 (m, 1H), 5.24 (s, 2H), 3.01-2.86 (m, 3H), 2.34 (s, 3H), 2.2-1.87 (m, 6H).

The requisite intermediates were prepared as follows a. Preparation of Compound

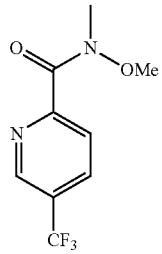 [SMILES: CON(C)C(=O)c1ccc(C(F)(F)F)cn1]

The reaction mixture of benzoic acid (1.2 g, 6.3 mmol), SOCl$_2$ (5 mL) in a sealed tube was heated to 80° C. for 2 h. The solvent was removed and triturated with CH$_2$Cl$_2$ 2 times. The crude chloride was added with CH$_2$Cl$_2$ (20 mL) and cooled to −78° C. under N$_2$, then triethylamine (2.63 mL, 18.9 mmol) was added, followed by N,O-dimethylhydroxylamine (737 mg, 7.56 mmol). The mixture was allowed to warm to room temperature and continuously stirred overnight. The reaction mixture was added CH$_2$Cl$_2$ (100 mL) and then washed by 1N HCl solution, NaHCO$_3$ and brine. The organic layer was dried over Mg$_2$SO$_4$ and evaporated. The crude product was purified by column (0-30% EtOAc/Heptane) to give the title compound (1.38 g, 94%) as a light brown liquid.

b. Preparation of Compound

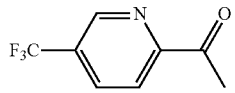

To a solution of N-methoxy-N-methyl-5-(trifluoromethyl) picolinamide (1.38 g, 5.9 mmol) in 15 mL of THF was slowly added MeMgBr (3M in ether, 2.35 mL, 7.8 mmol) at 0° C. under nitrogen. The reaction mixture was then warmed up to room temperature and stirred for 2 hours. After the completion, the reaction was quenched by addition of 20 mL 1N HCl. The reaction mixture was extracted with ethyl acetate and combined organic layer was washed with brine, dried over Na$_2$SO$_4$ to afford the product (1.0 g, 90% Yield) in high purity, which was used in the subsequent step without further purification. $^1$H NMR (CDCl$_3$, 300 MHz) δ: 8.97 (s, 1H), 8.18-8.05 (m, 2H), 2.78 (s, 3H).

c. Preparation of Compound

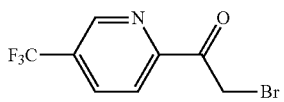

The reaction mixture of 1-(5-(trifluoromethyl)pyridin-2-yl)ethan-1-one (916 mg, 4.85 mmol), bromine (0.25 mL, 4.85 mmol) and 5 mL acetic acid in a sealed tube was heated at 75° C. for one hour. The reaction changed from red solution to yellow suspension. The solvent was removed to give the crude product (1.35, 100% yield), which was used for the next step without further purification.

d. Preparation of Compound

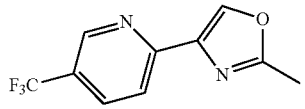 [SMILES: Cc1nc(-c2ccc(C(F)(F)F)cn2)co1]

A mixture of 2-bromo-1-(5-(trifluoromethyl)pyridin-2-yl) ethan-1-one (1.23 g, 4.59 mmol) and acetamide (2.71 g, 45.9 mmol) in acetic acid (20 mL) was heated to 150° C. for 2 hours. When the reaction was complete, the solvent was removed and the residue was partitioned between ethyl acetate and water. The combined organic layers were washed with brine, dried over Na$_2$SO$_4$, and concentrated. The crude mixture was purified by silica gel ISCO chromatography using EtOAC/hexane to give a yellow solid (493 mg, 47% yield). LC/MS: 228 (M+H).

e. Preparation of Compound

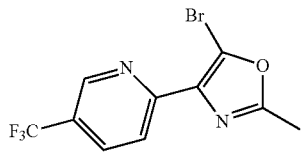 [SMILES: Cc1nc(-c2ccc(C(F)(F)F)cn2)c(Br)o1]

A reaction mixture of 2-methyl-4-(5-(trifluoromethyl) pyridin-2-yl)oxazole (430 mg, 1.89 mmol), Br$_2$ (0.29 mL, 5.67 mmol) in CH$_2$Cl$_2$ (10 mL) was stirred at room temperature for 12 hours in a sealed tube. After the completion of the reaction, the solvent was removed and the residue was diluted with ethyl acetate. The ethyl acetate solution was washed with brine, dried over Na$_2$SO$_4$, and concentrated. The residue was purified by silica gel ISCO chromatography to give off white solid (530 mg mg, 92% yield). $^1$H NMR (CDCl$_3$, 300 MHz) δ: 8.94 (s, 1H), 8.05-7.98 (m, 2H), 2.55 (s, 3H).

f. Preparation of Compound

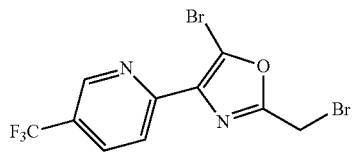 [SMILES: FC(F)(F)c1ccc(-c2nc(CBr)oc2Br)nc1]

To a solution of 5-bromo-2-methyl-4-(5-(trifluoromethyl) pyridin-2-yl)oxazole (530 mg, 1.73 mmol) in CCl$_4$ (10 mL) was added NBS (462 mg, 2.60 mmol). The resulting mixture was heated under light for 2 hours. After cooling to room temperature, hexanes was added. The solid was removed by filtration and the filtrate was concentrated under reduced pressure and purified by silica gel ISCO chromatography to give the pure product (385 mg, 58% yield). $^1$H NMR (CDCl$_3$, 300 MHz) δ: 8.96 (s, 1H), 8.07-8.01 (m, 2H), 4.91 (s, 2H).

g. Preparation of Compound

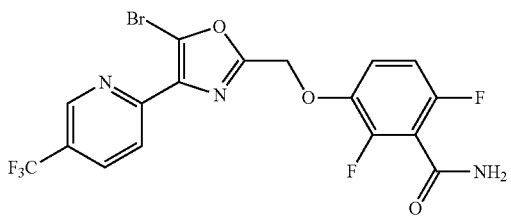 [SMILES: NC(=O)c1c(F)ccc(OCc2nc(-c3ccc(C(F)(F)F)cn3)c(Br)o2)c1F]

A 25-mL round bottom flask was charged with 5-bromo-2-(bromomethyl)-4-(5-(trifluoromethyl)pyridin-2-yl)oxazole (386 mg, 1.0 mmol), DMF (5.0 mL), K$_2$CO$_3$ (276 mg, 2.0 mmol), and phenol (173 mg, 1.0 mmol). The reaction mixture was stirred at 50° C. for 4 hours. The reaction mixture was diluted with EtOAc, washed with water, 10% LiCl, brine, dried over Na$_2$SO$_4$, concentrated, and purified on silica gel. Elution with 70% EtOAc/hexanes afforded the title compound as off white solid (376 mg, 78% yield). $^1$H NMR (DMSO-d$_6$, 300 MHz) δ: 9.1 (s, 1H), 8.4 (d, 2H), 8.2 (s, 1H), 8.15 (d, 2H), 7.95 (s, 1H), 7.42 (m, 1H), 7.18 (m, 2H), 5.45 (s, 2H).

Example 50

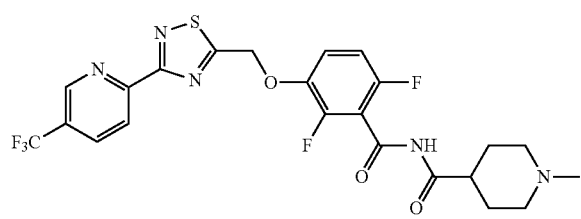 [SMILES: CN1CCC(C(=O)NC(=O)c2c(F)ccc(OCc3nc(-c4ccc(C(F)(F)F)cn4)ns3)c2F)CC1]

A 25-mL round bottom flask was added 2,6-difluoro-3-((3-(5-(trifluoromethyl)pyridin-2-yl)-1,2,4-thiadiazol-5-yl)methoxy)benzamide (100 mg, 0.24 mmol), 1-methylpiperidine-4-carbonyl chloride hydrochloride (100 mg, 0.51 mmol), and THF (4 mL). With stirring, NaH (60 mg, 60% in mineral oil, 1.5 mmol) was added in several portions. After 5 minutes, a solution of water (10 μl) in THF (1 mL) was added via a syringe. After 10 minutes, the reaction was completed. It was quenched by a few drop of water, and diluted with CH$_2$Cl$_2$. The organic solution was washed with brine and dried over Na$_2$SO$_4$. The solvent was removed and the resulting residue was purified by silica gel ISCO chromatography using EtOAc to afford a white e solid (79 mg, 61% yield). $^1$H NMR (CDCl$_3$, 300 MHz) δ: 9.05 (s, 1H), 8.5 (d, 1H), 8.1 (d, 1H), 7.2 (m, 1H), 6.9 (m, 1H), 5.6 (s, 2H), 3.01-2.86 (m, 3H), 2.34 (s, 3H), 2.2-1.87 (m, 6H).

The requisite intermediates were prepared as follows
a. Preparation of Compound

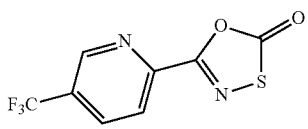

A mixture of 5-trifluoromethyl-2-pyridylcarboxamide (1.78 g, 9.36 mmol), chlorosulfinyl chloride (4 mL, 46.8 mmol) in 30 mL toluene was heated at 90° C. under nitrogen for 7 hours. After completion of the reaction, the reaction mixture was cooled to room temperature, diluted with CH$_2$Cl$_2$. The organic solution was washed with sat. NaHCO$_3$, and brine, and dried over Na$_2$SO$_4$. Evaporation of the solvent and purification of the crude material by silica gel ISCO chromatography using 20% Ethyl acetate in hexane afforded the pure product as white solid (1.92 g, 83% yield). $^1$H NMR (CDCl$_3$, 300 MHz) δ: 9.03 (s, 1H), 8.16 (m, 2H).

b. Preparation of Compound

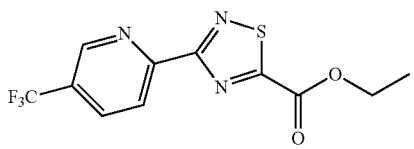 [SMILES: CCOC(=O)c1nc(-c2ccc(C(F)(F)F)cn2)ns1]

A reaction mixture of 5-(5-(trifluoromethyl)pyridin-2-yl)-1,3,4-oxathiazol-2-one (1.0 g, 4.03 mmol) and ethyl cyanoformate (2.0 mL, 20.2 mmol) in 1,2-dichlorobenzene (10 mL) was heated at 160° C. for 20 hours in a sealed tube. After cooling to room temperature, the reaction mixture was purified by column chromatography to give 387 mg (32%) of pure product as a yellow solid. LC/MS: 304 (M+H).

c. Preparation of Compound

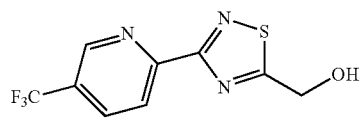 [SMILES: OCc1nc(-c2ccc(C(F)(F)F)cn2)ns1]

To a solution of 3-(5-(trifluoromethyl)pyridin-2-yl)-1,2,4-thiadiazole-5-carboxylate (337 mg, 1.11 mmol) in MeOH (2 mL) at room temperature was added NaBH$_4$ (127 mg, 5.82 mmol). After stirring for 10 minutes, MeOH was evaporated, and the residue was partitioned between CH$_2$Cl$_2$ and 1N HCl. The organic phase was dried (Na$_2$SO$_4$) and concentrated to give 260 mg as a beige solid, which was used as such without further purification.

d. Preparation of Compound

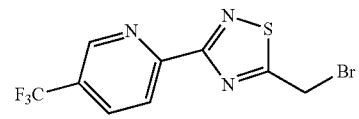 [SMILES: FC(F)(F)c1ccc(-c2nsc(CBr)n2)nc1]

A mixture of (3-(5-(trifluoromethyl)pyridin-2-yl)-1,2,4-thiadiazol-5-yl)methanol (260 mg, 1.0 mmol), PBr3 (0.14 mL, 1.5 mmol) in 10 mL toluene was heated at 120° C. in a sealed tube for 20 minutes. After completion of the reaction, the reaction mixture was cooled to room temperature and diluted with CH$_2$Cl$_2$. The organic solution was washed with sat. NaHCO$_3$, brine, dried with Na$_2$SO$_4$, and concentrated to give (254 mg, 79% yield) as a beige solid, which is pure enough to be used for the next step without further purification. $^1$H NMR (CDCl$_3$, 300 MHz) δ: 9.04 (s, 1H), 8.48 (d, J=8.1 Hz, 1H), 8.11 (d, J=8.1 Hz, 1H), 5.05 (s, 2H).

e. Preparation of Compound

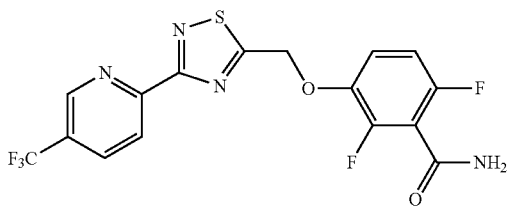 [SMILES: NC(=O)c1c(F)ccc(OCc2nc(-c3ccc(C(F)(F)F)cn3)ns2)c1F]

A 25-mL round bottom flask equipped with a magnetic stirrer, a condenser and a nitrogen in/outlet adapter was charged with 5-(bromomethyl)-3-(5-(trifluoromethyl)pyridin-2-yl)-1,2,4-thiadiazole (250 mg, 0.77 mmol), DMF (5.0 mL), K$_2$CO$_3$ (212 mg, 1.5 mmol), and phenol (133 mg, 0.77 mmol). The reaction mixture was stirred at room temperature overnight. The reaction mixture was diluted with EtOAc, washed with water, 10% LiCl, brine, dried over Na$_2$SO$_4$, concentrated, and purified on silica gel. Elution with 70% EtOAc/hexanes afforded the title compound as beige solid (160 mg, 50% yield). $^1$H NMR (DMSO, 300 MHz) δ: 9.2 (s, 1H), 8.50 (m, 2H), 8.22 (s, 1H), 7.95 (s, 1H), 7.50 (m, 1H), 7.21 (m, 1H), 5.89 (s, 2H).

Example 51

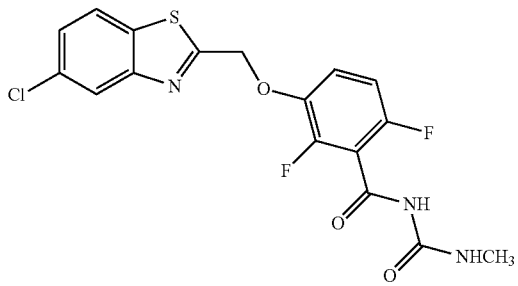 [SMILES: CNC(=O)NC(=O)c1c(F)ccc(OCc2nc3cc(Cl)ccc3s2)c1F]

To a solution of 3-((5-chlorobenzo[d]thiazol-2-yl)methoxy)-2,6-difluorobenzoyl chloride (30 mg, 0.08 mmol), Hunig base (0.030 ml) in DCM (2.0 ml) was added 1-methylurea (12 mg, 0.16 mmol) and the reaction mixture was stirred at room temperature for 1 hour. Evaporation of solvent and purification using ISCO produced the desired compound as white solid (22 mg, 69% yield). LC/MS: 412 (M+H).

Example 52

The following can illustrate representative pharmaceutical dosage forms, containing a compound of formula I ('Compound X') or a pharmaceutically acceptable salt thereof, for therapeutic or prophylactic use in humans. The tablets can optionally comprise an enteric coating.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

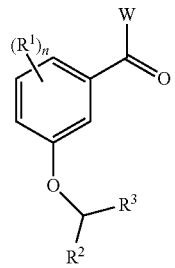

(I)

wherein:
each $R^1$ is independently selected from hydrogen, halo, cyano, nitro, $(C_1-C_6)$alkyl, $(C_1-C_6)$alkoxy, $(C_1-C_6)$alkanoyl, $(C_1-C_6)$alkoxycarbonyl, $(C_1-C_6)$alkanoyloxy, aryl, heteroaryl, heterocycle, and $NR^eR^f$, wherein each $(C_1-C_6)$alkyl, $(C_1-C_6)$alkoxy, $(C_1-C_6)$alkanoyl, $(C_1-C_6)$alkoxycarbonyl, $(C_1-C_6)$alkanoyloxy, aryl, heteroaryl, and heterocycle is optionally substituted with one or more groups independently selected from halo, cyano, nitro, $NR^eR^f$, $-CR^g(=N)N(R^g)_2$, $-NR^gC(=N)-N(R^g)_2$, $-NR^g-C(=NR^g)R^g$, $(C_1-C_3)$alkyl, $(C_1-C_3)$alkoxy, $(C_1-C_3)$alkanoyl, $(C_1-C_3)$alkoxycarbonyl, $(C_1-C_3)$alkanoyloxy, aryl, heteroaryl, and heterocycle;
$R^2$ is H or $(C_1-C_6)$alkyl that is optionally substituted with one or more groups independently selected from $-OR^k$, halo, $NR^eR^f$, $NR^eR^f$, $-CR^g(=N)N(R^g)_2$, $-NR^gC(=N)-N(R^g)_2$, and $-NR^g-C(=NR^g)R^g$;
$R^3$ is:

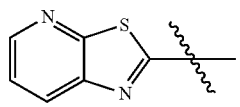 [SMILES: *c1nc2cccnc2s1]

which is substituted with one or more groups independently selected from $(C_1-C_6)$alkyl, and $(C_3-C_8)$cycloalkyl, wherein any $(C_1-C_6)$alkyl and $(C_3-C_8)$cycloalkyl is optionally substituted with one or more groups independently selected from halo and $(C_1-C_6)$alkyl that is optionally substituted with one or more groups independently selected from halo;
W is $-NHCOR^a$, $-N(COR^a)(COR^b)$, $-NR^aCH_2OR^a$, $-NHC(=O)OR^a$, $-NHC(=O)NR^aR^b$, or $-N(R^a)SO_mR^d$;
each $R^a$ is independently selected from H, aryl, heteroaryl, heterocycle, $(C_3-C_8)$cycloalkyl, $(C_3-C_8)$cycloalkyl$(C_1-C_6)$alkyl and $(C_1-C_6)$alkyl that is optionally substituted with one or more groups independently selected from hydroxy, halo, cyano, $(C_1-C_6)$alkoxycarbonyl, aryl, heteroaryl, $-NR^eR^f$, $-CR^g(=N)N(R^g)_2$, $-NR^gC(=N)-N(R^g)_2$, $-NR^g-C(=NR^g)R^g$ and heterocycle; wherein any aryl, heteroaryl, heterocycle, and $(C_3-C_8)$cycloalkyl$(C_1-C_6)$alkyl of $R^a$ is optionally substituted with one or more groups independently selected from hydroxy, halo, cyano, trifluoromethoxy, $(C_1-C_6)$alkyl, $(C_1-C_6)$alkoxy, halo$(C_1-C_6)$alkyl, $-NR^eR^f$, $-CR^g(=N)N(R^g)_2$, $-NR^gC(=N)-N(R^g)_2$, $-NR^g-C(=NR^g)R^g$, and $(C_1-C_6)$alkoxycarbonyl;

each $R^b$ is independently selected from H and $(C_1-C_6)$alkyl that is optionally substituted with one or more groups independently selected from hydroxy, halo, cyano, $(C_1-C_6)$alkoxycarbonyl, aryl, heteroaryl, $-NR^eR^f$, $-CR^g(=N)N(R^g)_2$, $-NR^gC(=N)-N(R^g)_2$, $-NR^g-C(=NR^g)R^g$, and heterocycle;
each $R^d$ is independently selected from OH, $-NH_2$, $-NR^eR^f$, aryl, heteroaryl, heterocycle, and $(C_1-C_6)$alkyl that is optionally substituted with one or more groups independently selected from hydroxy, halo, cyano, $(C_1-C_6)$alkoxycarbonyl, aryl, heteroaryl, $-NR^eR^f$, $-CH(=N)NH_2$, $-NHC(=N)-NH_2$, $-NH-C(=NH)R$, and heterocycle;
each $R^e$ is independently selected from H, aryl, heteroaryl, heterocycle, and $(C_1-C_6)$alkyl that is optionally substituted with one or more groups independently selected from hydroxy, halo, cyano, $(C_1-C_6)$alkoxycarbonyl, aryl, heteroaryl, and heterocycle; and each $R^f$ is independently selected from H and $(C_1-C_6)$alkyl that is optionally substituted with one or more groups independently selected from hydroxyl, halo, cyano, $(C_1-C_6)$alkoxycarbonyl, aryl, heteroaryl, and heterocycle; or $R^e$ and $R^f$ together with the nitrogen to which they are attached form a aziridino, azetidino, morpholino, piperazino, pyrrolidino or piperidino;
each $R^g$ is independently selected from H and $(C_1-C_6)$alkyl that is optionally substituted with one or ore groups independently selected from halo;
each $R^k$ is independently selected from H or $(C_1-C_6)$alkyl that is optionally substituted with one or ore groups independently selected from hydroxy, halo, oxo, carboxy, $(C_1-C_6)$alkoxy, $(C_1-C_6)$alkoxycarbonyl, and $(C_1-C_6)$alkanoyloxy;
m is 0, 1, or 2; and
n is 1, 2, 3, or 4;
or a salt thereof.

2. The compound of claim 1 wherein $R^3$ is:

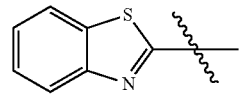

which is substituted with one or more groups independently selected from trifluoromethyl, pentafluoroethyl, or 1-(trifluoromethyl)cyclopropyl.

3. A compound of formula (I):

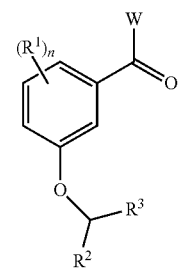

(I)

wherein:
each $R^1$ is independently selected from hydrogen, halo, cyano, nitro, $(C_1-C_6)$alkyl, $(C_1-C_6)$alkoxy, $(C_1-C_6)$alkanoyl, $(C_1-C_6)$alkoxycarbonyl, $(C_1-C_6)$alkanoyloxy, aryl, heteroaryl, heterocycle, and $NR^eR^f$, wherein each ($C_1$-$C_6$)alkyl, ($C_1$-$C_6$)alkoxy, ($C_1$-$C_6$)alkanoyl, ($C_1$-$C_6$)alkoxycarbonyl, ($C_1$-$C_6$)alkanoyloxy, aryl, heteroaryl, and heterocycle is optionally substituted with one or more groups independently selected from halo, cyano, nitro, $NR^eR^f$, —$CR^g$(=N)($R^g$)$_2$, —$NR^gC$(=N)—N($R^g$)$_2$, —$NR^g$—C(=$NR^g$)$R^g$, ($C_1$-$C_3$)alkyl, ($C_1$-$C_3$)alkoxy, ($C_1$-$C_3$)alkanoyl, ($C_1$-$C_3$)alkoxycarbonyl, ($C_1$-$C_3$)alkanoyloxy, aryl, heteroaryl, and heterocycle;

$R^2$ is H or ($C_1$-$C_6$)alkyl that is optionally substituted with one or more groups independently selected from —$OR^k$, halo, $NR^eR^f$, $NR^eR^f$, —$CR^g$(=N)N($R^g$)$_2$, —$NR^gC$(=N)—N($R^g$)$_2$, and —$NR^g$—C(=$NR^g$)$R^g$;

$R^3$ is:

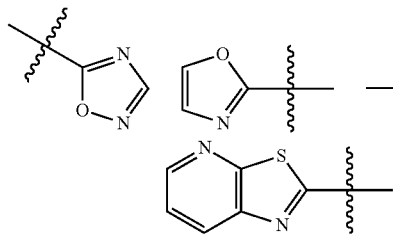

or which is optionally substituted with one or more groups independently selected from trifluoromethyl, pentafluoroethyl, or 1-(trifluoromethyl)cyclopropyl;

W is —$NHCOR^a$, —N($COR^a$)($COR^b$), —$NR^aCH_2OR^a$, —NHC(=O)$OR^a$, —NHC(=O)$NR^aR^b$, or —N($R^a$)$SO_mR^d$;

each $R^a$ is independently selected from H, aryl, heteroaryl, heterocycle, ($C_3$-$C_8$)cycloalkyl, ($C_3$-$C_8$)cycloalkyl($C_1$-$C_6$)alkyl and ($C_1$-$C_6$)alkyl that is optionally substituted with one or more groups independently selected from hydroxy, halo, cyano, ($C_1$-$C_6$)alkoxycarbonyl, aryl, heteroaryl, —$NR^eR^f$, —$CR^g$(=N)N($R^g$)$_2$, —$NR^gC$(=N)—N($R^g$)$_2$, —$NR^g$—C(=$NR^g$)$R^g$ and heterocycle; wherein any aryl, heteroaryl, heterocycle, and ($C_3$-$C_8$)cycloalkyl($C_1$-$C_6$)alkyl of $R^a$ is optionally substituted with one or more groups independently selected from hydroxy, halo, cyano, trifluoromethoxy, ($C_1$-$C_6$)alkyl, ($C_1$-$C_6$)alkoxy, halo($C_1$-$C_6$)alkyl, —$NR^eR^f$, —$CR^g$(=N)N($R^g$)$_2$, —$NR^gC$(=N)—N($R^g$)$_2$, —$NR^g$—C(=$NR^g$)$R^g$, and ($C_1$-$C_6$)alkoxycarbonyl;

each $R^b$ is independently selected from H and ($C_1$-$C_6$)alkyl that is optionally substituted with one or ore groups independently selected from hydroxy, halo, cyano, ($C_1$-$C_6$)alkoxycarbonyl, aryl, heteroaryl, —$NR^eR^f$, —$CR^g$(=N)N($R^g$)$_2$, —$NR^gC$(=N)—N($R^g$)$_2$, —$NR^g$—C(=$NR^g$)$R^g$, and heterocycle;

each $R^d$ is independently selected from OH, —$NH_2$, —$NR^eR^f$, aryl, heteroaryl, heterocycle, and ($C_1$-$C_6$)alkyl that is optionally substituted with one or more groups independently selected from hydroxy, halo, cyano, ($C_1$-$C_6$)alkoxycarbonyl, aryl, heteroaryl, —$NR^eR^f$, —CH(=N)$NH_2$, —NHC(=N)—$NH_2$, —NH—C(=NH)R, and heterocycle;

each $R^e$ is independently selected from H, aryl, heteroaryl, heterocycle, and ($C_1$-$C_6$)alkyl that is optionally substituted with one or more groups independently selected from hydroxy, halo, cyano, ($C_1$-$C_6$)alkoxycarbonyl, aryl, heteroaryl, and heterocycle; and each $R^f$ is independently selected from H and ($C_1$-$C_6$)alkyl that is optionally substituted with one or more groups independently selected from hydroxyl, halo, cyano, ($C_1$-$C_6$)alkoxycarbonyl, aryl, form a aziridino, azetidino, morpholino, piperazino, pyrrolidino or piperidino;

each $R^g$ is independently selected from H and ($C_1$-$C_6$)alkyl that is optionally substituted with one or ore groups independently selected from halo;

each $R^k$ is independently selected from H or ($C_1$-$C_6$)alkyl that is optionally substituted with one or ore groups independently selected from hydroxy, halo, oxo, carboxy, ($C_1$-$C_6$)alkoxy, ($C_1$-$C_6$)alkoxycarbonyl, and ($C_1$-$C_6$)alkanoyloxy;

m is 0, 1, or 2; and n is 1, 2, 3, or 4;

or a salt thereof.

4. The compound of claim 1 wherein:

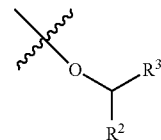

is selected from:

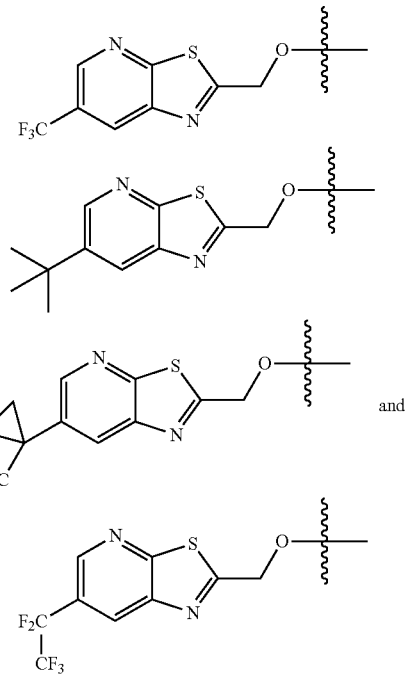

and

5. The compound:

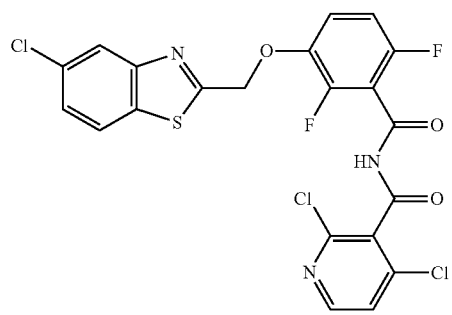

115
-continued
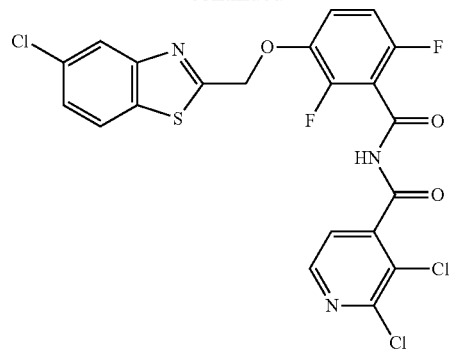
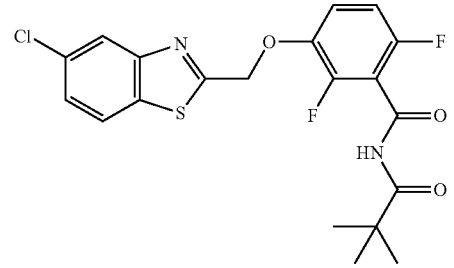
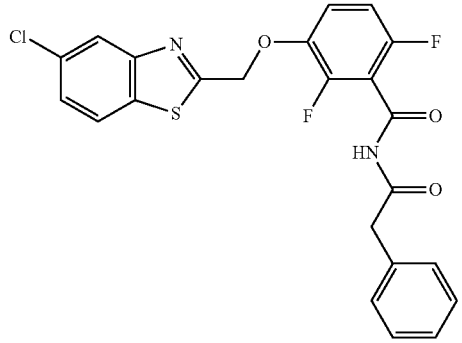
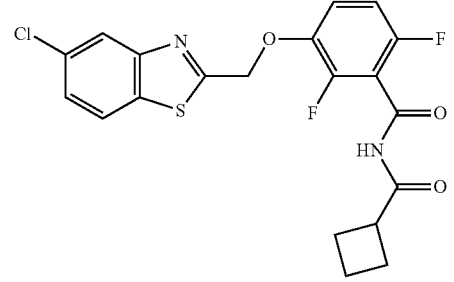
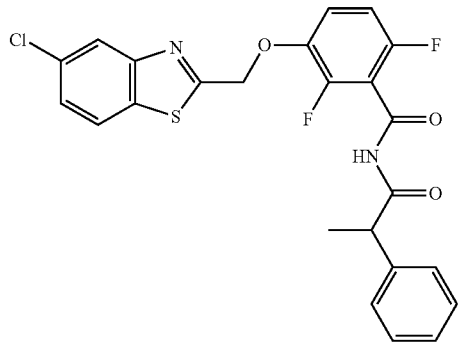
116
-continued
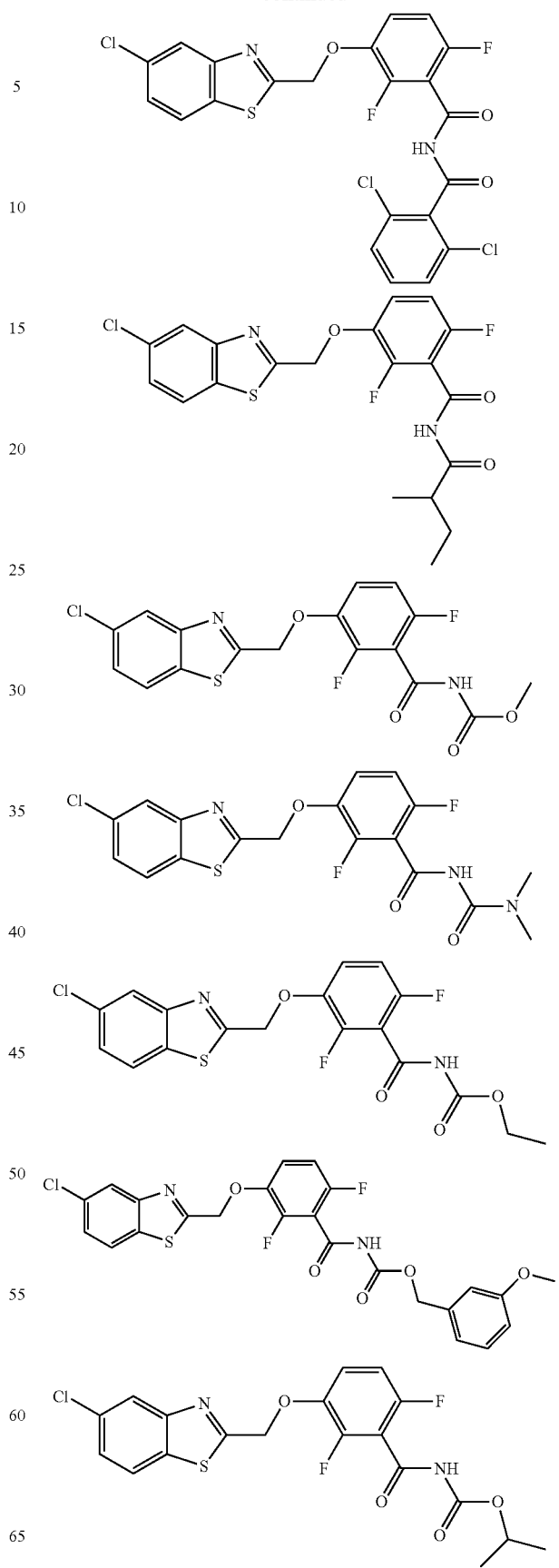

117
-continued
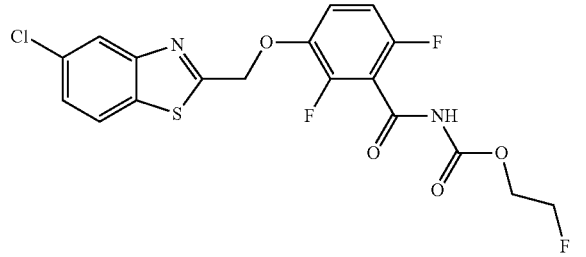
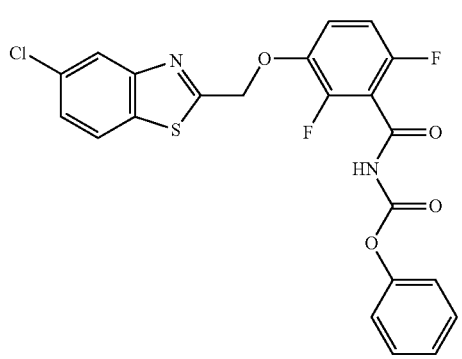
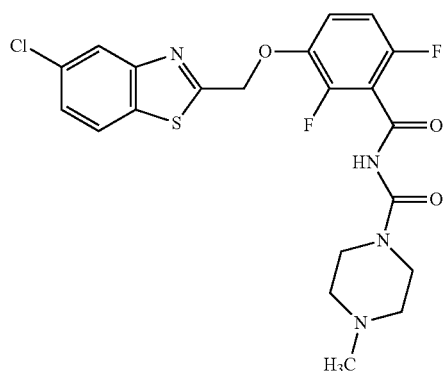
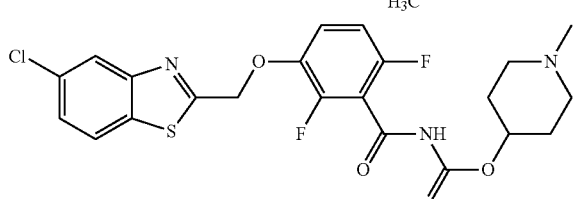
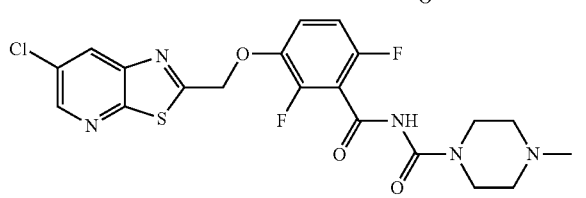
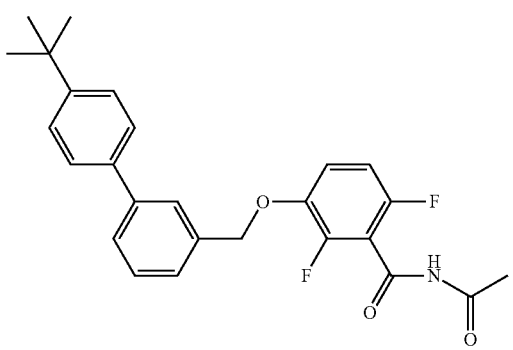
118
-continued
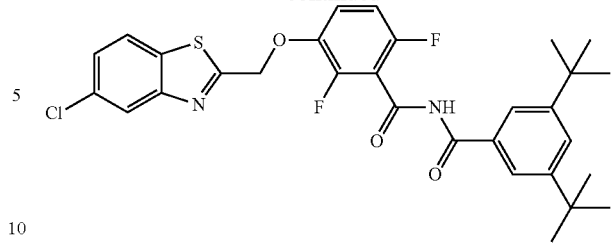
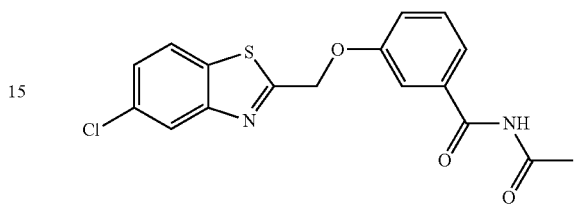
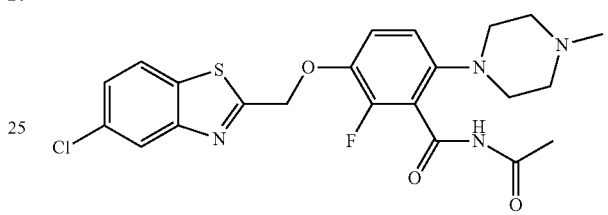
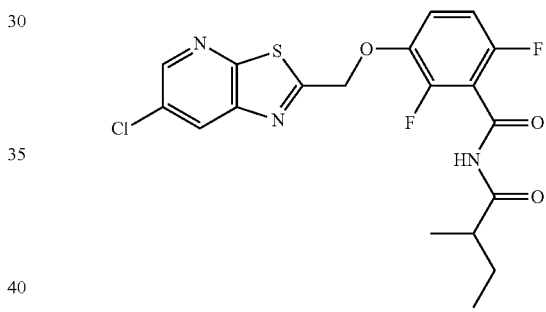
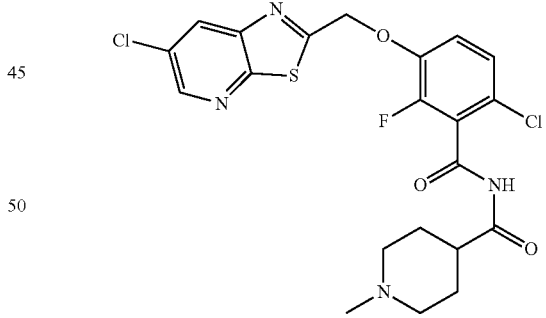
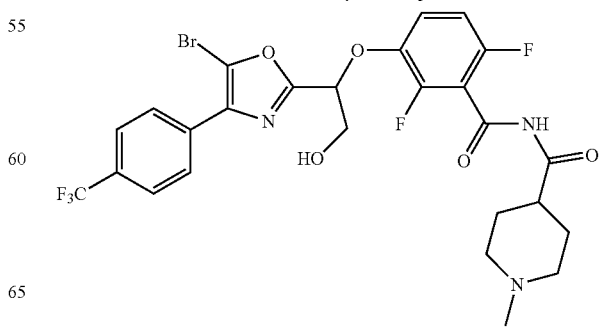

-continued
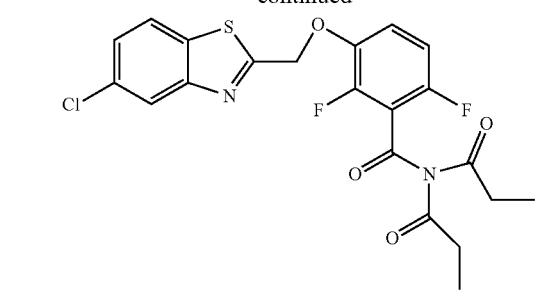
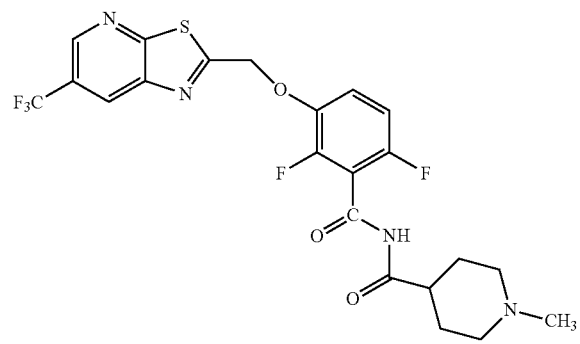
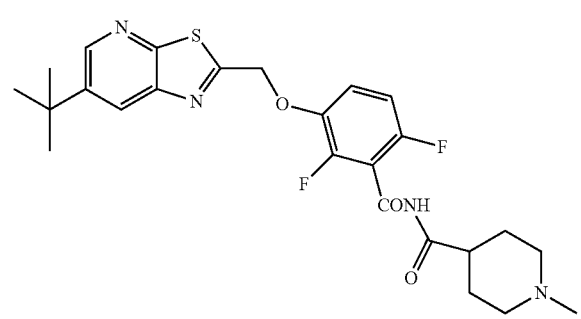
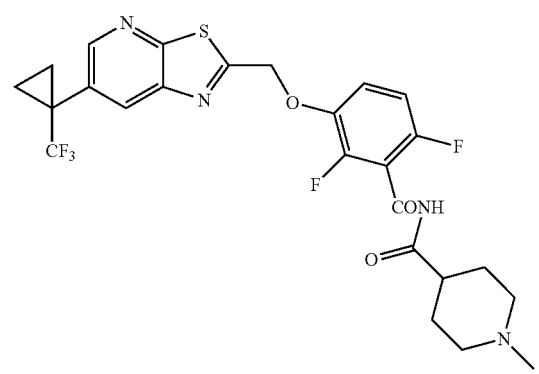
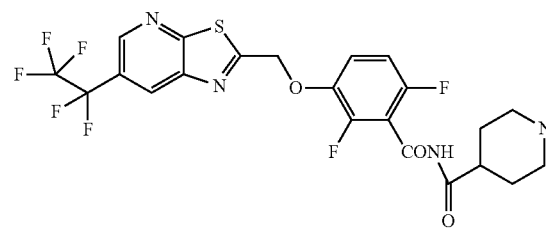
or a salt thereof.
6. The compound:
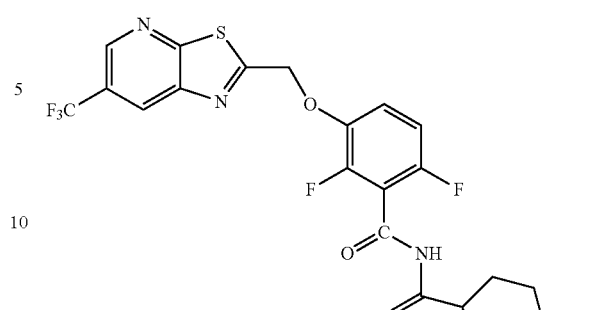
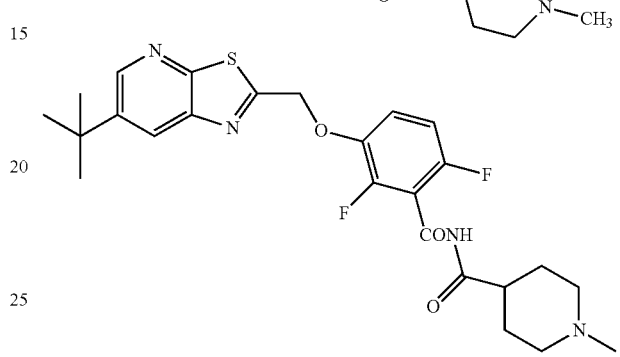
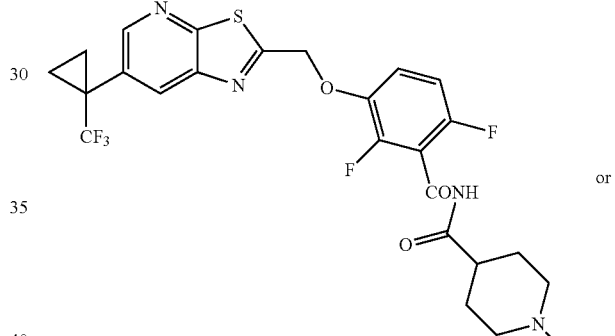
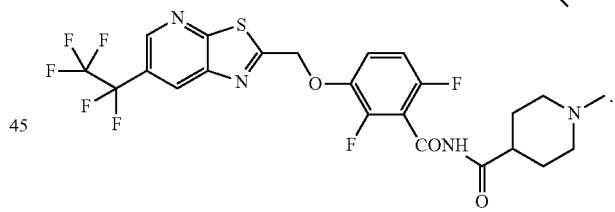
or
or a salt thereof.
7. The compound:
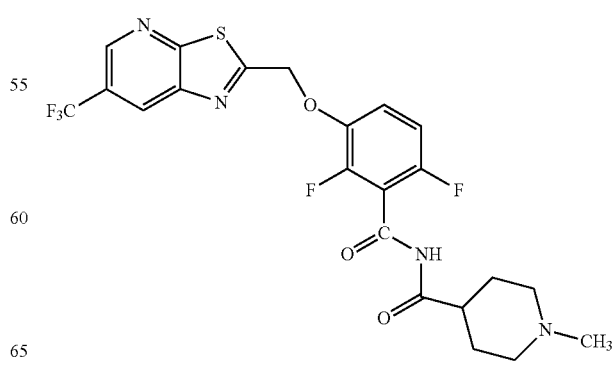
or a salt thereof.

8. A pharmaceutical composition comprising a compound of formula I as described in claim 1 or a pharmaceutically acceptable salt thereof, and a pharmaceutically acceptable vehicle.

9. A pharmaceutical composition comprising a compound of formula I as a described in claim 3 or a pharmaceutically acceptable salt thereof, and a pharmaceutically acceptable vehicle.

10. A pharmaceutical composition comprising a compound of formula I as described in claim 7 or a pharmaceutically acceptable salt thereof, and a pharmaceutically acceptable vehicle.

11. The compound:

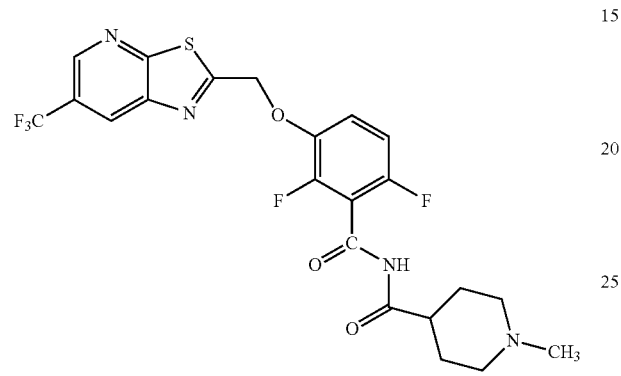

or a pharmaceutically acceptable salt thereof.

* * * * *